(12) United States Patent
Karlov et al.

(10) Patent No.: US 8,068,993 B2
(45) Date of Patent: *Nov. 29, 2011

(54) DIAGNOSING INAPPARENT DISEASES FROM COMMON CLINICAL TESTS USING BAYESIAN ANALYSIS

(75) Inventors: Valeri I. Karlov, Boston, MA (US); Bernard Kasten, Cincinnati, OH (US); Carlos E. Padilla, Lexington, MA (US); Edward T. Maggio, San Diego, CA (US); Frank Billingsley, Alexandria, VA (US)

(73) Assignee: Quest Diagnostics Investments Incorporated, Wilmington (DE)

( * ) Notice: Subject to any disclaimer, the term of this patent is extended or adjusted under 35 U.S.C. 154(b) by 529 days.

This patent is subject to a terminal disclaimer.

(21) Appl. No.: 12/140,880

(22) Filed: Jun. 17, 2008

(65) Prior Publication Data

US 2009/0024332 A1    Jan. 22, 2009

Related U.S. Application Data

(63) Continuation of application No. 10/138,068, filed on May 1, 2002, now Pat. No. 7,392,199.

(60) Provisional application No. 60/287,991, filed on May 1, 2001.

(51) Int. Cl.
*G01N 33/50* (2006.01)
*G01N 27/72* (2006.01)
*G01R 29/12* (2006.01)
*G01R 29/14* (2006.01)

(52) U.S. Cl. .................. 702/19; 702/70; 702/71; 702/83

(58) Field of Classification Search .................... 702/19, 702/20, 179, 181, 185, 186, 189; 435/6; 703/11; 705/2; 707/7

See application file for complete search history.

(56) References Cited

U.S. PATENT DOCUMENTS

| | | | |
|---|---|---|---|
| 5,386,829 A | 2/1995 | Diamond | |
| 5,778,893 A | 7/1998 | Potter | |
| 5,935,060 A | 8/1999 | Iliff | |
| 6,125,235 A | 9/2000 | Padilla et al. | |
| 6,221,592 B1 * | 4/2001 | Schwartz et al. | 435/6 |
| 6,242,190 B1 | 6/2001 | Freire et al. | |

(Continued)

FOREIGN PATENT DOCUMENTS

WO    WO 01/35316    5/2001

(Continued)

OTHER PUBLICATIONS

Crawley et al., Physical identification for control of flexible structures. Special Course, MIT Space Engineering Research Center, 1993.

(Continued)

*Primary Examiner* — Eliseo Ramos Feliciano
*Assistant Examiner* — Felix Suarez
(74) *Attorney, Agent, or Firm* — Foley & Lardner LLP

(57) ABSTRACT

A system and method of diagnosing diseases from biological data is disclosed. A system for automated disease diagnostics prediction can be generated using a database of clinical test data. The diagnostics prediction can also be used to develop screening tests to screen for one or more inapparent diseases. The prediction method can be implemented with Bayesian probability estimation techniques. The system and method permit clinical test data to be analyzed and mined for improved disease diagnosis.

24 Claims, 25 Drawing Sheets

U.S. PATENT DOCUMENTS

| | | | |
|---|---|---|---|
| 6,246,975 B1 * | 6/2001 | Rivonelli et al. | 703/11 |
| 6,270,456 B1 | 8/2001 | Iliff | |
| 7,043,476 B2 * | 5/2006 | Robson | 1/1 |
| 7,076,437 B1 | 7/2006 | Levy | |
| 7,392,199 B2 * | 6/2008 | Karlov et al. | 705/2 |
| 2001/0053875 A1 | 12/2001 | Iliff | |
| 2002/0002325 A1 | 1/2002 | Iliff | |
| 2002/0013515 A1 | 1/2002 | Iliff | |
| 2002/0016529 A1 | 2/2002 | Iliff | |
| 2002/0040183 A1 | 4/2002 | Iliff | |
| 2002/0052540 A1 | 5/2002 | Iliff | |
| 2002/0068857 A1 | 6/2002 | Iliff | |
| 2003/0158672 A1 | 8/2003 | Ramnarayan et al. | |
| 2003/0233197 A1 | 12/2003 | Padilla et al. | |
| 2005/0004766 A1 | 1/2005 | Ramnarayan et al. | |
| 2005/0191691 A1 | 9/2005 | Stanton | |

FOREIGN PATENT DOCUMENTS

| | | |
|---|---|---|
| WO | WO 02/087431 | 11/2002 |
| WO | WO 03/081211 | 10/2003 |

OTHER PUBLICATIONS

Karlov et al., Identification of Model Parameters and Associated Uncertainties for Robust Control Design, Journal of Guidance, Control, Dynamics, 17(3): 495-504, 1994.

Malyshev et al., Optimization and Observation and Control Processes AIAA Education Series, Washington, D.C., p. 166, 1992.

Shannon, A Mathematical theory of communication. The Bell System Technical Journal, 27(3): 379-423, 1948.

Shannon, A Mathematical theory of communication (Concluded from Jul. 1948 Issue) Part III: Mathematical Preliminaries, The Bell System Technical Journal, 27:623-656, 1948.

Willis, Ambulation monitoring and fall detection system using dynamic belief networks. Thesis Report (2000), School of Computer Science and Software Engineering Monash University, http://www.csse.monash.edu.su/hins/projects/2000/Daniel.Willis/node5.html (accessed on Aug. 3, 2002).

* cited by examiner

DIAGNOSING INAPPARENT DISEASES FROM COMMON CLINICAL TESTS USING BAYESIAN ANALYSIS

REFERENCE TO PRIORITY DOCUMENT

This application is a continuation of U.S. patent application Ser. No. 10/138,068, filed May 1, 2002, now U.S. Pat. No. 7,392,199 which claims priority under 35 U.S.C. §119(e) to U.S. Provisional Patent Application Ser. No. 60/287,991 entitled "Method Of Diagnosing Inapparent Diseases From Common Clinical Tests Using A Bayesian Analysis To Mine For Hidden Patterns In A Database Via Data Fusion And Integration" by V. Karlov et al., filed May 1, 2001. Priority of the filing date of May 1, 2001 is hereby claimed, and the disclosure of above-referenced applications are hereby incorporated by reference for all purposes.

BACKGROUND OF THE INVENTION

1. Field of the Invention

The invention relates to bioinformatics and, more particularly, to formulating disease diagnoses from clinical test data.

2. Description of the Related Art

In the area of disease diagnosis and detection, clinical tests are used to obtain data regarding a patient. The clinical tests yield a large volume of data, including patient symptoms and test results, as well as patient characteristics, such as age, gender, geographic location, and weight. The data can vary depending on the progression of a particular disease and when the clinical tests are conducted on a patient. The amount of clinical test data available is growing larger as additional tests are performed on an increasing number of patients.

The multitude of clinical test data that is available does not necessarily lead to an improvement in disease diagnosis for a patient. Indeed, the opposite can be true, as the volume of clinical test data and the high dimensionality of such data lead to a large quantity of possible diagnoses that can result from the data. A single patient can have multiple diagnoses that could result from the same data set. Additionally, the data can contain patterns that are not readily apparent or could contain information related to diseases that are not commonly diagnosed, difficult to diagnose, or for which a diagnostic test is not available or does not exist. This can lead to an inefficient use of clinical data wherein the analysis of the data leads to improper diagnoses or to missed diagnoses due to a failure to spot patterns or connections in the data.

In view of the foregoing, it should be apparent that there is a need for a method of mining and analyzing clinical test result data in connection with disease diagnosis. The present invention fulfills this need.

SUMMARY OF THE INVENTION

In accordance with the invention, there is disclosed a system and method of diagnosing diseases from biological data. A system for automated disease diagnostics prediction can be generated using a database of clinical test data. The diagnostics prediction can also be used to develop screening tests to screen for one or more inapparent diseases. In this way, clinical test data can be analyzed and mined for improved disease diagnosis.

In one aspect of the invention, a disease condition of a patient is diagnosed, based on analysis of clinical data for a population of individuals to whom a set of tests were administered. Next, a Bayesian statistical analysis is performed to estimate a first hypothesis-conditional probability density function $p(x|H1)$ where the hypothesis H1 relates to a diagnosis condition (such as a disease state or other diagnosis), and to estimate a second hypothesis-conditional probability density function $p(x|H2)$ where the hypothesis H2 relates to a non-diagnosis (such as a disease-free) condition. Next, a prior probability density function $p(H)$ is determined for the disease hypotheses H1 and H2, and next a posterior test-conditional probability density function $p(H|x)$ is determined for each of the hypotheses H1 and H2, and clinical data records x. With these probability estimates based on the clinical data, a diagnosis probability of a new patient with test results x for the H1 disease condition is provided, based on the determined posterior test-conditional probability density function $p(H1|x)$ as compared to the posterior test-conditional probability density function $p(H2|x)$ and one or more test results of the new patient. This technique represents an application of Bayesian probability estimation applied to clinical data. This methodology can be especially useful in identifying inapparent diseases from the clinical data, such as when screening tests for a disease condition are not readily available.

In another aspect of the invention, a method is provided for identifying a patient disease diagnosis that appears to be mislabeled. Each patient who has contributed a data record to the clinical data, including one or more test results, will be associated with a clinical disease diagnosis. The possibility of a mislabeling is identified when a data analysis such as described above is performed and a set of probability density functions (pdf) are produced that can provide a hypothesized disease diagnosis for each patient, as well as for new patients. This analysis can identify a patient to whom one or more of the tests was administered, but for whom the disease diagnosis predicted by the inventive method is different from the clinical diagnosis assigned to that patient. If a clinical diagnosis is determined to be mislabeled, that patient's data record can be removed from consideration in performing a future iteration of the estimation technique in accordance with the invention.

The invention also provides an improved application of Bayesian analysis to the difficulties of incomplete data records and multidimensional analysis. In accordance with the invention, test data from a patient population are processed to determine an estimate for one or more hypothesis-conditional probability density functions $p(x|H_k)$ for a set X of the test data, conditioned on a set H of multiple hypotheses relating to the test data. Next, a set of prior probability density functions $p(H_k)$ is determined for each hypothesis of the set H. A set of posterior test conditional probability density functions $p(H_k|x)$ for the hypotheses conditioned on a new data x is then determined. The invention includes providing a global estimator of the $p(x|H_k)$ functions, produced in accordance with the uncertainties in the statistical characteristics of the test data relating to each hypothesis-conditional pdf $p(x|H_k)$. The data analysis method can optionally include a local estimate in determining the hypothesis-conditional $p(x|H_i)$ estimates, wherein the local estimate is produced in accordance with a discrete neighbor counting process for test data relative to the global estimate for the corresponding hypothesis-conditional pdf.

The invention also provides for the determination of an acceptance rate mechanism where the posterior probabilities of the disease versus the non-disease conditions are compared and their difference is required to be above a predetermined threshold before a prediction is accepted with confidence. The prediction threshold can be determined to account for uncertainties due to sparsity in the training population. This allows for an increase of specificity and sensitivity in a reduced subset of the population whereby more accurate predictions are possible.

In another aspect of the invention, a method is provided for identifying a posterior tree of possible diagnoses (multiple diagnosis problem) based on analysis of clinical data for a population of individuals to whom a set of tests were administered, and then a Bayesian statistical analysis is performed to estimate first a series of hypothesis-conditional probability density function $p(x|Hi)$ where the hypothesis Hi is one of a set of H possible diagnoses. Next, a prior probability density function $p(Hi)$ is determined for the disease hypotheses Hi, and next a posterior test-conditional probability density function $p(Hi|x)$ is determined for each of the hypotheses Hi clinical data records x. With these probability estimates based on the clinical data, a posterior diagnosis tree of a new patient with test results x for the probability of the Hi disease conditions is provided, based on the determined posterior test-conditional probability density functions $p(Hi|x)$ and one or more test results of the new patient.

The invention also provides for accounting for the statistical trends in the data (for example, changing clinical tests with patient's age) via the use of dynamic propagation equations.

Thus, in accordance with the invention, a detailed probabilistic model for disease diagnosis can be derived using biological data such as can be obtained from clinical tests. The probabilistic model can be used to optimize clinical tests to be administered on a patient and to arrive at a diagnosis regarding the patient.

Other features and advantages of the present invention should be apparent from the following description of the preferred embodiment, which illustrates, by way of example, the principles of the invention.

BRIEF DESCRIPTION OF THE DRAWINGS

FIGS. 18A-18-B are graphical representations of the data fusion strategy provided in accordance with the invention, with two tests processed (left side of drawing) and with three tests processed (right side of drawing).

DETAILED DESCRIPTION

A. Definitions

Figure 1:
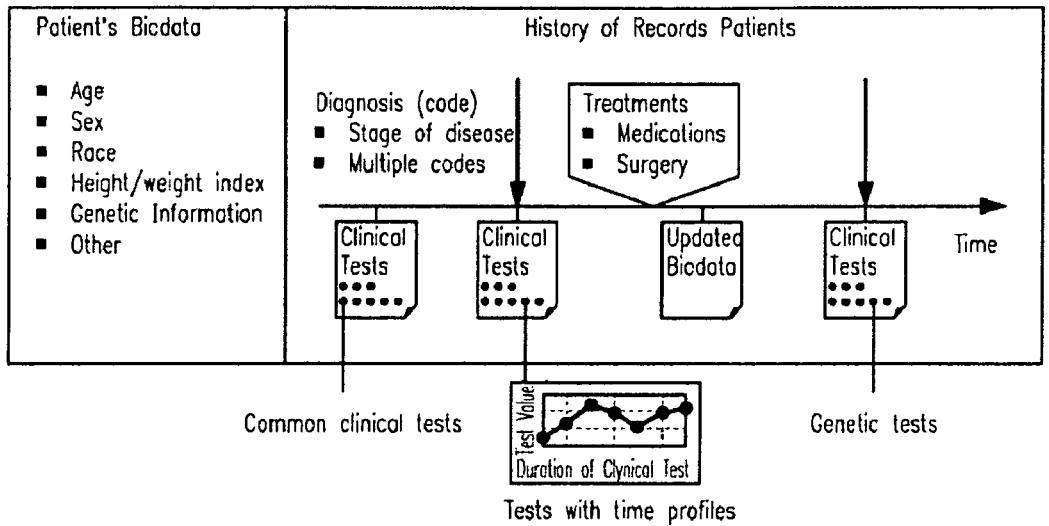
FIG. 1 is a graphical representation of the general process of analyzing medical data in accordance with the present invention for diagnostics.

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, "a discrete Bayesian analysis" refers to an analysis that uses a Bayes conditional probability formula as the framework for an estimation methodology. The methodology combines (1) a nonlinear update step in which new clinical data is convolved with the a priori probability of a discretized state vector of a possible diagnosis to generate an a posteriori probability; and (2) a prediction step wherein the computer 110 captures trends in the clinical test data, such as using a Markov chain model of the discretized state or measurements. Such analysis has been adapted herein for processing test data.

As used herein, diagnosis refers to a finding that a disease condition is present or absent or is likely present or absent. Hence a finding of health is also considered a diagnosis herein. Thus, as used herein, diagnosis refers to a predictive process in which the presence, absence, severity or course of treatment of a disease, disorder or other medical condition is assessed. For purposes herein, diagnosis also includes predictive processes for determining the outcome resulting from a treatment.

As used herein, subject includes any organism, typically a mammal, such as a human, for whom diagnosis is contemplated. Subjects are also referred to as patients.

As used herein, test data refer to any information suitable for analysis in the probabilistic model provided herein, such data includes biological data, astrophysics data, physical and chemical data and other such data.

As used herein, biological data refers to data obtained from subjects, such as human, and includes, but are not limited to, the results of biochemical, and physiological tests, such as such as blood tests and other clinical data the results of tests of motor and neurological function, medical histories, including height, weight, age, prior diseases, diet, smoking/non-smoker, reproductive history and any other data obtained during the course of a medical examination.

As used herein, biochemical test data refer to the results of any analytical methods, which include, but are not limited to, immunoassays, bioassays, chromatography, data from monitors, and imagers; measurements and also includes data related to vital signs and body function, such as pulse rate, temperature, blood pressure, the results of, for example, EKG, ECG and EEG, biorhythm monitors and other such information. The analysis can assess for example, analytes, serum markers, antibodies, and other such material obtained from the patient through a sample.

As used herein, patient historical data refer to data obtained from a patient, such as by questionnaire format, but typically does not include biochemical test data as used herein, except to the extent such data are historical; a desired solution is one that generates a number or result whereby a diagnosis of a disorder can be generated.

As used herein, the parameters identified from patient historical data are herein termed observation factors or values or variables. For example, patient data will include information with respect to individual patient's smoking habits. The variable associated with that will be smoking.

As used herein, inapparent diseases (used interchangeably with inapparent diseases) include diseases that are not readily diagnosed, are difficult to diagnose, diseases in asymptomatic subjects or subjects experiencing non-specific symptoms that do not suggest a particular diagnosis or suggest a plurality of diagnoses. They include diseases, such as Alzheimer's disease, Crohn's diseases, for which a diagnostic test is not available or does not exist. Diseases for which the methods herein are particularly suitable are those that present with symptoms not uniquely indicative of any diagnosis or that are present in apparently healthy subject. To perform the methods herein, a variety data from a subject presenting with such symptoms or healthy are performed. The methods herein permit the clinician to ferret out conditions, diseases or disorder that a subject has and/or is a risk of developing.

B. Methods

The methods provided herein can be used to analyze collections of test data using statistical analysis techniques. For example, an estimate for one or more hypothesis-conditional probability density functions $p(x|H_k)$ for a set X of the test data conditioned on a set H of hypotheses relating to the test data can be produced. The estimates can be represented, for example, as a histogram model. Next., a set of prior probability density functions $P(H_k)$ for each hypothesis of the set H is determined. For an initial estimation, a uniform probability can be used over the set H. Lastly, a set of posterior test-conditional probability density functions $p(H_k|x)$ for the hypotheses conditioned on a new data x is determined, wherein the $p(x|H_j)$ estimates include a global estimate produced in accordance with the uncertainties in the statistical characteristics of the test data relating to each hypothesis-conditional pdf $p(x|H_k)$. The global and local estimates are described in greater detail below. With the produced set of posterior test-conditional probability density functions $p(x|H_k)$, a set of probabilities can be generated for a new subject with a data record comprising x test values so that a likelihood probability can be assigned for that subject over the set of H hypotheses. In this way, the posterior probability estimates can be used to provide a most likely diagnosis probability for a new subject. If desired, a subset of test data can be used in a training mode to generate the posterior probability estimates, and another subset of the test data can be used in a predictive mode to compare a predicted diagnosis probability with an assigned diagnosis that is associated with each test data record. The sequence of operations to produce the posterior probabilities and subject-dependent diagnoses probabilities can be programmed for operation and execution by a computer.

The methods provided herein, for example, can be used to determine disease outcome, disease stage, disease diagnosis and/or survivability, and/or risk of developing a particular disease or condition including any disease known. Such diseases include, but are not limited to, neurodegenerative disorders, reproductive disorders, cardiovascular disorders, autoimmune disorders, inflammatory disorders, cancers, bacterial and viral infections, diabetes, arthritis and endocrine disorders. Other diseases include, but are not limited to, lupus, rheumatoid arthritis, endometriosis, multiple sclerosis, stroke, Alzheimer's disease, Parkinson's diseases, Huntington's disease, Prion diseases, amyotrophic lateral sclerosis (ALS), ischemias, atherosclerosis, risk of myocardial infarction, hypertension, pulmonary hypertension, congestive heart failure, thromboses, diabetes mellitus types I or II, lung cancer, breast cancer, colon cancer, prostate cancer, ovarian cancer, pancreatic cancer, brain cancer, solid tumors, melanoma, disorders of lipid metabolism; HIV/AIDS; hepatitis, including hepatitis A, B and C; thyroid disease, and any other disease or disorder.

The methods provided herein are applied to test data obtained as described by any method, including as described below, in order to predict or determine clinically relevant information. Such clinically relevant information includes, but is not limited to, compound toxicity (e.g., toxicity of a drug candidate, in the general patient population and in specific patients based on gene expression data; toxicity of a drug or drug candidate when used in combination with another drug or drug candidate (i.e., drug interactions); disease diagnosis; disease stage (e.g., end-stage, pre-symptomatic, chronic, terminal, virulent, advanced, etc.); disease outcome (e.g., effectiveness of therapy; selection of therapy); drug or treatment protocol efficacy (e.g., efficacy in the general patient population or in a specific patient or patient subpopulation; drug resistance); risk of disease, and survivability of a disease or in clinical trials (e.g., prediction of the outcome of clinical trials; selection of patient populations for clinical trials).

C. Biological Test Data

Test data for use in the methods provided herein includes any data for a subject, particularly data related to health or lack thereof. Such data is also referred to as clinical data, and includes data from medical examinations and includes, medical history, results of the physical examination, standard blood analyses, results of tests such as MRI scans, X-rays, EKGs and other tests. Blood analyses include, but are not limited to, CBC (complete blood count) and Chemical Screen tests. Such tests include, but are not limited to, tests for erythrocytes, creatinine, calcium, HIV 1 RNA, HN 1 AB, ABO group, magnesium, reagin AB, leukocytes, iron, phosphate, lactate dehydrogenase, neutrophils, lipoprotein beta, basophils, monocytes, platelet mean volume, eosinophils, cholesterol im HDL, basophils/100 leukocytes, monocytes/100 leukocytes, eosinophils/100 leukocytes, lymphocytes/100 leukocytes, iron saturation, glucose (protein bound), estradiol, iron binding capacity (unsaturated), albumin, folate, C reactive protein, cholesterol im LDL, cholesterol, cholesterol/HDL ratio, creatine kinase, transferrin saturation, ferritin, iron binding capacity, thyroxine (free), thyroxine (free index), thyroxine, prostate specific AG, hemoglobin A1C/hemoglobin total, coagulation tissue factor induced, hemoglobin, gamma glutamyl tran, thyrotropin, lymphocytes, triglycerides, globulin, alkaline phosphatase, bilirubin (total and direct), GGT, AST (SGOT), ALT (SGPT), amylase (serum), LD, platelets, hematocrit, albumin/globulin ratio, carbon dioxide, alanine aminotransferase, chloride, aspartate aminotransferase, sodium, urea nitrogen, urea nitrogen/creatinine ratio, uric acid, phosphate, potassium, total protein glucose, etc.

Other data that can be contained in the data sets for analysis using the methods provided herein includes, but is not limited to, patient data such as age, height, weight, sex. Also contemplated for inclusion in the data sets for analysis using the methods provided herein includes, but is not limited to, initial or suggested diagnoses of the treating physician or other health care provider.

The DBA Technique

A detailed description of a data analysis method and system will be described. The description includes a discussion about a methodology for statistical analysis of a data set to determine a probability for a disease outcome H1, where H1 is a diagnosis hypothesis such as a disease state or a general medical evaluation. The contrary hypothesis, H2, represents the non-diagnosis or disease-free condition. Another aspect of the description below relates to identification of apparent mislabeling of test data associated with individual subject data records, where the predicted disease diagnosis for a subject does not match an assigned diagnosis label for a subject's data record. The bulk of the description below relates to a particular DBA implementation for a multi-hypothesis analysis of test result data, where the hypotheses comprise a set of hypotheses $H_k$, with each hypothesis representing a different diagnosis condition.

1. Introduction

This description presents the main mathematical ideas underlying the Discrete Bayesian Approach (DBA) and shows how the DBA can be customized to the diagnosing inapparent diseases from common clinical tests.

The DBA is based on the fundamental Bayesian inference mechanism but goes far beyond by offering two major types of innovations:
1. New effective robust algorithms to fuse large amount of high-dimensional data
2. Unique customization to the physical structure of a particular problem Given its advanced mathematical algorithms and a highly customizable methodology, the DBA makes it possible to fuse all available statistical and structural information in order to extract maximum knowledge from the experiments.

It is important to note the significant differences between the DBA for diagnostics and a "classical Bayesian analysis." In the classical analysis, usually not more than one clinical test is considered in order to generate the posterior probabilities of a disease state, effectively the positive predictive value. The problem is then relatively straightforward and an estimate of the class probability density function for the test is usually a normal distribution, which is good enough if there is sufficient data. In particular, this one-test diagnostics using the "classical Bayesian analysis" can be used for diagnosing an apparent disease from a single specialty test developed for this disease. The DBA implementation here described goes significantly beyond this naive implementation since it is focused on diagnosing inapparent diseases from common clinical tests. First, its aim is to "fuse" information from hundreds to thousands of common clinical tests, not one or two. The multi-dimensional class probability density function presents a formidable estimation problem. If an approximation was attempted, and it was a naïve implementation of a multi-Gaussian distribution, the covariance matrix would be extremely large (1000's by 1000's) and cause numberless computational bottlenecks. It would be hard to estimate the correlations with any accuracy in the absence of very large amounts of data, and even in this case, a naïve Gaussian approximation would over-guarantee the probabilities. What is needed is a sophisticated approach to density estimation that can work computationally in very high dimensional spaces and that can handle realistic properties of the data, such as sparsity, uncertainty, and correlations. The description of the invention below focuses on these unique, innovative and highly useful techniques to estimate the conditional class probability density function for the multi-dimensional vector of tests.

2. Mathematical Statement of Diagnostics Problem

In this section a mathematical statement of the diagnostics problem is formulated. First, a conventional diagnostics problem is described, which deals only with Tests and Diagnoses fields. Second described is a structured diagnostics problem, which in addition to the Tests and Diagnoses fields also incorporates so called structural information. The structural information is highly specific to the medical diagnostics and includes such specifics as age trends in clinical tests, overlaps in diseases, multiple diagnoses, and historic clinical data, to name a few.

The DBA is especially suitable for solving a structured diagnostics problem since it can be customized to the particularities and variety of structural information. It is believed that utilizing this structural information is a key for increasing the accuracy of diagnostics. The use of this structural information is especially important when dealing with diagnostics of inapparent diseases where improvements come only from integrating (fusing) many clinical tests and other pieces of information related to the cause and progression of a disease.

Yet, even in a conventional Tests-Diagnoses statement there are mathematical (computational) challenges, as discussed below. The DBA addresses these challenges too. For simplicity, a conventional Tests-Diagnoses statement is used when describing more general mathematical aspects of the DBA algorithms such as handling high dimensionality. A structured statement will be used when the structure-dependent specifics are discussed.

It should be mentioned that general-purpose learning techniques such as neural nets (NN) and support vector machines (SVM) offer solutions only to the conventional diagnostics problem since they lack the ability to be customized for utilizing structural information for particular diagnostics problems.

2.1 Conventional Diagnostics Problem

The mathematical statement of the conventional diagnostics problem can be formulated as a standard classification problem (supervised learning).

The formulation starts from the availability of two major pieces of information:

(1) Matrix of observed tests X, represented by Equation (1):

$$X = \begin{pmatrix} x_1 \\ x_2 \\ \vdots \\ x_n \end{pmatrix} = \begin{pmatrix} x_{11} & x_{12} & \ldots & x_{1m} \\ x_{21} & x_{22} & \ldots & x_{2m} \\ \vdots & \vdots & \vdots & \vdots \\ x_{n1} & x_{n2} & \ldots & x_{nm} \end{pmatrix}. \quad (1)$$

Here the matrix X is of size n×m and its elements are the clinical test values, n is the number of patients, and m is the number of distinct tests (features). Thus, each column vector in X represents a patient, or data record. Correspondingly, the 1×m observation vector $x_i$ is associated with each patient. A realistic practical situation is assumed when not each patient has a complete list of tests (from all m possible tests).

(2) Vector of diagnosis D, represented by Equation (2):

$$D = \begin{pmatrix} D_1 \\ D_2 \\ \vdots \\ D_n \end{pmatrix} \quad (2)$$

Here the vector D is of size n×1. The diagnoses are assigned by doctors to each patient, and serve as classification labels. It is assumed that the diagnosis $D_i$ (for i-th patient) is defined on a discrete set of hypotheses (classes): $H=\{H_1, H_2, \ldots, H_N\}$. In this conventional statement it is assumed that the hypotheses are mutually exclusive and are also correct with the probability 1.0.

The goal is to use the combined data matrix X-D (tests X and diagnoses D) as a training set to develop a predictive diagnostics algorithm. This algorithm assigns a diagnosis $D_{new}$ (from the possible ones: $H_1, H_2, \ldots, H_N$) to each new patient who has a set of measured tests $x_{new}$. The assigned diagnosis should be "the best" in the sense of capturing the statistical dependency of the diagnoses D on the tests X in the X-D training set. There are different concepts how to interpret "the best." It is believed that the "BEST" (Bayesian ESTimation) offers the best inference mechanism that leads to the evaluation of a posteriori probabilistic measure p(·) over a set of hypotheses $H=\{H_1, H_2, \ldots, H_H\}$ as indicated in Equation (3):

$$p(H/x_{new}) = \{p(H_1/x_{new}), p(H_2/x_{new}), \ldots, p(H_N/x_{new})\} \quad (3)$$

In Equation (3) the probabilities are conditioned on the observation $x_{new}$. The probabilistic information of Equation (3) is used in the decision making process, which is usually based on the rule of maximum a posteriori probability:

$$\hat{H} = H_{\hat{k}}, \hat{k} = \arg\max_k p(H_k / x_{new}), k = 1, \ldots, N \quad (4)$$

Elaboration of this rule, especially in conjunction with the acceptance criterion will be presented in Section 3 as a part of the DBA.

It is important to note that this probabilistic interpretation is possible due to statistical nature of the diagnostics problem and is desirable from a practical point of view since a likelihood of each diagnosis is assessed. It is also important to note that the probabilistic measure plays the key role in integrating information in diagnostics problems with a complex multi-level structure (see Sections 2.2 and 3.2 presenting the structured diagnostics problem).

The predictive diagnostics algorithm works on each patient individually. However, it is important to evaluate statistical criteria that would characterize the overall quality of predictions on a large set of patients. In other words, the statement of the diagnostics problem should include a cross-validation procedure. It entails a splitting of the available data into two subsets: a training set and a control set. For simplicity, the notation X-D is used for a training set and denote a structurally equivalent control set as $X_C$-$D_C$ ($X_C$ of size $n_C \times m$ and $D_C$ of size $n_C \times 1$). In this case after training the predictive algorithm on the X-D data, this algorithm is used for diagnostics of the "new" patients from the control set. The predictive algorithm evaluates the "new" diagnoses $\hat{D}_C$ for all "new" patients. For this set the correct (as assumed) diagnoses $D_C$ are available. The mismatch between the correct diagnoses ($D_C$) and predicted diagnoses ($\hat{D}_C$) is the subject for analysis in order to evaluate the conventional statistical criteria such as sensitivity and specificity (see Section 3), the new criterion of acceptance (see Section 3) and ultimately predictive values. From a practical point of view, it is useful to perform a large number of random splits of the original data into different training and control sets. This so-called "boot-strapping" procedure or basically Monte-Carlo simulation makes it possible to estimate the distributions and parameters of the primary statistical criteria (sensitivity, specificity, acceptance and predictive values).

2.1.1 Challenges of the Conventional Diagnostics Problem

Here is emphasized the main challenges of the conventional diagnostics problem (Tests-Diagnoses), i.e. mainly computational challenges of the diagnostics problem. These challenges are associated with the key operation of the Bayesian-type algorithm—estimation of the hypothesis-conditional PDF (Probability Density Function) in the space of tests: $p(x/H_k)$, $k=1, \ldots, N$. The challenges are the following:

High dimensionality of the space of tests
Non-Gaussian distributions of tests
Uncertain statistics (especially correlations) due to finite samples and sparsity
Significant overlaps in the tests distributions It should be noted that although some other classification techniques such as NN or SVM do not use a probabilistic interpretation, they still face the challenges listed above. Although they address these challenges in ways different than the probabilistic methods do, they do not have the benefits of the probabilistic methods such as the use of a probabilistic measure as an universal "glue" to integrate various pieces of information.

Below is provided some elaboration on the challenges listed above, which are highly intertwined.

The challenge of high dimensionality (a so-called curse of dimensionality) might be significant even if the number of tests is equal to 5-6. Indeed, even with these dimensions of x it becomes difficult to evaluate and memorize the hypothesis-conditional PDF $p(x/H_k)$, $k=1, \ldots, N$, if the latter is non-Gaussian. The situation quickly aggravates with the increase of tests, making a direct non-parametric estimation of density simply infeasible. The parametric density estimation procedures, e.g. based on Gaussian approximations involving the estimates of the mean vector and covariance matrix, significantly alleviate the curse of dimensionality. But, again, if the density is significantly non-Gaussian or if it is difficult to parameterize it by any other functional form (e.g. β-function), the parametric methods become inaccurate.

Uncertainties in statistics are caused by the fact that typically there is a limited number of patients with the specified tests X (finite samples) and, to make matters worse, not each patient has all tests recorded (sparsity in data). Under these conditions it is difficult to estimate the density $p(x/H_k)$, $k=1, \ldots, N$, especially in the high-dimensional space of tests. Correspondingly, the estimated statistics $\hat{p}(x/H_k)$, $k=1, \ldots, N$ to be used in the predictive algorithm are uncertain. The most challenging technical difficulty here consists in the fact that the correlations (or more generally, statistical dependencies) become uncertain, which significantly complicates the fusion of those tests. It is a well-known fact that from finite samples it is more difficult to estimate the entire matrix of pair-wise correlations between all tests rather than the diagonal of this matrix (variances of tests). It is even more difficult to estimate higher order momenta, which formalize statistics of groupings of multiple tests. In addition to finite samples, the sparsity in the available data further complicates the density estimation, especially in terms of estimating mutual statistical dependencies between the test values.

The poor estimates of the density $\hat{p}(x/H_k)$, $k=1, \ldots, N$ could introduce large errors to the predictive algorithm especially in the case when the densities for each hypothesis are overlapped. These overlaps are typical for common clinical tests as potential discriminators between inapparent diseases and healthy state. The mathematical challenge due to overlaps is the following. On the one hand, it is beneficial to handle the overlapped distributions via the use of probabilistic measure for fusing a large amount of relatively low-discriminative tests. On the other hand, the accurate estimate of density is problematic.

In summary, it is widely recognized that it is a challenging mathematical problem to fuse the realistic data (high-dimensional, non-Gaussian, statistically uncertain due to finite samples and sparsity, and highly-overlapped). To put it in numbers, the real art of the data fusion consists in developing the robust algorithms to achieve the discrimination probability of 0.85-0.99 for a combination of multiple tests with the individual discrimination probabilities of 0.55-0.7.

2.2 Structured Diagnostics Problem

The structure of the diagnostics problem is defined by a structure of medical database available for diagnostics either from routine clinical operations or from specially designed experiments (studies).

FIG. 1 provides a general structure of a medical database with different types of information, in which the customized DBA could perform data mining leading to the enhanced diagnostics.

The formulation of structured diagnostics problem involves a more complex representation of the Tests-Diagnoses data than that of Equations (1) and (2), namely due to incorporation of new factors specific to the diagnostics problem:

(1) Matrix of Observed Tests $$X(\Phi, \Theta, T) = \begin{pmatrix} x_1(\phi_1, \theta_1, \tau_1) \\ x_2(\phi_2, \theta_2, \tau_2) \\ \vdots \\ x_n(\phi_n, \theta_n, \tau_n) \end{pmatrix} = \begin{pmatrix} x_{11}(\phi_{11}, \theta_{11}, \tau_{11}) & x_{12}(\phi_{12}, \theta_{12}, \tau_{12}) & \ldots & x_{1m}(\phi_{1m}, \theta_{1m}, \tau_{1m}) \\ x_{21}(\phi_{21}, \theta_{21}, \tau_{21}) & x_{22}(\phi_{22}, \theta_{22}, \tau_{22}) & \ldots & x_{2m}(\phi_{2m}, \theta_{2m}, \tau_{2m}) \\ \vdots & \vdots & \vdots & \vdots \\ x_{n1}(\phi_{n1}, \theta_{n1}, \tau_{n1}) & x_{n2}(\phi_{n2}, \theta_{n2}, \tau_{n2}) & \ldots & x_{nm}(\phi_{nm}, \theta_{nm}, \tau_{nm}) \end{pmatrix}. \tag{5}$$

Equation (5) formalizes that the value $x_{ij}$, i.e. the j-th clinical test ($j=1, \ldots, m$) of the i-th patient ($i=1, \ldots, n$), depends on the three additional factors: $\phi_{ij}$, $\theta_{ij}$, and $\tau_{ij}$. The factor $\phi$ is a discrete (e.g. binary) factor that represents, for example, sex or race of a patient or a type of medical treatment. The factor $\theta$ is a continuous factor that represents, for example, the patient's age (DOB) or the height/weight index. The factor $\tau$ is a factor of the patient's clinical history. Its formalization is a more complex task than for the first two factors. First, in a general case, $\tau$ is a vector factor reflecting the fact that the clinical tests for a patient were recorded at different times (presumably, over a long time interval, e.g. years): $\tau = \{\tau^{(1)}, \ldots, \tau^{(r)}, \ldots \tau^{(R_0)}\}$. The record times are expressed in relative to the patient's life units (current age). Note that the number of records $R_{ij}$ can be different for different patients and for clinical tests of each patient (including the situation with sparsity in the tests). Given this complex structure in a general case (when multiple historic records are present), Equation (5) is a data cell rather than a data matrix as in Equations (1) and (2) associated with the conventional diagnostics problem.

2) Vector of Diagnosis $$D(T) = \begin{pmatrix} D_1(\tau_1) \\ D_2(\tau_2) \\ \vdots \\ D_n(\tau_n) \end{pmatrix} \quad (6)$$

Here, like in Equation (2), the vector D is of size n×1. But, in this more general case each element of the vector D, $D_i(\tau_i)$, i=1, ..., n, depends on the additional factor $\tau_i$ (clinical history) and is a cell element which possibly stores a combination of other diagnoses from the list H={$H_1, H_2, \ldots, H_N$}. This combination of diseases in one patient eliminates the limitation of the conventional diagnostics problem that the hypotheses must be mutually exclusive. Different stages of a disease can be formalized in this more general "diagnosis label" too, which otherwise would pose a conceptual challenge for the conventional diagnostics problem.

2.2.1 Challenges of Structured Diagnostics Problem

The main challenge here consists in the fact that every real diagnostics problem has its very specific particularities and requires a significant effort to select and build an appropriate architecture of the statistical model. Thereby, the conventional mathematical challenges discussed in Section 2.1.1 can take place at each level of this architecture. For example, the challenge of uncertain statistics might exist both for a model of tests progression over time and for a model of the tests-diagnoses dependency.

3. Data Fusion Via the DBA Algorithms

SBI-Moldyn's DBA technology offers a rigorous statistical treatment of the realistic uncertain data. The DBA offers a powerful data fusion framework to extract hidden patterns of diseases in a high-dimensional space of clinical tests.

Figure 2:
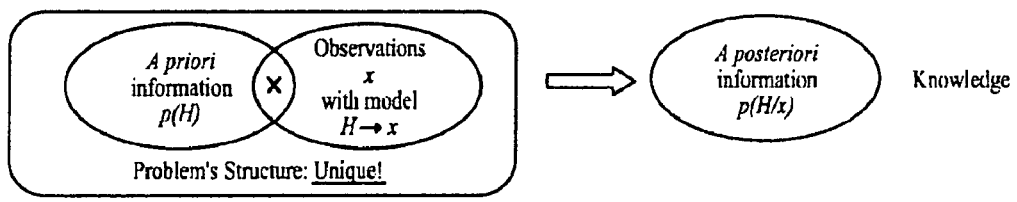
FIG. 2 is a graphical representation of a Bayesian inference mechanism as provided in accordance with the present invention.

The DBA takes its roots in the classical Bayesian inference mechanism. FIG. 2 provides a graphical interpretation of the Bayesian inference mechanism, as used in the design of the DBA.

The Bayesian formula is at the heart of the DBA's computational engine and is given in Equation (7):

$$p(H_k / x) = p(H_k) \cdot \frac{p(x/H_k)}{\sum_{q=1}^{N} p(H_q) p(x/H_q)}, k = 1, \ldots, N \quad (7)$$

As was described in Section 2.1, H stands for hypotheses (diagnoses), x stands for observed tests (it serves as an input argument) and p(·) is a probabilistic measure. In particular, $p(H_k)$, k=1, ..., N are the a priori probabilities for hypotheses and $p(x/H_k)$, k=1, ..., N are the hypothesis-conditional PDFs, which are represented (in the diagnostics problem) by their estimates $\hat{p}(x/H_k)$, k=1, ..., N. When using Equation (7) for diagnostics of a new patient who has the vector of tests $X_{new}$, one just needs to use a substitution $x=x_{new}$.

It is important to emphasize the fundamental nature of the Bayesian formula as a mathematical basis for data fusion. The Bayesian formula provides an advanced mathematical operation (comparing with the arithmetic operations +−x:) to deal with fuzziness of real world. This operation involves a probabilistic measure p(·)∈ [0,1] fur seamless integration (fusion) of different pieces of information, especially in the problems with complex physical structure. From a practical point of view, this operation provides a powerful mechanism for recursively incorporating new information, both quantitative and qualitative, to update the predictive model as more data/tests become available.

As was mentioned above, the DBA is based on the fundamental Bayesian inference mechanism of Equation (7), but offers two major types of innovations:

1. New effective robust algorithms to fuse large amount of high-dimensional data and
2. Unique customization to the physical structure of a particular problem. Correspondingly, the first type of innovations addresses the challenges of the conventional diagnostics problem (see Section 2.1.1), which are mainly mathematical (computational) challenges. The second type of innovations addresses the challenges of the structured diagnostics problem (see Section 3.2), which are mainly associated with a better and more detailed formalization of the practical aspects of the diagnostics problem.

To accomplish the first type of innovations, the DBA has important practical features such as efficient operations in the high-dimensional space of tests and robustness to data variability (including uncertain statistics). These innovations are described in detail in Section 3.1.

To accomplish the second type of innovations, the DBA offers new opportunities to incorporate the structure of a particular problem. This structure includes key factors that differentiate the data under analysis. This is illustrated by an example from the DBA's applications to medical diagnostics from common clinical tests.

Figure 3:
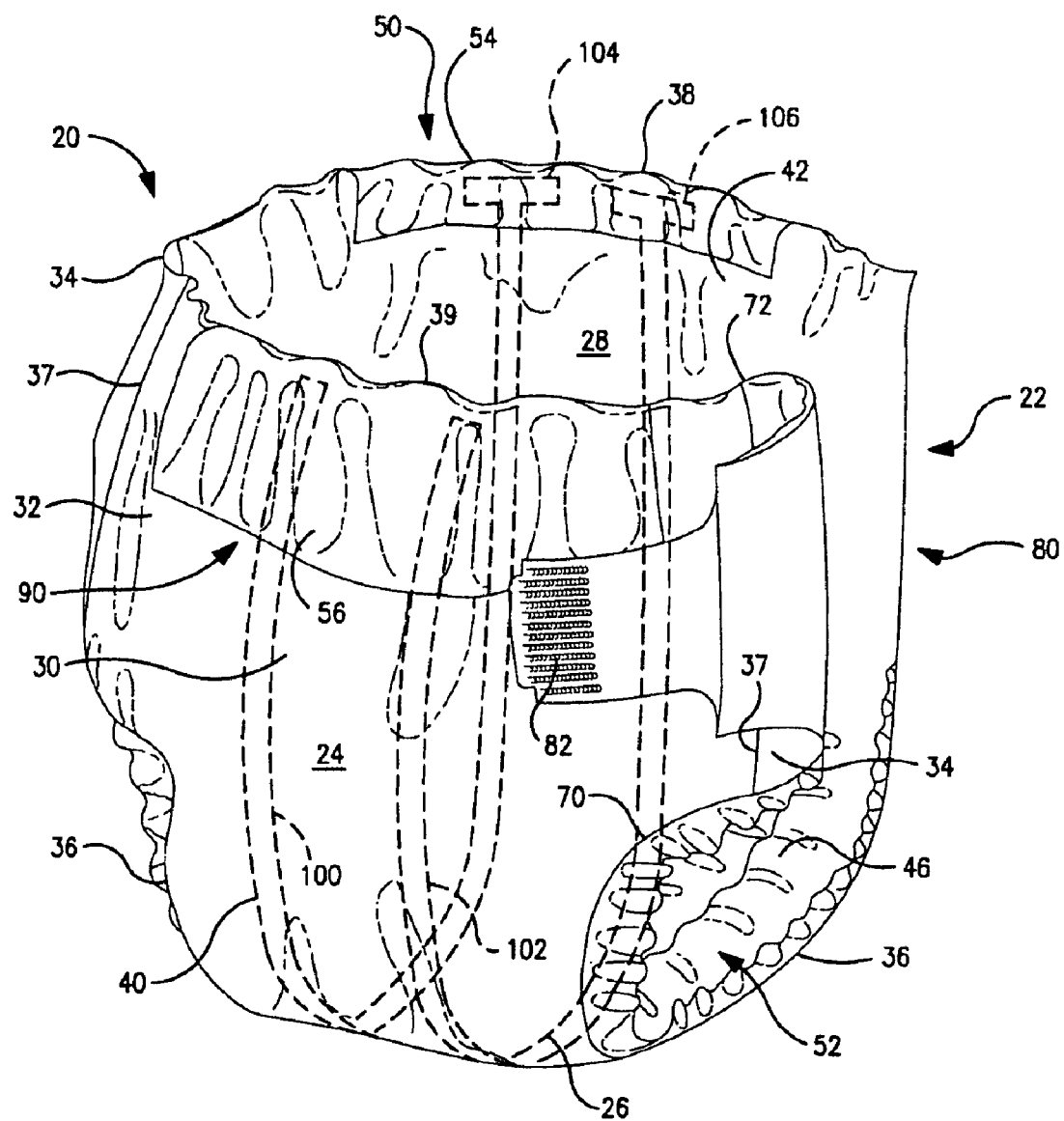
FIG. 3 is a graphical representation of the DBA technique for diagnosis of medical data in accordance with the invention.

FIG. 3 provides the general scheme for how the DBA works. The DBA has training and prediction modes. In the training mode, the DBA uses two conventional inputs for supervised learning (clinical tests and diagnoses for patients) as well as a third unique input through which is formalized the problem's structure. For example, for the medical diagnostics problem, statistical trends in clinical tests are formalized with structural data that includes age and combinations of diseases (using various stochastic models like Markov chains). In the prediction mode for new patients, the trained DBA maps the clinical tests into the a posteriori tree of diagnoses. The information content of this tree sharpens as new clinical tests are added. In this sense, the DBA extracts maximum knowledge and is much less sensitive to problems that arise from data variability. Other general-purpose classification techniques (such as neural nets and support-vector learning machines) lack this ability to be customized to the specific nature of the problem and thus to extract maximum information from the available data, given structural information.

3.1 The DBA for Solving Conventional Diagnostics Problem (Mathematical Innovations)

The key algorithmic problem in designing the DBA predictive algorithm consists is the estimation of the hypothesis-conditional PDF (Probability Density Function): $p(x/H_k)$, k=1, ..., N. The challenges of this operation were discussed in Section 2.1.1. In overcoming these challenges a philosophy is followed that the density should be estimated in a form and to an extent, which are sufficient for the development of an accurate prediction (classification) algorithm, in terms of evaluating reliable a posteriori probabilities $p(H/x_{new})$.

SBI-Moldyn's DBA offers new effective algorithms for density estimation and, thus, opens the way for fusing large high-dimensional datasets. In the following Section is described these algorithms highlighting the two highly interconnected aspects of the DBA: (1) efficient operations in high dimensional space; and (2) robustness to uncertainties.

3.1.1 Detailed Mathematical Description of the DBA Algorithm

The DBA provides efficient and robust operations in the high-dimensional space of tests. This requires development of special decomposition techniques. SBI-Moldyn's decomposition techniques are based on the novel idea of global-local estimation of the hypothesis-conditional density $p(x/H_k)$, $k=1, \ldots, N$. Correspondingly the DBA includes a combination of global and local estimates. The estimate is referred to as global when the density is estimated over the entire region of the test values. The estimate is referred to as local if it is associated with a local region in the space of tests.

The state-of-the-art pattern recognition methods use the global and local estimates separately. For example, the Bayesian-Gaussian parametric method (see e.g., Webb, A., *Statistical Pattern Recognition*, Oxford University Press, 1999.) involves global estimates of the hypothesis-dependent densities in a form of Gaussian distributions, for which the corresponding mean vectors and the covariance matrices are estimated. This method starts to suffer from a lack of accuracy when actual densities become more and more non-Gaussian. On the other hand, the non-parametric K-nearest neighbor method (see e.g., Webb, A., *Statistical Pattern Recognition*, Oxford University Press, 1999.) operates locally around a new data point and assigns to this point that hypothesis (class), which corresponds to the most frequent class possessed by its K nearest neighbors. Note that the K neighbors are selected here according to a Euclidean distance in the space of tests. The K-nearest neighbor method does not use any functional form for density, but has a few drawbacks such as a lack of probabilistic interpretation and the sensitivity to the choice of the K parameter (a small K might not be sufficient for making a class assignment, but a large K might involve a large local region where the density estimate will be smeared).

The diagnostics problem provides a practical application in which the global and local estimates would naturally complement to each other, and one really needs to integrate them into a unified prediction algorithm. The DBA effectively accomplishes this task.

3.1.1.1 Global Estimation of Density in the DBA

In our solution, the global estimate of the hypothesis-conditional density $p(x/H_k)$, $k=1, \ldots, N$ is important for revealing essential statistical dependencies (correlations) between tests, which is only possible when all data are used. Indeed, none of the local methods (e.g., K-nearest neighbors) can estimate the correlations between the tests and capitalize on this knowledge for a better classification. The global estimation is helped by the fact that the realistic distributions for the clinical tests are usually single-peak distributions ("core-and-tails" PDFs). This fact was confirmed on a large number of cases since the SBI-Moldyn's visualization tools allow for automated visualization of various scattering plots in 2D and 3D as well as ND (via parallel coordinates). See examples of scatter plots for clinical tests in Section 4 that show the typical shapes of distributions (1D plots) and emphasize the fact that the mutual correlations between the tests can be estimated only globally (2D and 3D plots).

Figure 4:
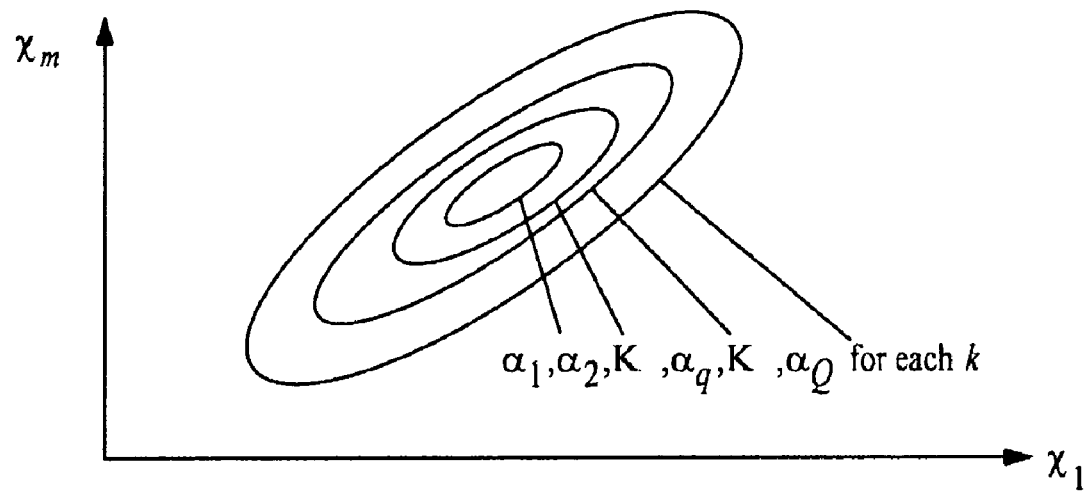
FIG. 4 is an illustration of the guaranteeing model of concentric ellipsoids for data fusion in accordance with the present invention.

The global estimate of hypothesis-conditional density $p(x/H_k)$, $k=1, \ldots, N$ is sought in the form of a guarantying model of concentric ellipsoids (see FIG. 4). The probabilistic measure of each q-th inter-ellipsoidal layer for each hypothesis $H_k$ is denoted as $\alpha_{q,k}$:

$$\alpha_{y,k} = \Pr\{x \in E_{q,k} \cap E_{q-1,k}, q=1, \ldots, Q, E_{o,k}=E_{l,k}\} \quad (8)$$

and the probabilities $\{\alpha_q\}$ satisfy the constraint $$\sum_{q=1}^{Q} \alpha_q = \overline{\alpha} \quad (9)$$

where $\overline{\alpha}$ is the guarantying probability of the entire ellipsoidal set, which is associated with removing the outliers in the hypothesis-conditional densities $p(x/H_k)$, $k=1, \ldots, N$. A practical recommendation here is to use $\overline{\alpha} \rightarrow 1$, e.g. $\overline{\alpha}=0.95$ as a standard (this number also corresponds to an approximate level of the expected sensitivity/specificity of the best screening test).

In Equation (8) the m-dimensional ellipsoid $E_{q,k}$ for each hypothesis $H_k$ is defined as follows $$E_{q,k} = \{x : (x - m_{x,k})^T P_{x,k}^{-1} (x - m_{x,k}) \leq \mu_{q,k}^2\} \quad (10)$$

where the m×1 vector x is the argument in the space of tests, the m×1 vector $m_{x,k}$ is the mean (center) of each ellipsoid, the m×m matrix $P_{x,k}$ is the ellipsoid's covariance matrix and the scalar $\mu_{q,k}^2$ defines the size of the q-th ellipsoid.

Correspondingly, the global estimate of density is calculated via the following formula of Equation (11):

$$\hat{P}_{glob}(x/H_k) = \alpha_{q,k} \text{ if } x \in E_{q,k} \cap E_{q-1,k}(E_{0,k}=E_{l,k}), k=1 \ldots, N \quad (11)$$

The guaranteeing model of the concentric ellipsoids is a generalization of the conventional Gaussian model. Indeed, in the case of Gaussian model for each hypothesis $H_k$ and for each q-th layer in Equations (8)-(10) the parameters $\alpha_{q,k}$ and $\mu_{q,k}^2$ would be related via the standard probability integrals for the n-dimensional Gaussian distribution. Unlike the conventional Gaussian model, the guaranteeing model of Equations (8)-(10) is adjusted (via stretching of ellipsoids) to the non-Gaussian nature of the test distributions. The guaranteeing nature of the ellipsoidal model comes from the following two facts: 1) the theorem "under the constraint of a fixed covariance matrix the function that maximizes the entropy is a Gaussian (see e.g., Shannon, C. E.; "A mathematical theory of communication," *Bell System Technical Journal*, Vol. 27, pp. 379-423 and 623-656, July and October, 1948);" and, 2) each ellipsoid associated with an instantaneous Gaussian is smeared so that its entropy is increased. The latter directly leads to increasing the entropy over the hypotheses, expressed via their a posteriori probabilities $$\{p(H_1/x), p(H_2/x), \ldots, p(H_N/x)\}:$$

$$H = -\sum_{k=1}^{N} p(H_k/x) \log[p(H_k/x)] \quad (12)$$

The computational convenience of the ellipsoidal model of Equations (8)-(10) consists in the fact that an operation with this model in Equation (11) is not ill-conditioned, as would be an operation of computing the value of the conventional Gaussian density in a high-dimensional space with correlated features.

3.1.1.1.1 The Algorithm for Evaluating the Guaranteeing Model of Concentric Ellipsoids Here is presented the algorithm for evaluating the guaranteeing model of concentric ellipsoids represented by Equations (8)-(10). This algorithm includes three major steps.

Step 1. Evaluate the robust estimate of the hypothesis-conditional mean vector and covariance matrix associated with the guaranteeing probability $\overline{\alpha}$.

This robust procedure seeks to reduce the effect of outliers on the density estimation. The following conventional estimation operations with the specially designed weights $w_i$ (see e.g. Webb, A., *Statistical Pattern Recognition*, Oxford University Press, 1999.) is used to estimate the hypothesis-conditional m×1 mean vector $m_{x,k}$ and the m×m covariance matrix $P_{x,k}$ for each hypothesis $H_k$:

$$m_{x,k} = \frac{\sum_{i \in I_k} w_{i,k} x_{i,k}}{\sum_{i \in I_k} w_{i,k}}, k = 1, \ldots, N \quad (13)$$

$$P_{x,k} = \frac{\sum_{i \in I_k} w_{i,k}^2 (x_{i,k} - m_{x,k})(x_{i,k} - m_{x,k})^T}{\sum_{i \in I_k} w_{i,k}^2 - 1}, k = 1, \ldots, N \quad (14)$$

In Equations (13) and (14) the m×1 vector $x_{i,k}$ (a transposed row of the test matrix X in Equation (1)) corresponds to the i-th patient in the k-th class (hypothesis). Also, in Equations (13) and (14), a set of indices $I_k$, $k=1, \ldots, N$ is selected from a set of all patients who are included in the training set and who are assigned a hypothesis $H_k$ as a diagnosis $D_i$:

$$I_k = \{i: D_i \equiv H_k, i=1, \ldots, n\}, k=1, \ldots, N \quad (15)$$

The weights $w_{i,k}$ in Equations (13) and (14) are defined as $$w_{i,k} = \frac{w_{i,k}(\mu_{i,k})}{\mu_{i,k}}, k = 1, \ldots, N \quad (16)$$

where $\mu_{i,k}$ is the ellipsoid-dependent distance $$\mu_{i,k} = [(x_i - m_{x,k})^T P_{x,k}^{-1} (x_i - m_{x,k})]^{\frac{1}{2}} \quad (17)$$

The scalar Gaussian decay function $w_{i,k}(\mu_{i,k})$, which reduces the contributions of the outliers, is defined as follows $$w_{i,k}(\mu) = \begin{cases} \mu & \text{if } \mu \leq \mu_0 \\ \mu_0 \exp\left\{-\frac{1}{2}(\mu - \mu_0)^2/\sigma^2\right\} & \text{if } \mu > \mu_0 \end{cases} \quad (18)$$

The parameters $\mu_0$ and $\sigma$ are adjusted to ensure that a reduction rate of outliers corresponds to the guaranteeing probability $\overline{\alpha}$:

$$\frac{\sum_{i \in I_k} w_{i,k}(\mu_0, \sigma)}{n_k} = \overline{\alpha} \quad (19)$$

where $n_k$ is the number of records associated with the hypothesis $H_k$.

The evaluation of the mean vector $m_{x,k}$ and the covariance matrix $P_{x,k}$ via Equations (13) and (14) is an iterative process in which the weights $w_{i,k}$ are updated via Equations (16)-(19). This process is repeated until convergence.

Step 2. Build a Guaranteeing Model of Concentric Ellipsoids.

The ellipsoidal model of Equations (8)-(10) acquires its guaranteeing nature after using the confidence intervals (CI) for all statistical characteristics involved and employ a minimax algorithm for calculating the "worst" combinations of those characteristics in terms of smearing the density estimates. Given the fact that the minimax algorithm is used, which "over-guarantees" the solution, the CIs can be computed via the approximate formulas, which are well verified in practice (see, e.g., Motulsky, H.; *Intuitive Biostatistics*, Oxford University Press, 1995.).

For reference, the CI-bounded estimates of the elements of the mean vector, the covariance matrix and the probability for the ellipsoidal sets are provided. For simplicity, the indices associated with the vector or matrix and the hypotheses are omitted.

The actual mean m for each element of the mean vector $m_{x,k}$ can be bounded by the following CI (see, e.g., Motulsky, H.; *Intuitive Biostatistics*, Oxford University Press, 1995.):

$$CI\{\hat{m} - z^* \hat{\sigma} \leq m \leq \hat{m} + z^* \hat{\sigma}\} \quad (20)$$

In Equation (20) three values are used to construct a confidence interval for m: the sample mean $\hat{m}$ defined by Equation (13) ($\hat{m}$ is a corresponding element of the mean vector $m_{x,k}$), the sample value of the standard deviation $\hat{\sigma}$ defined by Equation (14) ($\hat{\sigma}$ is a root-squared element of the covariance matrix $P_{x,k}$) and the value of $z^*$ ($z^*$ is the quantile of the Gaussian distribution, e.g. $z^* = 1.96$ for 95% CI).

The Monte-Carlo approach is used to account for variability of the actual covariance matrix due to finite sample. This approach is based on the use of the classical Wishart distribution as a generalization of the $\chi^2$-square distribution (see, e.g., Motulsky, H.; *Intuitive Biostatistics*, Oxford University Press, 1995.):

$$p(S) = \frac{1}{\Gamma_m(n/2) |\hat{P}|^{\frac{n}{2}}} \left(\frac{n}{2}\right)^{\frac{mn}{2}} etr\left(-\frac{n}{2} \hat{P}^{-1} S\right) |S|^{(n-m-1)/2} \quad (21)$$

In Equation (21), S is the m×m matrix argument of the distribution function, $\hat{P}$ is the estimate of the covariance matrix $P_{x,k}$ defined by Equation (14), n is the length of the sample. Also, etr denotes the exponential of the trace and $\Gamma_m(y)$ is the multivariate gamma function:

$$\Gamma_m(y) = \pi^{m(m-1)/4} \prod_{j=1}^{m} \Gamma\left(y - \frac{1}{2}(j-1)\right) \quad (22)$$

The CIs of the elements of the covariance matrix $P_{x,k}$ are computed by Monte-Carlo simulating K values of S according to the Wishart's statistics of Equation (22) and then selecting the lower and upper bounds for all elements so that they include a certain confidence percent of (e.g. 95%) of all simulated S.

The actual probability p for each ellipsoid in Equations (8)-(10) can be bounded by the following CI (see, e.g., Motulsky, H.; *Intuitive Biostatistics*, Oxford University Press, 1995.):

$$CI\left\{\hat{p} - z^* \sqrt{\frac{\hat{p}(1-\hat{p})}{n}} < p < \hat{p} + z^* \sqrt{\frac{\hat{p}(1-\hat{p})}{n}}\right\} \quad (23)$$

where $\hat{p}$ is the estimate of the probability, n is the length of the sampling set and z* is the quantile of the Gaussian distribution, e.g. z*=1.96 for 95% CI. The probability estimate is computed as $$\hat{p} = \frac{q}{n} \quad (24)$$

where n is the length of the sample and q is the number of realizations within the ellipsoid.

Figure 5:
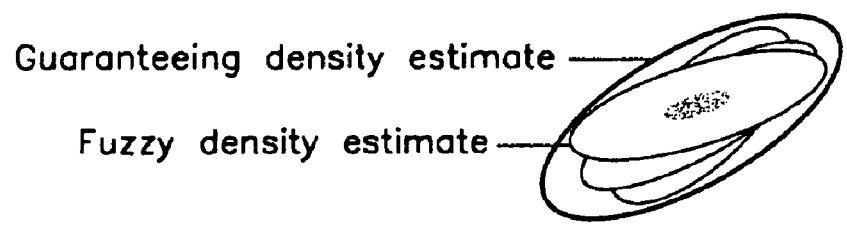
FIG. 5 is a geometric illustration of the generalized minimax approach for data analysis in accordance with the present invention.

The evaluation of the guaranteeing model of concentric ellipsoids of Equations (8)-(10) is based on the generalized minimax algorithm. See, e.g., Malyshev, V.V., Krasilshikov, M. N., and Karlov, V. I.; *Optimization of Observation and Control Processes*, ALAA Education Series, 1992, p. 349). First, this algorithm builds an equivalent uncertain-random model (a combination of random and bounded values) from the statistics of Equations (13) and (14) given the confidence intervals for their parameters as described above (see Equations (20)-(22)). Second, this algorithm expands each of the Q concentric m-dimensional ellipsoids $E_{q,k}$ of Equation (10) retaining the ellipsoid's shape and the center as defined by Equations (13) and (14). Thereby, the ellipsoid's sizes (parameter μ in Equation (10)) are minimally expended just to accommodate for the worst low boundary of the confidence interval of Equation (23) for the estimated probability $\hat{p}$ of Equation (24). The geometrical illustration of this algorithm is presented in FIG. 5, which shows how the fuzzy density estimate (fuzzy due to the non-zero confidence intervals for the covariance matrix) is approximated by a guaranteeing density estimate. It is important to note that this algorithm implicitly, via the probability estimate $\hat{p}$, accounts for the non-Gaussian nature of the densities $p(x/H_k)$, k=1, . . . , N. This is done in a guaranteeing manner, i.e. via an over-sized ellipsoid. The guaranteeing probability of each q-th ellipsoidal layer is defined by Equation (8) as a difference of the guaranteeing probabilities of the associated larger and smaller ellipsoids, respectively.

Step 3 (Optional). Identify Subspaces of Strongly Correlated Tests.

This step is especially crucial while dealing with large dimensional tests, which is typical of diagnosing inapparent diseases. The guaranteeing model of the concentric ellipsoids (Equations (8)-(10)) is defined in the full m-dimensional space of tests. However, in the real data different tests have different levels of mutual correlations. This fact is confirmed via the 2D and 3D scattering plots of clinical tests (see Section 4). For efficiency of dealing with the ellipsoidal model it is beneficial to decompose the full space S of tests into a few smaller subspaces $S_1$, . . . , $S_L$, maintaining only essential statistical dependencies. Algorithmically, the ellipsoid $E_{q,k}$ of Equation (10) is decomposed into sub-ellipsoids $[E_{q,k}]_S$, associated with a subspace $S_l$ and corresponding to the q-th layer and k-th class (hypothesis). Algorithmically, this entails identifying those combinations of tests for which it is possible to re-orient and expand the associated sub-ellipsoid $[E_{q,k}]_S$, in such a way that the following three conditions are met. First, this expanded ellipsoid includes the original ellipsoid. Second, its axes become perpendicular to the feature axes not included in the subspace $S_l$. Third, the increase in the ellipsoids volume V is within the specified threshold $\bar{v}$ (e.g. 0.05-0.1):

$$\frac{V(\bar{E}_{q,k}) - V(E_{q,k})}{V(E_{q,k})} < \bar{v} \quad (25)$$

The volume of each ellipsoid in Equation (25) is calculated as follows $$V(E) = det\{P(\bar{\mu}^2)\} \quad (26)$$

where P is the ellipsoid's matrix (a scaled covariance matrix) and $\bar{\mu}^2$ is a common parameter for both ellipsoids (initial and decomposed). The commonality of this parameter for both ellipsoids is needed in order to make the right-hand parts of Equation (10) equal while attributing the differences in $\mu^2$ to the ellipsoid's matrices.

Figure 6:
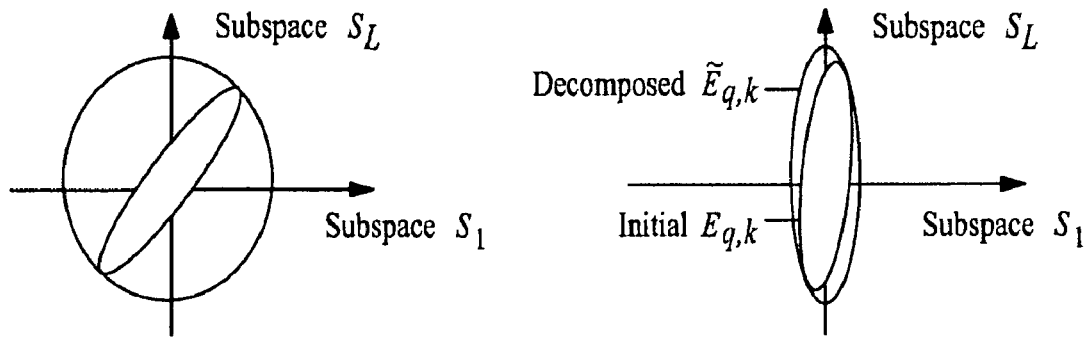
FIG. 6 is a graphical representation of decomposition into subspaces for a data set under analysis in accordance with the present invention, showing excessive decomposition on the left side of the drawing and acceptable decomposition on the right side of the drawing.

FIG. 6 shows two different examples of decomposing the space of features S into two subspaces $S_1$ and $S_L$. In the first example (left), decomposition is excessive since it is done between highly correlated subspaces. This significantly expands the final decomposed ellipsoid, i.e. increases its entropy. In the second example (right), decomposition is acceptable since the two subspaces have a low inter-correlation.

3.1.1.1.2 Generalization for Sparse (Missing) Data

In this Section the algorithm for evaluating the guaranteeing model of concentric ellipsoids (see Section 3.1.1.1.1) is generalized to the case when there are missing data points in the test matrix X (sparse matrix X). This is an important generalization aimed at increasing the overall DBA's robustness while dealing with real-world data. Indeed, in the diagnostics problems of inapparent diseases from common clinical tests one needs to deal with the fact that not each patient has a complete set of tests.

The corresponding robust algorithm to handle the missing data is a part of the iterative robust procedure of Equations (13)-(19). At the first iteration, in Equation (13) for each element of the m×1 mean vector $m_{x,k}$ the sum is taken only over those tests, which are available in the data. Similarly, in Equation (14) for each element of the m×m covariance matrix $\hat{P}_{x,k}$ the sum is taken only over those pairs of the tests that are both available in the data for a particular patient. In the case when each patient does not have a particular pair of tests, the covariance element corresponding those two sets is set to 0.

This approximate Gaussian distribution $N\{m_{x,k}, P_{x,k}\}$ obtained from Equations (13) and (14) for the entire hypothesis-conditional population (k-th class) is used for generating missing data points for each i-th patient.

Let us regroup the m×1 vector $x_{i,k}$ of all potential tests for the i-th patient of the k-th class into two consecutive blocks:

$$x_{i,k} = \begin{pmatrix} x_{i,k}^A \\ \ldots \\ x_{i,k}^M \end{pmatrix} \quad (27)$$

where $x_{i,k}^A$ is the $m^A \times 1$ vector of available tests for the i-th patient in the k-th class ("A" stands for the available data) and $x_{i,k}^M$ is the $m^M \times 1$ vector of missing tests for the i-th patient in the k-th class ("M" stands for the missing data).

Correspondingly, the first two momenta of the approximate Gaussian distribution $N\{m_{x,k}, P_{z,k}\}$ are regrouped as follows $$m_{x,k} = \begin{pmatrix} m_{x,k}^A \\ \ldots \\ m_{x,k}^M \end{pmatrix}, P_{x,k} = \begin{pmatrix} P_{x,k}^A & \vdots & P_{x,k}^{A,M} \\ \ldots & \vdots & \ldots \\ P_{x,k}^{M,A} & \vdots & P_{x,k}^M \end{pmatrix} \quad (28)$$

One can construct the following observation model for the incomplete data, which shows how the available data depend on the entire set of potential tests (available and missing) for each i-th patient:

$$x_{i,k}^A = \begin{pmatrix} I_{m^A \times m^A} & 0_{m^A \times m^M} \end{pmatrix} \begin{pmatrix} x_{i,k}^A \\ x_{i,k}^M \end{pmatrix} \quad (29)$$

Having the statistical observation model of Equations (28) and (29) it is possible to employ the conventional Bayesian approach (See, e.g., Gelb, A., ed.; *Applied Optimal Estimation*, The MIT Press, Cambridge, 1989) and calculate the a posteriori distribution $p(x_{i,k}^M/x_{i,k}^A)$, i.e. the distribution of $x_{i,k}^M$ (missing data) given the observations of $x_{i,k}^A$ (available data). Under assumption that the a priori distribution $p(x_i, \kappa^M) = N \{m_{x,k}, P_{z,k}\}$ is Gaussian and due to the fact that the observation model of Equation (29) is linear, the a posteriori distribution $p(x_{i,k}^M/x_{i,k}^A)$ will be Gaussian too. The algorithmic form of the Bayesian approach in this particular case can be expressed via the well-known Kalman Filter (See, e.g., Gelb, A., ed; *Applied Optimal Estimation*, The MIT Press, Cambridge, 1989; and Malyshev, V. V., Krasilshikov, M. N., and Karlov, V. I.; *Optimization of Observation and Control Processes*, ALAA Education Series, 1992, p. 349):

$$m_{x,k}^{M/A} = m_{x,k}^A + P_{x,k}^{M/A} \Xi_{\eta_i}^{-1}(x_{i,k}^A - m_{x,k}^A) \quad (30)$$

$$P_{x,k}^{M/A} = P_{x,k}^M - P_{x,k}^{M,A}(\Xi_{\eta_i} + P_{x,k}^A)^{-1} P_{x,k}^{A,M}.$$

where $m_{x,k}^{M/A}$ is the a posteriori $m^M \times 1$ vector of mathematical expectation for each i-th patient and $P_{x,k}^{M/A}$ is the a posteriori $m^M \times m^M$ covariance matrix for the $m^M \times 1$ vector $x_{i,k}^M$ of missing tests for each i-th patient. Also, the $m^M \times m^M$ matrix $\Xi_{\eta_1}$ is the regularization matrix. In practical problems, the matrix $\Xi_{\eta_1}$ is a covariance matrix of the additive measurement noise, associated with errors in measuring the test values in medical laboratories. When the observations are ideally precise then the elements of the matrix $\Xi_{\eta_1}$ can be set to small numbers ($\Xi_{\eta_{1 \square} p \times,k}^{A,M}$) for the regularization purpose in order to use the Kalman Filter of Equations (30).

The a posteriori distribution $p(x_{i,k}^M/x_{i,k}^A) = N\{m_{x,k}^{M/A}, P_{x,k}^{M/A}\}$ serves as a fuzzy substitute for missing data points $x_{i,k}^M$. Correspondingly, the missing value is substituted by a random generalization from the above distribution:

$$x_{i,k}^M = A\xi + m_{x,k}^{M/A} \quad (31)$$

Here, $\xi$ is a random realization of the $m^M \times 1$ standard Gaussian vector with the zero mathematical expectation and the unity covariance matrix (all diagonal elements are equal to 1 and the off-diagonal elements are equal to 0), A is the Choleski decomposition of the a posteriori covariance matrix $P_{x,k}^{M/A}$ so that $AA = P_{x,k}^{M/A}$. It should be noted that establishing the correlations between all pairs of tests facilitates a narrower spread of the values $x_{i,k}^M$.

After a new test matrix X is formed, it is used on the next iteration in the extended iterative procedure of Equations (16)-(19), Equation (30). This involves the update of the statistics $N \{m_{x,k}, P_{x,k}\}$ and, correspondingly, the a posteriori statistics $N\{m_{x,k}^{M/A}, P_{x,k}^{M/A}\}$. The updated a posteriori statistics are used via Equation (31) for generating new realizations of the missing data points in the test matrix X for Equations (13) and (14).

3.1.1.1.3 Generalization for Multiple-Set Densities

The Gaussian-like approximation of the global density in a form of guaranteeing concentric ellipsoids (see Section 3.1.1.1) can be generalized to its multiple-set version. This generalization is useful in the cases when the hypothesis-conditional density $p(x/H_k), k=1, \ldots, N$ can be thought as a set of different Gaussian-like densities. The multiple-set density can be formalized via a convolution $$p(x/H_k) = \sum_{j=1}^{J} \rho_j(x/H_k) p_j(x/H_k) \quad (32)$$

where the hypothesis-conditional density $p_j(x/H_k)$ is associated with the j-th set and $\rho_j(x/H_k)$ is a probabilistic measure governing (stochastically) a choice of the j-th set.

A practical approach to constructing the multiple-set model of Equation (32) is based on cluster analysis. In this particular case samples (patients) are clustered in each k-th class (diagnosis) in an attempt to identify L most separated clusters in the space of features (tests). When these clusters are reasonably separated one can split a space of features x in J regions $\Omega_{j,k}$, $j=1, \ldots, J$ associated with each cluster. The boundaries of the regions $\Omega_{j,k}$, $j=1, \ldots, J$ can be chosen in an ellipsoidal form similar to Equation (10) given the mean vector and the covariance matrix for x in each j-th set.

The choice of the probabilistic measure $\rho_j(x/H_k)$ can be the following:

$$\rho_j(x/H_k) = \alpha \frac{d_j}{\sum_{j=1}^{J} d_j} \quad (33)$$

where $$d_j = [(x - m_{xj})^T (x - m_{xj})]^{\frac{1}{2}}$$

is the distance from a particular x point to the center of the region $\Omega_{j,k}$, $j=1, \ldots, J$. Also, in Equation (33), $\alpha$ is a scalar which normalizes the density $p(x/H_k)$:

$$\int_{x \in R^m} p(x/H_k) dx = 1.$$

Figure 7:
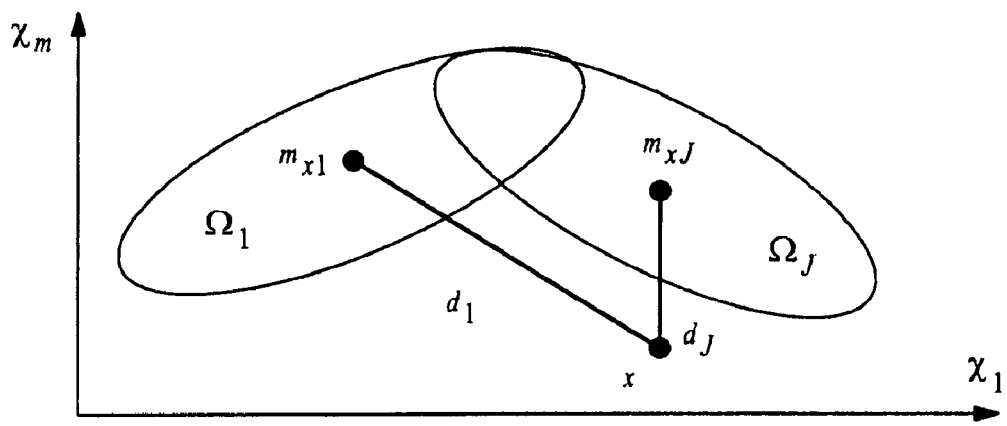
FIG. 7 is a geometrical illustration of the multiple-set density analysis performed on data, in accordance with the invention.

Geometrical illustration of the multiple-set density is provided in FIG. 7.

3.1.1.2 Local Estimation of Density in the DBA

From a practical point of view (medical diagnostics), the important element of the DBA for interpreting the "local" aspect of the density estimation involves a statistical generalization of the threshold principle currently used in medical practice for diagnostics. According to this principle the "hard" test values are established (e.g. by the World Health Organization or other medical associations) for the use as thresholds in detecting a certain disease. The key advantage of the statistical generalization consists in the fact that the DBA uses a system of "soft thresholds" and, thus, detects a more complex hidden pattern of a disease in the space of multiple tests. The search for these patterns is localized around the "hard thresholds", i.e. in the regions where the accurate diagnostics are critical.

From a mathematical point of view, the DBA for local density estimation presents a principally different method compared with the state-of-the-art methods, e.g. K-nearest neighbor method or kernel methods. (See for example, Webb, A.; *Statistical Pattern Recognition*, Oxford University Press, 1999). Three major innovations of the DBA for estimating density locally are the following:

1) Soft thresholds for diagnostics
2) Definition of neighborhood in the space of critical distances to thresholds and
3) Statistical discrete patterns of neighbor counting.

Figure 8:
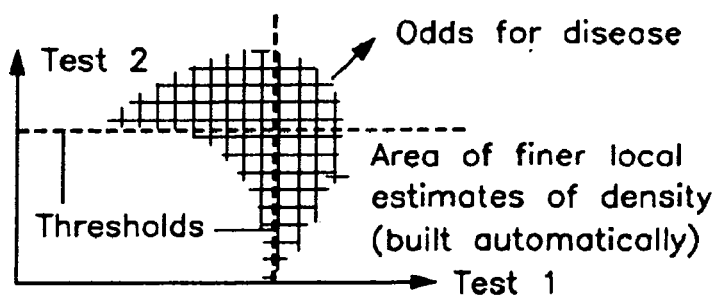
FIG. 8 is a graphical representation of the concept of soft thresholds in diagnostics.

FIG. 8 presents a general idea of the concept of soft thresholds, which is formalized via a novel way of estimating density locally. In other words, a probabilistic measure around the hard thresholds is defined in order to better formalize the statistical nature of the odds for a particular disease.

The local estimation of density entails computing a distance from the vector of tests for a new patient $x_{new}$ to the vector of tests for his or her neighbors $x_{i,k}$ where i counts diagnosed patients and k identifies a diagnosis (class). The global density estimation (see Section 3.1.1.1) provides important reference information for the local density estimation. This is due to the knowledge of statistical dependencies between the tests, which are estimated globally and are formalized in the form of a guaranteeing model of concentric ellipsoids represented by Equations (8)-(10). This knowledge contributes to a better definition of distance between the data points in the local area.

This distance is defined between $x_{new}$ and $x_{i,k}$ as follows $$d_{i,k} = (x_{new} - x_{i,k})^T P_{x,k}^{-1} (x_{new} - x_{i,k}) \quad (34)$$

where $P_{x,k}$ is the m×m covariance matrix for the k-th class. This matrix globally (i.e. using the global estimate of density on the entire data in the class) transforms the distance space in such a way that the distance between neighbors accounts for the observed correlations in the test values (for the given class).

The latter fact is not difficult to prove. First, the space of features $x_k$ can be transformed into an uncorrelated set of features $z_k$ (for each class):

$$z_k = A_k^{-1}(x_k - m_{x,k}) \quad (35)$$

where $m_{x,k}$ is the m×1 mean vector for the k-th class and A is the Choleski decomposition of the covariance matrix $P_{x,k}$ so that $A_k A_j^T = P_{x,k}$. Second, in the transformed space of the uncorrelated features $z_k$, the distance $d_{i,k}$ can be expressed in a form, invariant to the mean vector $m_{x,k}$, and this directly leads to Equation (34):

$$d_{i,k} = \|z_{new} - z_{i,k}\|^2 = (z_{new} - z_{i,k})^T(z_{new} - z_{i,k}) = \|A_k^{-1}(x_{new} - m_{x,k}) - A_k^{-1}(x_{i,k} - m_{x,k})\|^2 = \|A_k^{-1}(x_{new} - x_{i,k})\|^2 = (x_{new} - x_{i,k})^T [A_k A_k^T]^{-1}(x_{new} - x_{i,k}) = (x_{new} - x_{i,k})^T P_{x,k}^{-1}(x_{new} - x_{i,k}) \quad (36)$$

Figure 9:
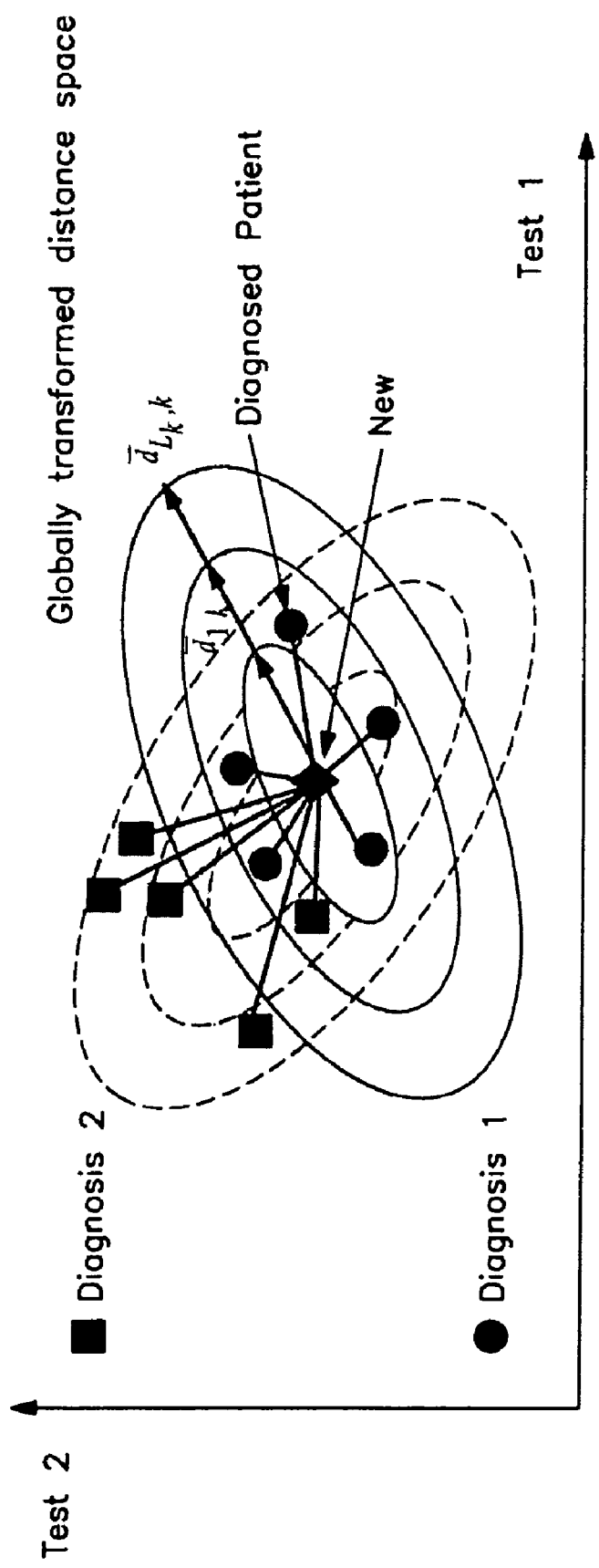
FIG. 9 is a graphical representation of the definition of globally-transformed distance in local density estimation.

FIG. 9 illustrates the transformation of a local distance space around a new patient, given the global estimates of density. Two diagnoses (classes) and two tests are shown. The ellipsoidal contour lines indicate how the tests are inter-dependent in each class. A sequence $\{d_{l,k}\}$, l=1, ..., $L_k$ discretizes the transformed distance space in layers for each k-th class. The layers ($\bar{d}_{l-1,k}, \bar{d}_{l,k}$], l=1, ..., k are the parameters that define the DBA algorithm for local density estimation.

3.1.1.2.1 A Simpler Form of the Neighbor Counting Pattern

The key element of the local density estimation is a statistical discrete neighbor counting pattern. This is a non-parametric representation of the local density in the contrast with the parametric (ellipsoidal) representation of the global density in Section 3.1.1.1. The neighbor counting pattern is defined in a form of counting neighbors in the distance layers for each class: $\{C_{l,k}\}$, l=1, ..., $L_k$. The integer $C_{l,k}$ is the number of patients diagnosed with the k-th diagnosis whose tests are distanced from the new patient's tests within the k-th globally-transformed distance layer for the k-th class:

$$C_{l,k} = \sum_i^{n_k} \vartheta_{l,i,k}, \; \vartheta_{l,i,k} = \begin{cases} 1 & \text{if } \bar{d}_{l-1,k} < d_{i,k} \leq \bar{d}_{l,k}, \bar{d}_{o,k} = 0 \\ 0 & \text{otherwise} \end{cases} \quad (37)$$

where $n_k$ is the total number of patients in the k-th class (selected for training) and the index i runs over all these patients.

Figure 10A:
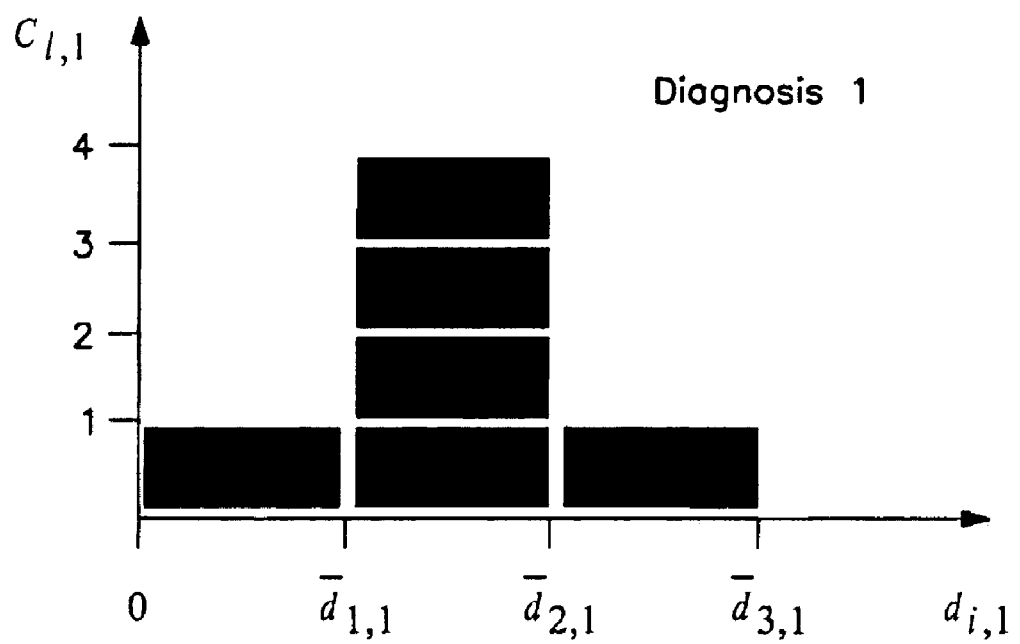
FIGS. 10A-10B are geometrical illustrations of the neighbor counting patterns for two diagnoses.
Figure 10B:
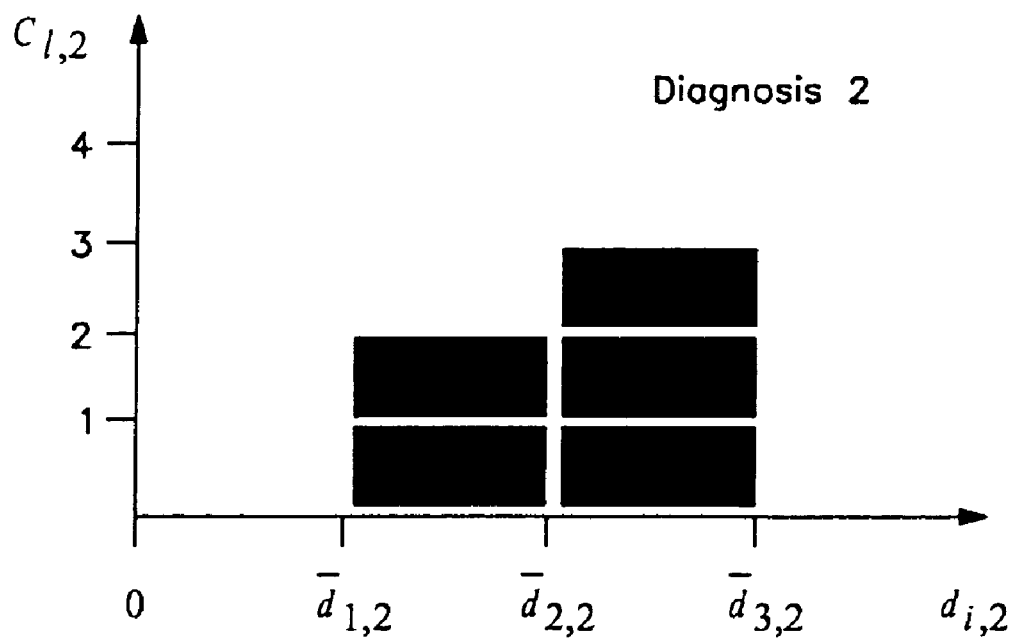

FIGS. 10A-10B show a geometrical illustration of the neighbor counting patterns for two diagnoses (Diagnoses 1 and Diagnosis 2). Note that these patterns exactly correspond to FIG. 9.

Using Equation (37) with Equation (34), one can generate the observed discrete neighbor counting patterns for any new patient whose test values are $x_{new}$. As FIGS. 10A-10B illustrate, these patterns are generated for each k-th class (diagnosis) and each l-th layer of the class-dependent distance of Equation (34). The discrete neighbor counting patterns can be viewed as a new transformed set of features, introduced to handle local aspects of the classification problem. This is a much more sophisticated pattern than counting up to the first K nearest neighbors in the K-nearest neighbor method (see Webb, A.; *Statistical Pattern Recognition*, Oxford University Press, 1999). and then using a simple voting procedure for classification.

The DBA uses a neighbor counting pattern to estimate (locally) the hypothesis-conditional densities $p(x | H_k)$, k=1, ..., N, i.e. it has a rigorous statistical framework. The local statistical estimation of the density involves determining probabilistic measure on the discrete neighbor counting patterns ($C_{l,k}$), l=1, ..., $L_k$, k=1, ..., N. Let us define the 3D probability sets (tensors) on all possible local counts of neighbors in Equation (38):

$$p_{s,l,k} = \Pr\{\bar{c}_{s,l,k}; c_{s-1,l,j} < C_{l,k} \leq \bar{c}_{s,l,k}\}; s=1, \ldots, S_{l,k}; l=1, \ldots, N \quad (38)$$

In Equation (38), $p_{s,l,k}$ is the local probability of the event that the count of neighbors within the l-th globally-transformed distance layer for the k-th class belongs to the interval ($\bar{c}_{s-1,l,k}, \bar{c}_{s,l,k}$] where the $\bar{c}_{s-1,l,k}$ and $\bar{c}s,l,k$ are the integer parameters (in a general case different for the distance's layer and the class) and $\bar{c}_{0,l,k} = 0$. The choice of these parameters depends on how many data points are available in order to use a finer neighbor counting pattern.

The estimates for the probability sets $p_{s,l,k}$ of Equation (38) can be obtained via the frequency calculations, sequentially considering each data point in the k-th class as a "new" point with respect to which the discrete neighbor counting pattern $\{C_{l,k}\}$, l=1, ..., $L_k$=1, ..., N is derived using Equation (37). There will be $n_k$ samples of these patterns in each k-th class and these samples can be denoted as $\{C_{l,i,k}\}$, i=1, ..., $n_k$ for the l-th globally-transformed distance layer and the k-th class. The estimate of the local probability $p_{s,l,k}$ in this case is defined as a frequency $$\hat{p}_{s,l,k} = \frac{\sum_{i=1}^{n_k} \vartheta_{l,i,k} \chi_{s,l,i,k}}{n_k} \quad (39)$$

where, like in Equation (37), $1_{l,i,k}$ is an indicator that the i-th patient's tests are within the l-th globally-transformed distance layer for the k-th class;

$$\vartheta_{l,i,k} = \begin{cases} 1 & \text{if } \overline{d}_{l-1,k} < d_{l,k} \le \overline{d}_{l,k}, \overline{d}_{0,k} = 0 \\ 0 & \text{otherwise} \end{cases} \quad (40)$$

and $\chi_{s,l,i,k}$ is an indicator that the neighbor counting number $C_{l,i,k}$ is within the s-th interval:

$$\chi_{s,l,i,k} = \begin{cases} 1 & \text{if } \overline{c}_{s-1,l,k} < C_{l,i,k} \le \overline{c}_{s,l,k}, \overline{c}_{0,l,k} = 0 \\ 0 & \text{otherwise} \end{cases} \quad (41)$$

In Equation (39), $n_k$ is the number of patients in the k-th class (from those patients which are selected for training).

The local estimate of the hypothesis-conditional densities $p(x/H_k), k=1, \ldots, N$ is calculated as a value proportional to the probability of the event that an observed vector of tests x and the associated discrete neighbor counting pattern $\{C_{i,k}(x)\}$, $l=1, \ldots, L_k$, $k=1, \ldots, N$ defined via Equation (37) could be actually observed.

This probability can be computed as a multiplication of the probabilities for the event that in each l-th globally-transformed distance layer the neighbor counting pattern falls into certain counting intervals $(\overline{c}_{s-1,i,k}, \overline{c}_{s,i,k}]$ which index s depends on x:

$$\hat{p}_{loc}(x/H_k) = \prod_{l=1}^{L} \hat{p}_{s(x),l,k}, k = 1, \ldots, N \quad (42)$$

Multiplication of probabilities in Equation (42) entails the statistical independence between neighbor-counting variables. This independence is facilitated by de-correlation of the space of clinical tests in the global estimate for the hypothesis-dependent density by using a distance definition of Equation (34) for counting neighbors.

3.1.1.2.2 A More Complex Form of the Neighbor Counting Pattern

The local density estimate of Equation (42) by itself has a power to discriminate between different classes (hypotheses). However, this discrimination is averaged over all patients in the class and, thus, is smeared. The discrimination power can be sharpened via a split of all patients of the k-th class with respect to the critical distance from the test values to the hard threshold associated with each clinical test. This critical distance can be defined in different ways including a vector representation of this distance (e.g., for different subsets of clinical tests).

Let us define for each k-th class the two critical distances from any point of clinical tests x (e.g., $x_{new}$) to the threshold t, assuming that the values of the clinical tests are normalized and can be compared:

$$\overline{r} = [(x-t)^T P_{x,k}^{-1}(x-t)]_{\overline{J}}, \overline{J} = \{j : \kappa_j x_j \ge \kappa_j t_j\} \quad (43)$$

$$\underline{r} = [(x-t)^T P_{x,k}^{-1}(x-t)]_{\underline{J}}, \underline{J} = \{j : \kappa_j x_j \ge \kappa_j t_j\} \quad (44)$$

Note that in Equations (43) and (44) the critical distances are computed for two different subsets of features (clinical tests) and the correlations between the tests in each subset $\overline{J}$ and $\underline{J}$ is accounted for. The scalar $\kappa_j$ formalizes the two different situations in defining the subsets $\overline{J}$ and $\underline{J}$: 1) if $\kappa_j=1$ then the j-th clinical test indicates a disease when the value $x_j$ is above the threshold $t_j$; and, 2) if $\kappa_j=-1$ then the j-th clinical test indicates a disease when the value $x_j$ is below the threshold $t_j$. Correspondingly, a larger critical distance $\overline{r}$ is the more odds for a disease a patient with the observation x has, and vice versa. Also, a larger critical distance $\underline{r}$ is the more odds for a non-disease state a patient with the observation x has, and vice versa.

A combination of $\overline{r}$ and $\underline{r}$ can be converted to a relative critical distance $$\theta = \overline{r}/\underline{r} \quad (45)$$

which formalizes a soft threshold and is implicitly used in the prediction mechanism. In this case all patients in the k-th class are split in a few groups associated with the discrete intervals for $\theta$: $(\overline{\theta}_{v-1,k}, \overline{\theta}_{v,k}], v=1, \ldots, V_k$.

This additional splitting leads to generalization of the discrete neighbor counting pattern presented in Equation (37). This more general neighbor counting pattern is defined in a form of counting neighbors in the distance layers (both for the patient-patient and the patient-threshold distances) for each class:

$\{C_{v,l,k}\}, v=1, \ldots, V_{l,k}, l=1, \ldots, L_k$. The integer $C_{v,i,k}$ is the number of patients diagnosed with the k-th diagnosis whose tests are distanced from the new patient's tests within the l-th globally-transformed distance layer for the k-th class and are distanced from the hard threshold within the v-th layer of the critical distances for the k-th class:

$$C_{v,l,k} = \sum_{i}^{n_k} \vartheta_{l,i,k} \xi_{v,i,k}. \quad (46)$$

where $n_k$ is the total number of patients in the k-th class (selected for training) and the index i runs over all these patients. In Equation (46), the indicator $\theta_{l,i,k}$ was already introduced in Equation (37) and is repeated for reference in Equation (40). The second indicator in Equation (46), $\xi_{v,i,k}$, is new and it indicates whether the i-th patient's tests are within the v-th interval of the critical distance $\theta$ for the k-th class:

$$\xi_{v,i,k} = \begin{cases} 1 & \text{if } \overline{\theta}_{v-1,k} < \theta_{v,i,k} \le \overline{\theta}_{v,k}, \overline{\theta}_{0,k} = 0 \\ 0 & \text{otherwise} \end{cases} \quad (47)$$

Given a more complex neighbor counting pattern of Equation (46), the 3D probability sets $p_{s,l,k}$ of Equation (38) are generalized to the 4D probability sets $p_{v,s,l,k}$:

$$p_{v,s,l,k} = \Pr\{C_{v,s,l,k} : \overline{c}_{v,s-1,l,k} < C_{v,j,k} \le \overline{c}_{v,s,l,k}\}; v=1, \ldots, V_{l,k}; s=1, \ldots, S_{l,k}; l=1, \ldots, L_k; k=1, \ldots, N \quad (48)$$

In Equation (48), $p_{v,s,l,k}$ is the local probability of the event that the count of neighbors within the l-th globally-transformed distance layer and the v-th layer of critical distances for the k-th class belongs to the interval $(\overline{c}_{v,s-1,l,k}, \overline{c}_{v,s,l,k}]$ where the $\overline{c}_{v,s-1,l,k}$ and $\overline{c}_{v,s,l,k}$ are the integer parameters (in a general case different for the distance's layer and the class) and $\overline{c}_{v,0,l,k}=0$.

Correspondingly, the estimates of the probabilities $p_{v,s,l,k}$ in Equation (48) are defined similarly to Equation (39):

$$\hat{p}_{v,s,l,k} = \frac{\sum_{i=1}^{n_k} \vartheta_{l,i,k} \chi_{s,l,i,k} \xi_{v,i,k}}{n_k} \quad (49)$$

where all indicators $\Theta_{l,i,k}$, $\chi_{s,l,i,k}$ and $\xi_{v,i,k}$ were described above in Equations (40), (41) and (47).

Let us now connect the probability estimates of Equation (49) to the local density estimation. For the observed x one can compute the indices $s=s(x)$ and $v=v(x)$. Thereby, the index $s(x)$ is determined in the way similar to that of Section 3.1.1.2.1 and the index $v(x)$ is determined via computing the critical distances and identifying the matching interval of $\theta$. As a result, of this index determination, the local density estimate of Equation (42) is generalized to the following form:

$$\hat{p}_{loc}(x/H_k) = \prod_{l=1}^{L} \hat{p}_{v(x),s(x),l,k}, k = 1, \ldots, N \quad (50)$$

Note that justification for simply multiplying the probabilities in Equation (50) are the same as for Equation (42).

It is important to emphasize that due to the fact that only a finite set of patients is available for training the DBA algorithm, the ability to split the data points with respect to distance layers and critical distances is limited. Therefore, the choice of the splitting parameters $(d_{l-1,k}, d_{l,k}), l=1, \ldots, L_k$, $(\theta_{v-1,k}, \theta_{v,k}], v=1, \ldots, V_k$ as well as the choice of the counting intervals $(\bar{c}_{v,s-1,l,k}, \bar{c}_{v,s,l,k}] \ldots S_{l,k}$ should account for this fact, given the volume of the available data. In conjunction with this fact, the following should be noted. The measurement noise in the test values helps to make the neighbor counting patterns more stable statistically. This paradox is explained by the following. When a data point (a vector of test values) is uncertain due to noise, then it can be represented by multiple points that sample all possible space. This sampling can be done either via Monte-Carlo or via the convolution integrals. In other words, the sampling increases the number of data points used for computing the discrete neighbor counting patterns. This procedure is known as a regularization procedure and can be used, for example, for the Kalman Filter (see Gelb, A., ed.; *Applied Optimal Estimation*, The MIT Press, Cambridge, 1989) when it is applied to the deterministic data. Indeed, the Kalman Filter is a statistical filter, and it cannot straightforwardly work on the deterministic data. To make the Kalman filter work for the deterministic case one needs to add so-called regularization noise with the associated covariance matrix (what was effectively done in Section 3.1.1.1.2).

3.1.1.3 Combination of Global and Local Density Estimates in the DBA

It is important to emphasize that the global (see Equation (11)) and local (see Equation (50)) estimates of the hypothesis-conditional density $p(x/H_k)$, $k=1, \ldots, N$ can be used in the DBA (see Equation (7)) independently. The global robust approximation of the density usually suffices for those patients whose test values are on the tails of distributions where diagnostics are more obvious. For those patients whose test values are in the regions closer to critical thresholds, a more accurate estimation is needed. The local estimation alone provides only some important elements (such as a non-parametric neighbor counting patterns, a soft threshold, etc.) to increase this accuracy, however it needs a guiding power of the global estimate that captures the statistical dependencies (correlations) of the clinical tests. Thus, the global and local density estimates complement each other. The local estimate corrects the global estimate while the latter helps the former in terms of capturing global statistical dependencies in the relations between neighboring data points. The DBA that uses both global and local estimates of the hypothesis-conditional PDF $p(x/H_k)$, $k=1, \ldots, N$ exhibits the best performance and yields the most accurate prediction in real practical problems.

The combination of the global and local PDF estimates can be performed via their multiplication, per Equation (51):

$$p(x/H_k) = p_{glob}(x/H_k) p_{loc}(x/H_k), k=1, \ldots, N \quad (51)$$

The rationale for using Equation (51), i.e. for assuming that the global and local hypothesis-conditional distributions of x are statistically independent, is the following. As was mentioned above the global distance transformation of Equation (34) uncorrelates the clinical tests, making the neighbor counting patterns independent from the global distribution of x at the linear (correlation) level. Although the procedure of Equation (51) works in practice and is robust to the remaining higher-order couplings between global and local distributions, it would be a matter of further improvement of the DBA to account for these higher-order effects explicitly.

3.1.2 Summary: Block-Scheme of the DBA Operations

In this Section is summarized the DBA algorithm described in details in Section 3.1.1 for the conventional diagnostics problem. The emphasis is made on the operational description of the DBA.

As shown in FIG. 3, the DBA has two major modes of operation: (1) the training mode; and (2) the prediction mode. Effectively, in the training mode the class dependent feature (multidimensional) probability density function (PDF) needs to be estimated using a training set from the data. Once this PDF is approximated, it can be used in the prediction mode straightforwardly to predict the probability of class membership for each record in the control or checking set.

3.1.2.1 The DBA Operations in the Training Mode

The key step in training the DBA is the accurate approximation of the multidimensional PDF. This can be a formidable task due to high dimensionality (10's to 100's of tests) and to uncertain, discrete and sparse data. The latter factor makes it difficult to "fuse" information from the various features (e.g., clinical tests) due to the uncertain correlations between them. The inventors have been able to successfully meet these challenges for the prediction of certain inapparent diseases using hundreds of clinical tests, as formulated in Section 3.1.1.

Figure 11:
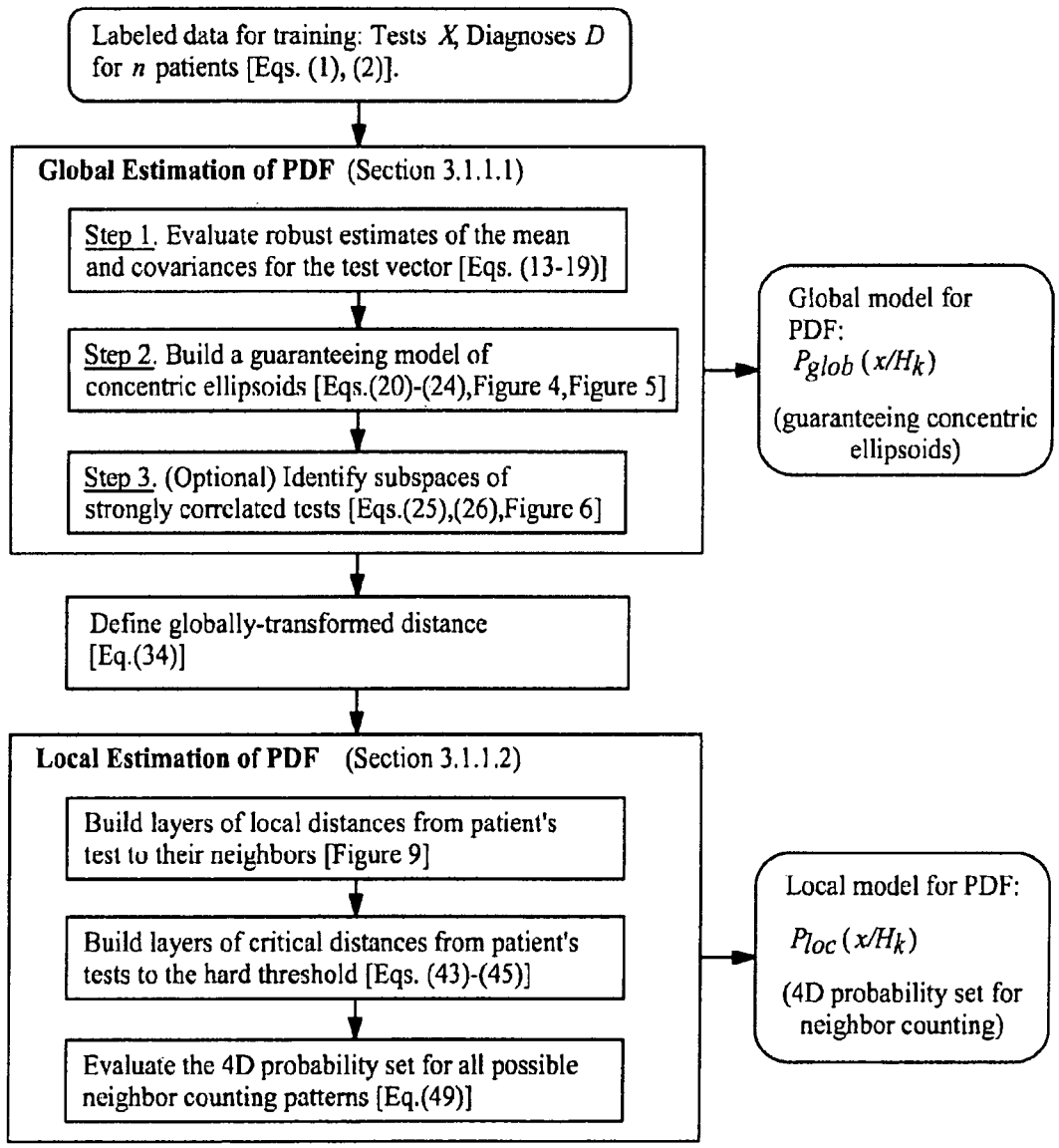
FIG. 11 is a flow diagram illustration of the Discrete Bayesian Approach (DBA) data analysis technique in accordance with the invention, in the training mode.

FIG. 11 presents a block-scheme that illustrates how the DBA operates in the training mode. The key goal of the training mode is to utilize all designated for training data points (patients with the tests and diagnosis labels) in order to develop both the global and local models for the hypothesis-dependent PDF $p(x/H_k)$. As described in Section 3.1.1.1, the global estimation of the PDF is based on the three-step procedure that evaluates the model of concentric ellipsoids in the m-dimensional space of clinical tests. This model is highly robust since it explicitly accounts for the remaining uncertainties in the estimated mean and covariance matrix of the test values. The latter fact guarantees that the data fusion process will be stable and will result into the correct estimate of the global hypothesis-dependent PDF. This global estimate provides an important guiding to the process of estimating the hypothesis-dependent PDF locally. This is done via a special definition of the distance space in Equation (34) that explicitly and robustly accounts for the global correlation between the clinical tests. The globally-transformed distance between clinical tests is the basis for the local estimation of the PDF, as described in Section 3.1.1.2. The key idea here is to employ a discrete neighbor counting pattern for local discrimination between the populations of two classes (hypotheses). To increase the discrimination power, the neighbor counting is performed in two layers that discretize the two types of distances: (1) distance from a data point associated with a patient to all neighboring data points in the globally-transformed space of clinical tests (see FIG. 9); and (2) critical distance from a data point to the hard threshold (again in the globally-transformed space of clinical tests). The neighbors are counted in the layers of these two dimensions, the counts are discretized by intervals and associated with each particular class. This makes a 4D set of all possible neighbor counting patterns. The local estimation of PDF entails evaluation of the probabilistic measure on this 4D set (see Equation (49)).

3.1.2.2 The DBA Operations in the Prediction Mode

After the DBA is trained, it can then be applied to control or checking sets, or to any new data set containing values for the features selected, in order to determine the predicted probabilities of class membership in one of the classes of interest (e.g., diseased or healthy). The corresponding predictive blocks of the DBA are also described in Section 3.1.1 along with the blocks for the training mode.

Figure 12:
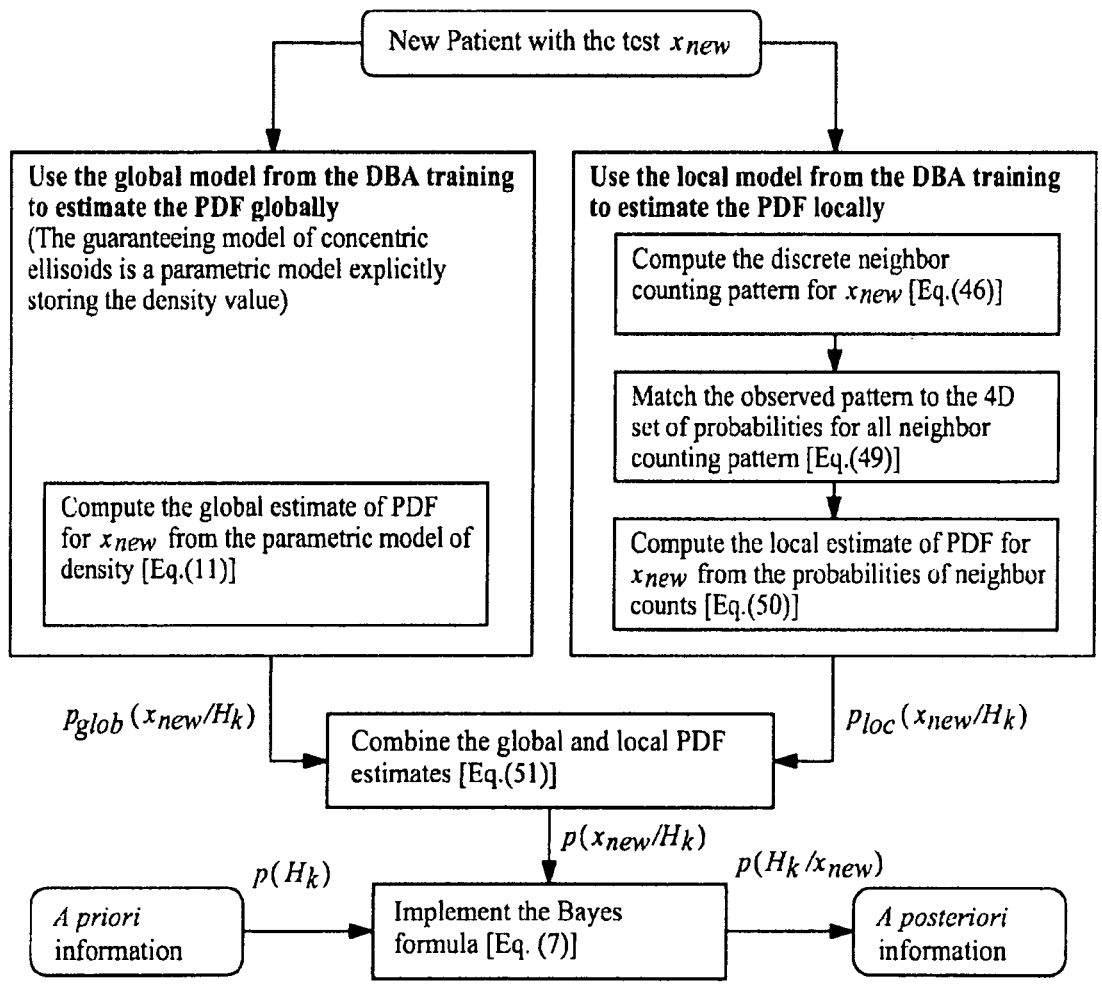
FIG. 12 is a flow diagram illustration of the DBA, in the prediction mode.

FIG. 12 presents a block-scheme that illustrates how the DBA operates in the prediction mode. The input to the DBA is a vector of the clinical tests $x_{new}$ observed for a new patient. To estimate the hypothesis-dependent PDF $p(x_{new}/H_k)$ for each k-th hypothesis (class), the DBA uses the two models (global and local) that were evaluated in the training mode. The global model is parametric and is represented by a set of robust concentric ellipsoids of Equations (20)-(24). This model straightforwardly maps the test values of the new patient, $x_{new}$, into the global hypothesis-dependent PDF $p_{glob}(x_{new}/H_k)$, k=1, ..., N (see Equation (11)). The local model involves a few computational stages as shown in FIG. 12. The goal of these computations is to derive the discrete neighbor counting pattern for the observed test values $x_{new}$ and match it to the 4D set of all possible patterns with the associated probabilistic measures (see Equation (49)). Finally, the local estimate of PDF for $x_{new}$ is computed from the probabilities of neighbor counts as presented in Equation (50). The global and local PDFs are merged via Equation (51) yielding the hypothesis-dependent PDF $p(x_{new}/H_k)$. Knowing this PDF is the key element in solving the classification problem and it is the most challenging task to obtain this knowledge. After this knowledge is obtained this immediately leads to the prediction (diagnostics) via the Bayesian formula of Equation (7):

$$p(H_k / x_{new}) = \frac{p(H_k) \cdot p(x_{new} / H_k)}{\sum_{q=1}^{N} p(H_q) p(x_{new} / H_q)}, k = 1, \ldots, N \quad (52)$$

where $p(H_k)$ are the a priori probabilities for the k-th hypothesis (class). The rule of maximum a posteriori probability:

$$\hat{H} = H_{\hat{k}}, \hat{k} = \underset{k}{\operatorname{argmax}}\, p(H_k / x_{new}), k = 1, \ldots, N \quad (53)$$

identifies the most probable diagnosis $\hat{H}$.

The decision making rule of Equation (53) is applied in conjunction with the acceptance criterion. The latter entails accepting a new patient for diagnostics or rejecting, i.e. not assigning any diagnosis due to the ambiguous a posteriori probabilities $p(H_k/x_{new})$, k=1, ..., N for that patient. The mathematical formalism is the following:

$$\text{Accepted: } \max_k p(H_k / x_{new}) \geq \bar{p} \quad (54)$$

$$\text{Rejected: } \max_k p(H_k / x_{new}) < \bar{p}$$

with the threshold $$\bar{p} \in \left[\frac{1}{N}, 1\right] \quad (55)$$

In Equation (55), N is the number of hypotheses (diagnoses). Note that if $\bar{p}=1/N$ then the patient's record is always accepted for diagnostics, and if $\bar{p}=1$ then the patient's record is accepted only if the prediction is absolutely deterministic (one of the a posteriori probabilities is equal to one). A practically important choice of the threshold $\bar{p}$ entails an intermediate situation when only a certain percent of patients is accepted for diagnostics (actually diagnosed) and it is expected that for this group of patients predicting the right diagnosis has a higher probability. Section 4 illustrates how the DBA's acceptance mechanism works in practice for diagnostics of colon and ovarian cancer from common clinical tests. In general, this acceptance mechanism is extremely useful for the diagnostics of inapparent diseases, which actually paves the way for a new concept of selective diagnostics. It is important to mention that this concept is very similar to that underlying the pharmagenomic ideas to developing drugs, which target only particular groups of people.

3.1.3 Recursive Nature of the DBA

The DBA utilizes an important practical property of the Bayesian estimation to integrate (fuse) information recursively. Let us assume that a new patient previously acquired a set of clinical tests $x_{prev}$ and the corresponding a posteriori probabilities $p(H_k/x_{prev})$ were evaluated by the DBA in the predictive mode. After this event a next set of clinical tests $x_{next}$ became available, which is statistically independent from the previous set of tests. In this case, the recursive mechanism of the DBA allows for interpreting the a posteriori information $p(H_k/x_{prev})$ as "new" a priori information: $p(H_k/x_{prev}) \rightarrow p(H_k)$. Correspondingly, the DBA is trained and then used in a predictive mode only for a subset of the clinical tests $x_{next}$, thus, generating the updated a posteriori probabilities over hypotheses (diagnoses):

$$p(H_k / x_{next}, x_{prev}) = p(H_k / x_{prev}) \cdot \frac{p(x_{next} / H_k)}{\sum_{q=1}^{N} p(H_q / x_{prev}) p(x_{next} / H_q)}, \quad (56)$$

$$k = 1, \ldots, N.$$

This recursive property allows for developing a highly efficient (both in terms of memory and speed) automated system for medical diagnostics. For an initial estimate of $p(H_k)$, the DBA can use by default a uniform pdf over the set of possible hypotheses. Thereafter, the recursive processing described above can be performed.

3.2 The DBA for Solving Structured Diagnostics Problem (Custom Innovations)

The DBA described herein offers unique customization to the diagnostics problem in addition to the core capability described in Section 3.1. In this Section is itemized a few possible customizations typical for diagnosing inapparent diseases from common clinical tests.

3.2.1 Handling Multiple Diagnoses

The DBA for the conventional diagnostics problem (see Section 3.1) straightforwardly handles the multiple diseases since it is a multi-hypotheses classification algorithm. However, a generation of the a posteriori probabilities over the list of possible candidate hypotheses (diagnoses) is only a first step. In this Section, it is emphasized that the customized DBA provides the output in a more elaborate practical format such as the a posteriori tree of diagnoses and can handle overlaps in the diseases (not-mutually exclusive hypotheses).

3.2.1.1 Generating a Posteriori Tree of Diagnoses

A practical algorithm for generating the a posteriori tree of diagnoses is provided by the following. First, for the specified set of clinical tests the algorithm performs discrimination between each two-candidate hypotheses (diagnoses) from a specified list of N diagnoses. As a result, a N×N matrix of pair-wise discriminations is evaluated. This matrix serves as a "distance matrix" for hierarchical clustering which generates the hierarchical tree of diagnoses. In particular, this tree provides clusters of similar diseases. Second, the DBA runs for all possible levels of the tree and associated hypotheses in order to evaluate the αposteriori probabilities over these hypotheses. As a result of this two step procedure the a posteriori tree of diagnoses is generated with the computed a posteriori probabilities to characterize the likelihood of each cluster of diseases or a particular disease.

In a practical application, the DBA generates an individual a posteriori tree of possible diagnoses for each patient using his or her clinical tests. The particular characteristics of this tree (hierarchy of clusters/diseases and associated a posteriori probabilities) will define how this tree is detailed. Here the important point is that the DBA can indicate to which "acceptance group" each patient belongs. For example, for 50% of patients the DBA could provide a coarse tree of possible diagnoses. But, for 20% the tree can be more detailed. It is expected that related diseases (e.g. colon cancer, ovarian cancer, breast cancer and other cancers) can make a cluster in a coarse tree of possible diagnoses. If this cluster has a large probability then more specific clinical tests (possibly not only from CBS and Chemical Screen tests) could be suggested for a particular patient, in order to better discriminate between different cancers.

3.2.1.2 Combinations of Diseases

The a posteriori trees of diagnoses generated for a large number of patients (individually) can provide an estimate how different diseases combine, i.e. how often they come together in the same cluster of diseases. Additional information from multiple diagnosis codes for some patients in the Quest database (e.g. that the diabetes patient has a second diagnosis—hypertension) will help to better define a set of hypotheses expanding it by combined diagnoses. One might expect that e.g. "diabetes", "hypertension", "diabetes+hypertension" classes will be clustered together at some level of the hierarchical a posteriori tree of diagnoses but there could be some clinical tests probabilistically discriminating the three classes at a finer level. The proposed approach to estimating the disease overlaps is purely based on the data, i.e. on the analysis of the tests-diseases relations. Therefore the estimates depend on the clinical tests selected (theoretically, given all existing tests the DBA would indicate to what extent diseases can be discriminated between each other). Any additional medical information and knowledge (e.g. that one patient often has both diabetes and hypertension) can refine the model of disease combinations.

The model of disease combinations can be incorporated into the DBA for diagnosing new patients via the so-called Bayesian nets formalism. One can think about the latter as a generalization of a hidden Markov chain model with transition probabilities between possible groupings of diagnoses. Mathematically, this involves the use of two lists of diseases (hypotheses). The first list $H^* = \{H_1^*, H_2^*, \ldots, H_N^*\}$ is an "actual" list of diagnosis labels already assigned by doctors (including the multiple labels for a single patient). The second list $H = \{H_1, H_2, \ldots, H_N\}$ is a hidden list of diagnoses, which is not observed, but which will be used for assigning new labels. The use of these two lists is a purely mathematical technique. In the conventional diagnostics problem there would be one-to-one correspondence of the lists: $H = H^*$. In the structured diagnostics problem, the probabilistic (not one-to-one correspondence) between the two lists helps to model disease combinations and, thus, handle multiple diagnoses as non-exclusive hypotheses.

The Bayesian net in its simplest form (hidden Markov chain) is represented by the following matrix equation:

$$p(H^*) = Q p(H) \tag{57}$$

where Q is the N×N matrix of transition probabilities between the elements (hypotheses) from the two lists, $p(\cdot)$ is the probabilistic measure over hypotheses. As was discussed above, the matrix Q can be estimated from the a posteriori probabilities generated for a large number of patients. More complex forms of the Bayesian net will involve a particular topology of relations between the clusters of diseases identified by the a posteriori trees of diagnoses.

The DBA for this type of the structured diagnostics problem will perform classification in the space of hidden hypotheses $H = \{H_1, H_2, \ldots, H_N\}$. The probabilistic model of Equation (57) (or its more general form) will be used in the estimation of the hypothesis-dependent PDF $p(x/H_k)$, $k = 1, \ldots, N$. In the prediction mode the DBA will generate the a posteriori tree of diagnosis that will indicate which disease or multiple diseases a patient might have. It should be emphasized that the DBA as a data mining tool can only indicate to what extent the space of possible diagnoses (given the observed clinical tests) is discriminated. But, the DBA cannot interpret if the cluster of diseases is an actual combination of diseases acquired by a patient or limitation of discrimination. Only doctors can interpret this situation given the useful inputs from the DBA. But, in its turn, the DBA can optimally identify additional tests which statistically have the best potential to improve discrimination within a cluster of diseases.

3.2.2 Planning Clinical Tests

Given the DBA's power to handle multiple diagnoses and eventually output the diagnostics results in the form of the a posteriori tree of diagnoses (see Section 3.2.1), it is possible to develop an automated expert system for effective planning of clinical tests for patients. This system would advise the physicians on which tests each patient needs to take in order to increase the reliability of the diagnostics (multiple diseases).

The key strategy for planning clinical tests in the multiple-disease diagnostics by the DBA is the use of the differential patterns of diseases. These differential patterns show how any pair of diagnoses differs statistically in the multi-dimensional space of clinical tests. There is one or another test, which tells the difference between two diseases (in a probabilistic sense).

Increasing the number of clinical tests will facilitate the discrimination in the space of multiple hypotheses (diagnoses). One can imagine a three-dimensional m×N×N tensor (where n is the number of clinical tests and N is the number of possible diagnoses). This is an enormous "iceberg" of information, which the multiple-diagnosis DBA will effectively utilize.

The practical goal of this automated system for planning clinical tests will be to optimize the testing path in diagnostics via identifying at each step the new tests, which will increase the probability of the acceptance and success rates in predicting particular diagnoses (thus, making the a posteriori tree of diagnoses finer but concentrating on particular clusters, e.g. clusters associated with different forms of cancer as was described above). This system will be especially useful at earlier stages of diagnostics since it will cut cost and time of clinical tests needed for each particular patient.

This system could evolve into a powerful automated alternative to the decision trees (not to be confused with the a posteriori tree of diagnoses) currently used in diagnostics. Indeed, the decision tree systems are based on setting particular thresholds for values of clinical tests. In reality those thresholds are rather "fuzzy" and inter-dependent. The DBA captures those realities in a statistical way including the inter-dependencies and the differential statistical patterns between diseases. Moreover, the DBA does not prescribe a particular flow of tests (as it is done in a conventional decision trees), it suggests what tests would be optimal given the tests which are already available.

3.2.3 Capturing Various Trends In The Data

As formalized in Section 2.2 in real diagnostics problem there are different factors, which affect the clinical tests. Equation (5) clearly distinguishes two types of factors. First, the discrete (e.g. binary) factor $\phi$ that represents, for example, sex or race of a patient or a type of medical treatment. Second, the continuous factor $\theta$ that represents, for example, the patient's age (DOB) or the height/weight index. As our experience with the Quest clinical data shows, it is imperative to account for the discrete factor $\phi$ such as patient's sex by splitting the data into two groups. Correspondingly, the DBA predictor is derived independently (trained and checked) for each of these two groups.

The factor $\theta$ (e.g., age) is a more complex factor due to its continuity. Our analysis on the Quest data shows (see Section 4) that for many tests there is a strong trend of changing the test values with age. Therefore, accounting for this trend is also very important for designing a high-precision DBA predictor. Our experience with the Quest data shows that correct capturing of trends is even a more important contributor to the accurate prediction than the design of accurate classifier itself in the framework of the conventional diagnostics problem. This is additional proof that the ability of the DBA to be customized to the particularities of the structured problem of diagnostics is the key in achieving the highest accuracy of diagnosing inapparent diseases from common clinical tests.

The simplest way of accounting for the trends in the data would be to split the data into a number of windows. For example, one could generate a few age windows or a few windows for the height/weight index. Correspondingly, an individual DBA would be derived for each window. However, this multi-channel DBA is difficult to develop due to the lack of statistical data. First, many splits of data are needed (in age intervals, in height/weight index, in sex, in race, in training/checking modes etc.). Second, due to the sparsity of data (not each patient has a complete set of clinical (tests) the actual volume of the data becomes even lower. Third, the fact that the DBA should operate as a multi-diagnosis predictor will require even a large amount of all records in order to have the representative statistics for the low-prevalence diseases (e.g., cancer).

The DBA provides an efficient way of accounting for the trends in the data without splitting the data with respect to the continuous factor q (e.g., age). This is done via Markov chain models derived from the statistical data. For example, those clinical tests, which significantly change with patient's age, the Markov chain model can capture the trend (statistically) and propagate the distributions between different age groups. In this case the "remote" age groups for each patient will be fused into the diagnostics process but with a lesser weight. This technique allows for using statistics from a broader age window or from all records. This is also applied to other factors q (e.g. height/weight index).

Equation (58) presents a Markov chain model for capturing the trends in the data (e.g., age) for the j-th clinical test:

$$p[x_j(q+Dq)] = Q(q,Dq)p[x_j(q)], i=1,\ldots,m \quad (58)$$

Here, $Q(q,Dq)$ is the $N_x \times N_x$ matrix of transitional probabilities depending on the factor q (e.g. age) and the difference Dq, $N_x$ is the number of discretization intervals for the test value $x_j$. Note that different Q matrices are derived on a set of the discretized values of q and Dq. The method for deriving the matrices Q is statistical and is based on the two steps. The first step consists of estimating two histograms that are the frequency representations of the two PDFs: $p[x_j(q+Dq)]$ and $p[x_j(q)]$. The second step is selecting the matrix Q that satisfies Equation (58) in the least-squares sense. Note, that in order to limit the choice of Q one can represent it in a form of a sparse matrix with a diagonal Gaussian band.

From a practical point of view, it is important to present a special case of the Markov chain model of Equation (58) in a form of a Markov process formalized by a stochastic linear differential equation.

$$\frac{\partial x(q, Dq)}{\partial Dq} = A(q) \times (q, Dq) + B(q) + (Dq) \quad (59)$$

where the m×m matrix A (q) formalizes the rates of the averaged trend in the clinical tests with respect to the factor q (e.g., age) and the m×m matrix B (q) is the associated diffusion matrix. It is assumed that x (Dq) is a standard white Gaussian process with the zero mean and the unity covariance matrix. Note that it is also assumed that Markov process is statistically stationary in a broad window of each q.

The ensemble of x generated by Equation (59) can be represented by the first two momenta (mathematical expectation and covariance matrix, for which see, for example, Gelb, A., ed.; Applied Optimal Estimation, The MIT Press, Cambridge, Mass., USA, 1989):

$$\frac{\partial m_x(q, Dq)}{\partial Dq} = A(q)m_x(q, Dq) \quad (60)$$

$$\frac{\partial P_x(q, Dq)}{\partial Dq} = A(q)P_x(q, Dq) + P_x(q, Dq)A^T(q) + B(q)B^T(q)$$

In Equation (60), $m_x(q,Dq)$ is the m×1 vector of mathematical expectation for the vector of test values x and $P_x(q,Dq)$ is the associated m×m covariance matrix. It is important to note that unlike the model of Equation (58), the model of Equation (60) is a vector model, i.e. it describes the joint statistical evolution of all clinical tests. In particular, this helps to capture the evolution of correlations between clinical tests. However, the model of Equation (60) is less general than that of Equation (58) in the sense that it is an approximation of the PDF with the first two statistical momenta. However, the model of Equation (60) is acceptable since the realistic distributions for the clinical tests are usually single-peak distributions ("core-and-tails" PDFs).

Equation (60) can be integrated analytically which yields the following result (see, e.g., Gelb, A., ed; *Applied Optimal Estimation*, The MIT Press, Cambridge, 1989):

$$m_x(q, Dq) = F(q, Dq)m_x(q, 0) \quad (61)$$

$$P_x(q, Dq) = F(q, Dq)P_x(q, 0)F^T(q, Dq) + \int_0^{Dq} F(q, J)B(q)B^T(q)F^T(q, J) dJ$$

where F (q,Dq) is the transition matrix for the system of Equation (59) and is expressed as a matrix exponent (see, e.g., Gelb, A., ed.; *Applied Optimal Estimation*, The MIT Press, Cambridge, 1989):

$$F(q,Dq) = e^{A(q,Dq)} \quad (62)$$

The matrices A(q) and B(q) are the parameters of the Markov process and are chosen as a result of solving a system identification problem given observations of x for different q and D q. The corresponding algorithm is based on the eigen value decomposition of the specially constructed observability matrix and is described in Crawley, E. F., Karlov, V. I., Miller, D. W., and Vander Velde, W. E., *Physical Identification for Control of Flexible Structures*, Special Course, MIT Space Engineering Research Center, 1993; and Karlov, V. I., Miller, D. W., Vander Velde, W. E., and Crawley, E. F., "Identification of Model Parameters and Associated Uncertainties for Robust Control Design," *AIAA Journal of Guidance, Control and Dynamics:* 1994, Volume 17, Number 3, pp. 495-504. A more complex model for the evolution of the statistics $m_x$ and $P_x$, which accounts for their uncertainties due to finite samples, is presented in Malyshev, V. V., Krasilshikov, M. N., and Karlov, V. I., *Optimization of Observation and Control Processes*, AIAA Education Series, 1992, p. 349).

It should also be noted that the parameters of the Markov process of Equation (59) are estimated. The experimental data used for estimating the trend in the clinical tests x correspond to different patients (assuming that there is no history of the tests for each single patient over a long period of time). However, the estimation is justified by the ergodic property (see, e.g., Gelb, A., ed, *Applied Optimal Estimation*, The MIT Press, Cambridge, 1989), which states that the evolutionary model for the stationary Markov process can be derived either from the ensemble of time histories of this random process or from the distributions of its values independently taken. ("snap-shot") at different instants.

After the evolutionary equations (58) or (60) are derived, they can be incorporated into the DBA as follows (using the age factor as an example). For each new patient one can "correct" the test values of other patients performing either "age-progression" (for younger patients) or "age-regression" (for older patients) propagations of statistics assuming that at Dq=0 the test values are initialized as the original test values and the associated covariance matrix is a zero matrix. After the propagation of the statistics to the actual Dq (the age difference) the test values of other patients become represented by the uncertainty ellipsoids. Conceptually, the DBA described in Section 3 can be directly applied to the uncertain data points after the test values of each patient are multiplied via the Monte-Carlo generation of M (say, 100) additional data points (given the statistics representing uncertainty ellipsoids). A more efficient in terms of the CPU solution (which is currently underway) would involve analytical operations with the uncertainty ellipsoids while performing the global and local estimation of the in the hypothesis-conditional PDF $p(x/H_k), k=1, \ldots, N$ in the DBA. The importance of making this operation more efficient follows also from the fact that the DBA should be adjusted (practically retrained) for each new patient since the differences in age are relative to the new patient. However, another practical alternative to the complete retraining of the DBA comes from the fact that one can simply precalculate and store in memory a set of differently-trained DBA for all possible values of age (e.g., for each year of age). The same formalism of using the DBA is applied for other factors q (e.g. height/weight).

3.2.4 Processing Historic Data

History of clinical tests for each patient is crucial for early diagnostics. The DBA in the training mode can identify differential historic patterns unique for different diseases. The DBA in the prediction mode can recognize the abnormal changes in tests of a new patient and relate the pattern of these changes to the statistical differential patterns of diseases. Thereby, in this process the DBA can account for other information such as age, sex, and other factors etc.

From a mathematical point of view, the DBA is developed for the formalism of Equations (5) and (6), which describes the dependency of the clinical tests X and diagnoses D on the history factor t.

To handle the X(t) dependency, the customized DBA uses the propagation equations in time (similar to Equation (58) or Equations (60), (61)) in order to relate the tests taken at different times to the compatible set of features. In particular, for the compatibility purposes the tests can be propagated to a set of fixed instants (sampled e.g. with an uniform interval in one month or one year). Correspondingly, one can think that the m-dimensional space of features X in the conventional diagnostics problem is now expanded to the m-dimensional space (where T is the number of time points on the uniform set). An important point here is that the propagation accounts for the correlations between the clinical tests (and, in general case, uncertainties in those correlations), which is the key for fusing a large amount of differential historic patterns.

To handle the D(t) dependency is offered the Markov probabilistic models for disease progression similar to the model of Equation (57). Correspondingly, the DBA is used in a dynamic mode propagating the conditional densities by the means of experimentally derived transition matrices.

From a mathematical point of view it is also important to note that the availability of the historic clinical data X(t) makes it possible not to rely any more on the ergodic property (as in Section 3.2.3) and estimate the propagation parameters directly. The latter is also applied to estimating the propagation parameters to model e.g. age trends in clinical tests (since each patient is observed over long period of time).

4. Diagnostics of Colon and Ovarian Cancer from Common Clinical Tests

An excellent example demonstrating the power of the DBA for diagnostics is afforded by the recent project conducted on patient chemical blood test data from Quest Diagnostics Laboratories ("Quest"). Quest provided us with a database of over 300,000 patient records, with each record consisting of patient demographics, the results of the chemical blood tests, and importantly, a diagnosis code. The goal of the project was to apply DBA technology in an attempt to characterize non-apparent patterns in blood test data of colon and ovarian cancer patients and then develop a predictive DBA algorithm to identify the possible presence of the diseases from the blood tests of new patients. In other words, the challenge was to find hidden statistical patterns in the common clinical tests, which might then enable detecting the cancers in as-yet-undiagnosed patients. The solution of this problem provides a demonstration of how the DBA can be customized to the particularities of a problem.

4.1 Description of the Clinical Data from the Quest Database

The main challenge of diagnosing malignant neoplasm (colon cancer and ovarian cancer) consists in the low prevalence of this disease. Table 1 illustrates the statistical proportions between records with different diagnoses by comparing the two datasets (Dataset #1 and Dataset #2), which represent the data from two different days of the testing operation by Quest Diagnostics.

TABLE 1

Statistics of Records with Different Diagnoses for
Two Datasets from Quest Diagnostics Database

|  | Dataset #1 | | | Dataset #2 | | |
|---|---|---|---|---|---|---|
| Type of records | Number | % (All) | % (V70) | Number | % (All) | % (V70) |
| All records | 326,639 | | | 344,900 | | |
| V70 General Medical examination | 19,759 | 6.05 | | 12,548 | 3.64 | |
| 153 Malignant neoplasm of colon | 1,164 | 0.36 | 5.89 | 948 | 0.27 | 7.56 |
| 183 Malignant neoplasm of ovary | 683 | 0.21 | 3.46 | 501 | 0.15 | 3.99 |
| 401: Essential hypertension | 28,187 | 8.63 | 143 | 22,729 | 6.59 | 181 |

As can be seen, in the Dataset #2, the records with colon cancer diagnosis (Code 153) take only 0.27% of all records and are only 7.56% of the volume of the V70 records. The records with ovarian cancer (Code 183) are about twice lower in volume, correspondingly 0.15% and 3.99%. But, the ovarian cancer records include only females while the colon cancer records include both males and females. Correspondingly, both cancers have approximately equal statistical representation in the datasets (as will be described below the colon cancer records should be split into two groups: M and F). Table 1 also shows that the Dataset #1 and Dataset #2 are statistically similar in the volume of diagnoses and appear to have realistic proportions of the records with cancer and the records with general medical examination (as well as of other diagnoses). This makes our studies more realistic.

Figure 13:
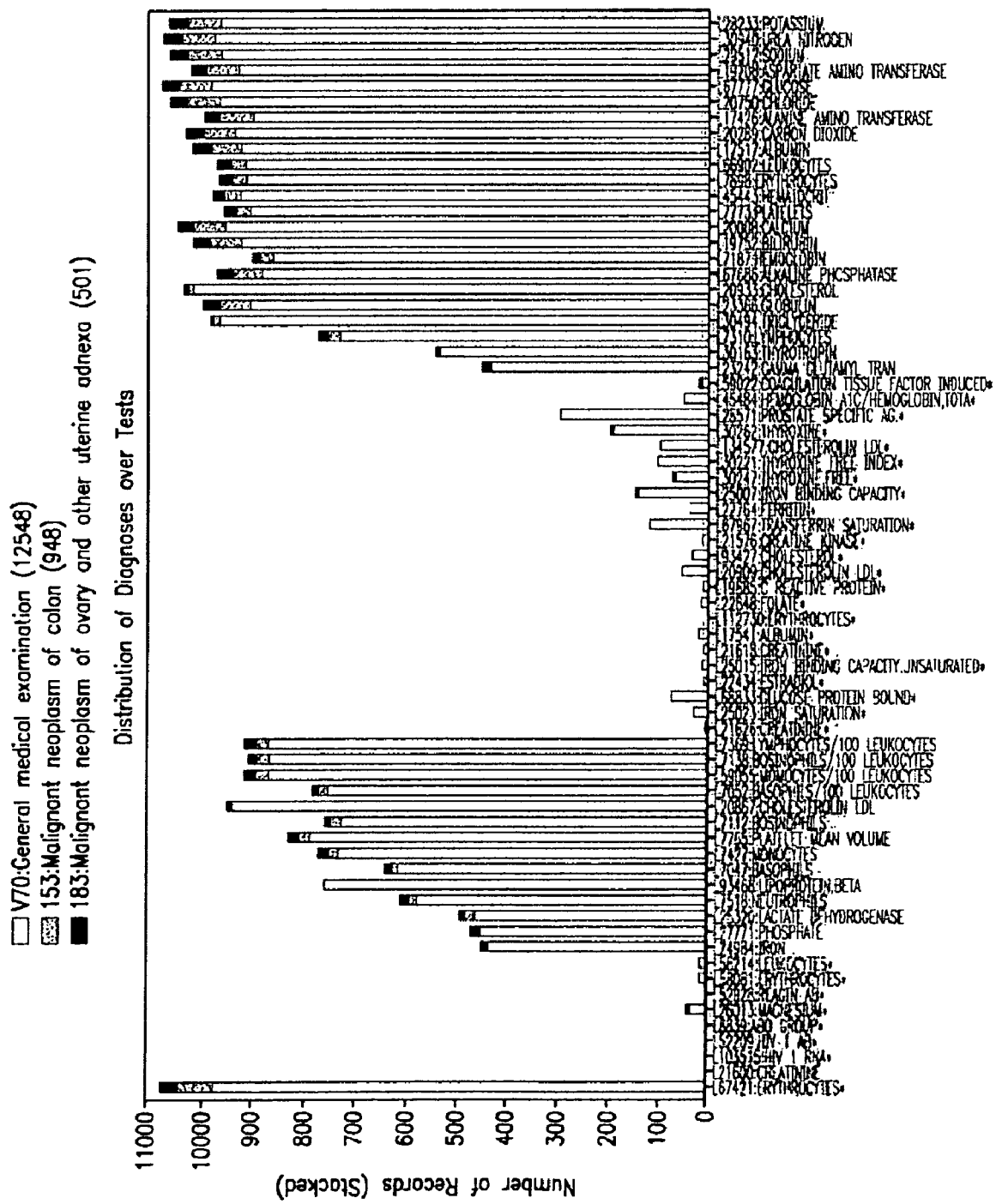
FIG. 13 is a graphical representation of a records distribution over 70 clinical tests for selected diagnoses in a dataset.

FIG. 13 presents a stacked plot, which shows how medical records are distributed over the clinical tests for each particular diagnosis. The selected diagnoses in FIG. 13 are "General medical examination" (Code V70), "Malignant neoplasm of colon" (Code 153) and "Malignant neoplasm of ovary and other uterine adnexa" (Code 183). Note that the names of common clinical tests (CBC and Chemical Screen tests), which are among the 49 clinical tests in Dataset #1, are not marked with a dot, while the names of the "new" tests added to Dataset #2 are marked with a dot. Also note that not all CBC and Chemical Screen tests from Dataset #1 are in Dataset #2. One can see that there are much fewer cancer records compared with the V70 records (this proportion differs over tests). It is important to note that all cancer records still have a reasonably sufficient number of many CBS and Chemical Screen tests (hundreds). With this amount it is possible to implement our statistical methods although with associated challenges to be described below. At the same time, it is impossible (using Dataset 42) to utilize the "new" (non-common) clinical tests for diagnosing cancer. The latter fact contributes to focusing our effort on diagnosing cancer from only common tests (CBC and Chemical Screen tests), although this also makes the problem more challenging.

In addition to the sparsity of the records in clinical tests, there is a need in splitting the records into different groups. This contributes to reducing the statistical data for their study (e.g. making 948 records with colon cancer in Dataset #2 even lower). First of all, the records should be split in two groups with respect to the patient's sex. This was identified as an imperative step. The further splitting of the records to generate a training set for the DBA algorithm and a control set for checking the DBA's performance is mandatory. As a result, one deals only with about a quarter of the total colon cancer records in each operation (training and checking) for each particular sex (M and F).

This lack of statistics becomes even more aggravated by the fact that each record has an incomplete set of clinical tests. The latter fact aggravates estimation of the correlations (or more generally, probabilistic dependencies) between the test's values.

4.2 SBI-Moldyn's Approach to Solution of the Problem

The approach to problems of this nature proceeds in three incremental steps. These steps are depicted as an evolutionary pyramid, illustrated by FIG. 28.

Figure 28:
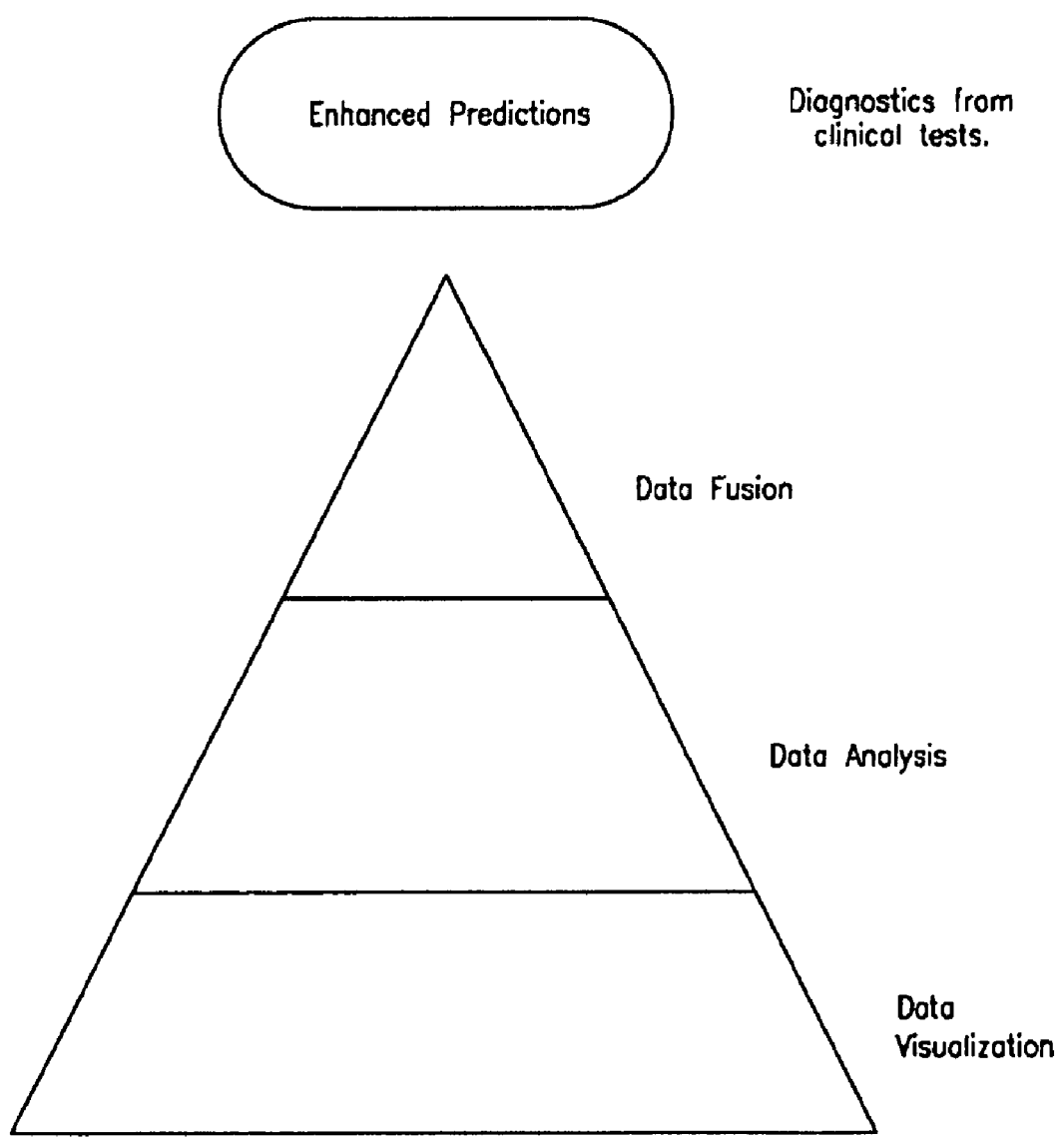
FIG. 28 is a graphical illustration of the incremental data analysis approach provided by the present invention.

FIG. 28 shows three primary elements of the approach: (1) data visualization; (2) data analysis; and, (3) data fusion. These are described below.

(1) Data Visualization

Data visualization offers plotting various histograms, distributions and scatter plots in 1D, 2D, 3D and in higher dimensions via parallel coordinates. This includes the automated search for hints (followed by visualization of details). When starting to work with the Quest data, visualization helped to understand the nature of this data. In particular, it helped (1) to confirm the fact that there is a relatively high degree of discrimination between records with different diagnoses in the space of clinical tests, (2) to assess the shapes of distributions in clinical tests (single peak distributions, sometimes close to the Gaussian distributions but sometimes having a high degree of asymmetry), (3) to confirm significant dependency of statistical distributions on the patient's sex and age.

(2) Data Analysis

This includes various statistical analyses of the data in order to identify general trends and dependencies.

(3) Data Fusion

Data fusion entails the integration of various pieces of information into knowledge (probabilistic prediction of diagnoses from the clinical tests). SBI-Moldyn's approach to solving the data fusion problem is based on estimation theory including statistical pattern recognition and multivariate analysis. The central algorithm of this approach is the DBA (Discrete Bayesian Approach) which is described in detail in Section 3.

The particular form of the DBA depends on customization along the physical structure of the problem. Customized for the Quest data, the DBA is capable of mining for a statistical pattern of a disease in the multi-dimensional space of clinical tests. This data mining and predictive power of the DBA comes from the following features:

(a) The ability to be robust to uncertainties in statistics (e.g., due to finite samples),
(b) The ability to seamlessly glue pieces of contradictory information,
(c) The ability to capture the trends in data with respect to various factors (e.g. with respect to age groups or demographics),
(d) The ability to handle the nonlinearities and the non-Gaussian nature of the distributions,
(e) The ability to do multiple diagnostics discriminating between a few candidate diseases,
(f) The concept of acceptance and success rates in diagnostics based on the utilizing a posteriori probabilities.

These features of the DBA were developed in order to meet the challenges of diagnosing colon and ovarian cancer from common clinical tests. These challenges are due to a low volume of the cancer data (low prevalence of cancer). Correspondingly, in the Quest database there is the disproportion of the cancer data to that of general medical examination (1:10 ratio). To handle these challenges, the robust DBA for handling sparse data was developed.

More Details on the DBA for Diagnostics from Clinical Tests (1) Data Visualization Developed was the automated data visualization system to understand the nature of the Quest clinical data. Below, some samples of this visualization are provided for the data used for diagnosing colon and ovarian cancer.

Figure 14:
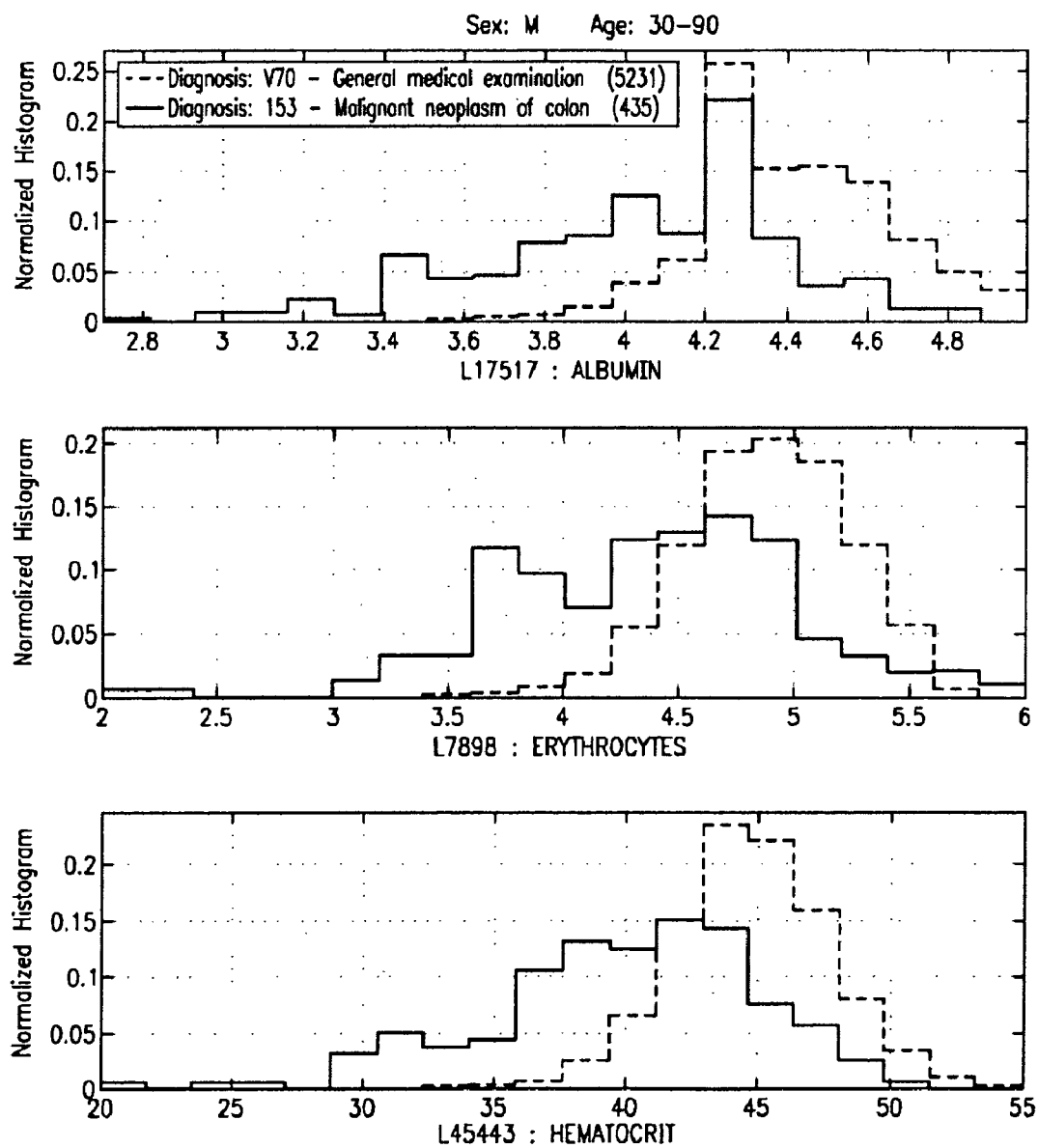
FIG. 14 is a graphical representation of the histograms for three selected clinical tests given a particular selection of two diagnoses as well as a patient's sex and age.

FIG. 14 displays the histograms for three informative clinical tests (ALBUMIN, ERYTHROCYTES, and HEMATOCRIT) given a particular selection of diagnoses as well as patient's sex and age group (Sex: M, Age: 30-90). This Figure shows that the diagnoses 153 (colon cancer) and V70 (general medical examination) substantially differ in each of the three clinical tests, thus, they provide the basis for statistical discrimination. (Note that the diagnosis indices 153 and V70 correspond to the International Disease Classification). One can also see that distributions of the test values are relatively asymmetric. It should be emphasized that there is a lack of statistics to accurately estimate the distributions for colon cancer (at least at the level as they are estimated for general medical examination).

Figure 15:
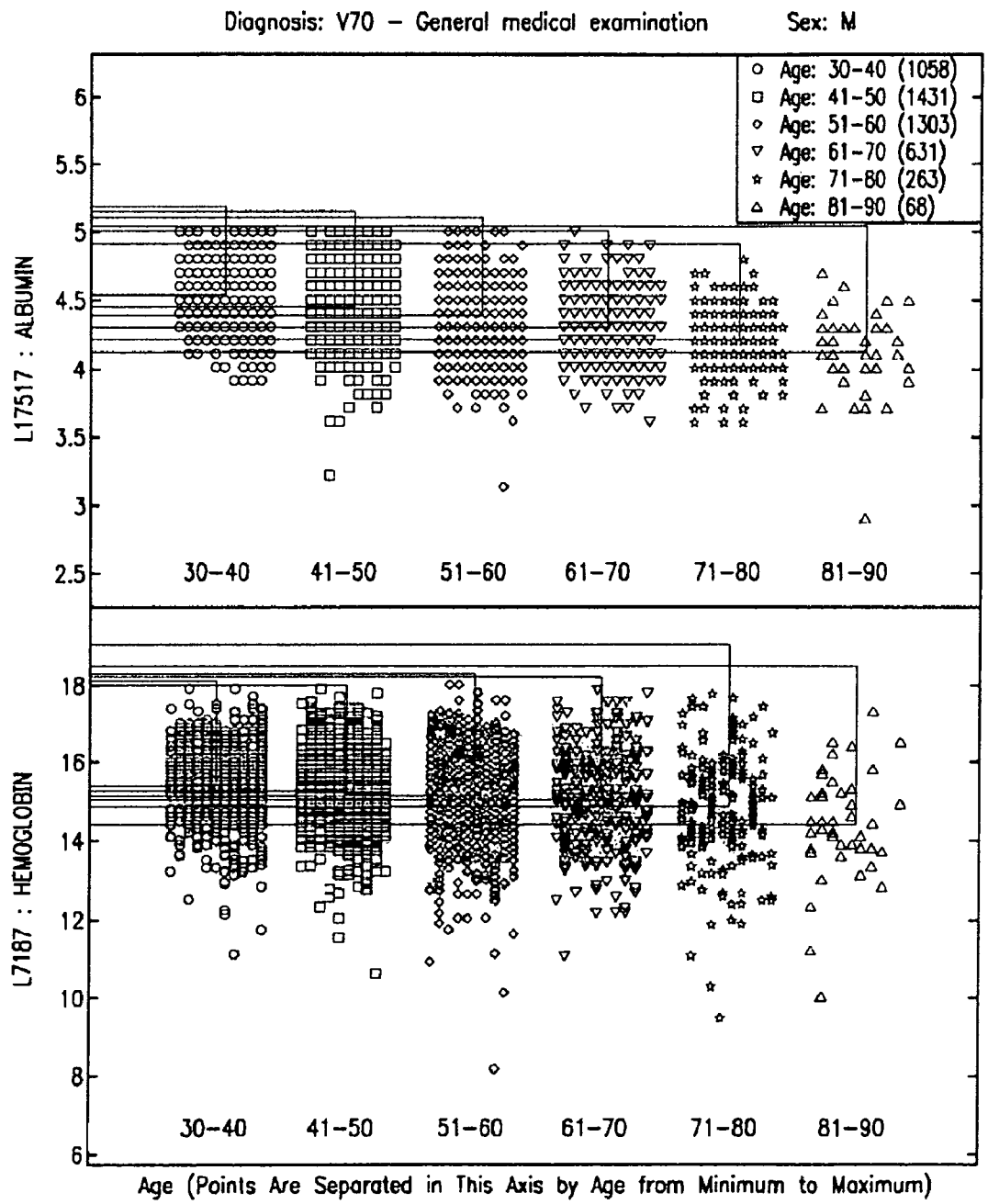
FIG. 15 is a graphical representation of a multiple scatter plot for three selected clinical tests given a particular selection of one diagnosis as well as patient's sex and age, where multiple scattering is for six age groups.

FIG. 15 provides a scattering plot for the two tests ALBUMIN and HEMOGLOBIN using the age groups as a multiple factor for comparisons. The scattering is shown for the records with general medical examinations (due to a high volume). It is apparent that there is an age trend in the tests values, which is effectively accounted by the DBA (using statistics for training from different age groups).

Figure 16:
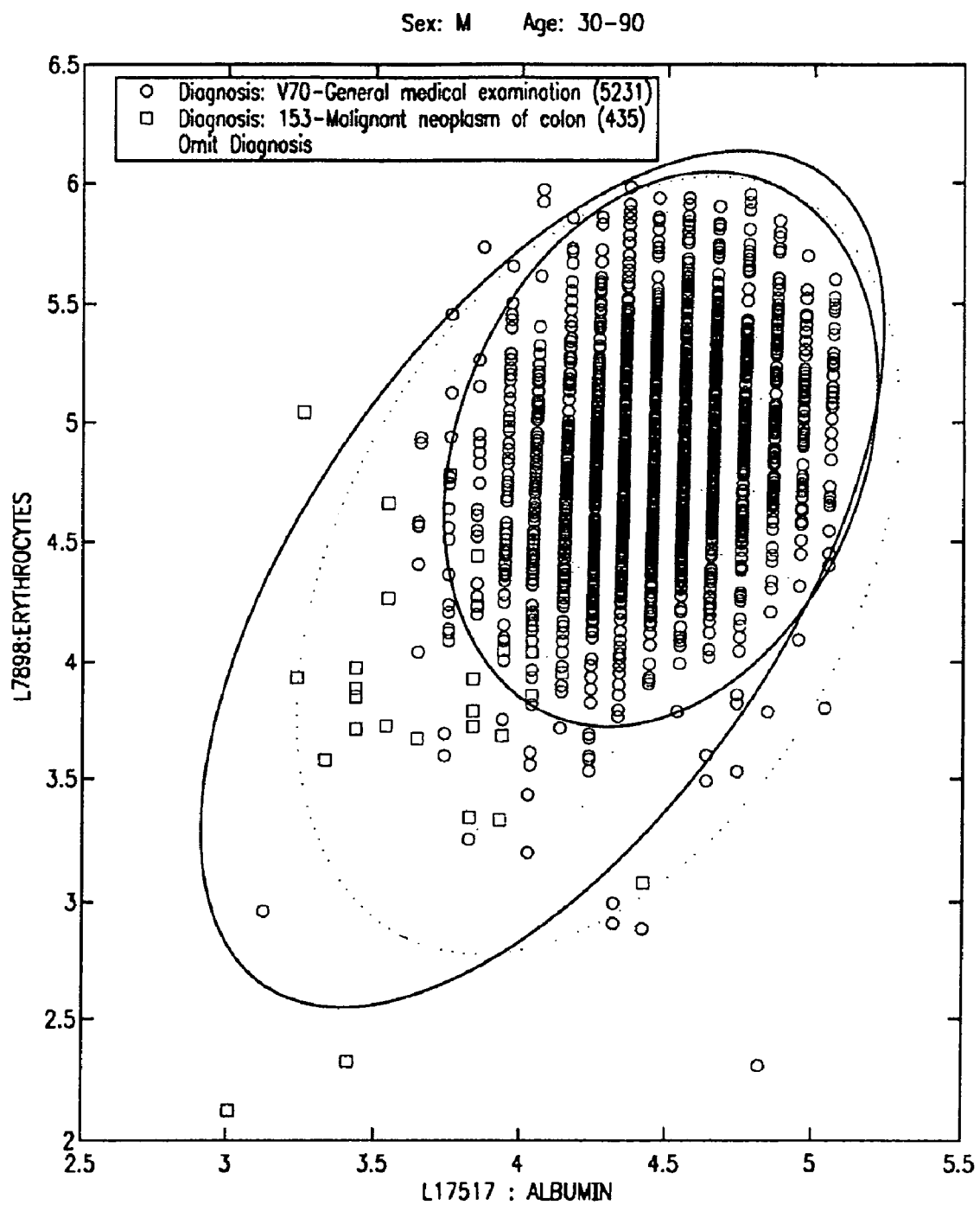
FIG. 16 is a graphical representation of the scattering of data in 2D for two selected clinical tests, showing the difference in distributions for two selected diagnoses

FIG. 16 visualizes scattering of data for colon cancer and general medical examination in 2D for two selected clinical tests (ALBUM and ERYTHROCYTES). The Gaussian approximations in 2D are plotted too (including the "omit" ellipsoid). It should be clarified that the ellipsoids represent the level line of the two-dimensional Gaussian function corresponding to the 3-sigma STD (standard deviation) in both coordinates. The tests are also discrete in their values so that some points are overlapped. There is a strong correlation in the values of the two tests, which needs to be accounted by the DBA.

(2) Data Analysis

Before performing data fusion from multiple tests, is important to make analysis of a single test in terms of its ability to discriminate between different hypotheses (diagnoses). First, this analysis provides important statistical criteria such as sensitivity, specificity and acceptance for each test. Each test has an individual statistical pattern and the predictive algorithm has to effectively exploit these individual test's properties while fusing the multiple clinical tests. Second, the assessment of these statistical criteria (sensitivity, specificity and acceptance) makes it possible to rank a large amount of potential tests in terms of their discrimination ability (for each pair of hypotheses) and on this basis to select a smaller subset of important tests. This is a feature selection procedure in the classification problems.

The concept of sensitivity/specificity (see Motulsky, H.; Intuitive Biostatistics, Oxford University Press, 1995) is generalized by introducing "acceptance" and developing the effective algorithm for computing all three statistical criteria. The algorithm for computing the specificity/sensitivity/acceptance probabilities treats the nonlinear distribution for a scalar test exactly. It is based on a threshold algorithm (defined by a likelihood ratio).

For the acceptance probability=1, there is only one optimal threshold value. The entire specificity/sensitivity curve is generated by "sliding" the threshold from the minimum to maximum value and computing the corresponding ratios:

$$Sp(t) = \frac{TN}{TN + FP}, Se(t) = \frac{TP}{TP + FN} \quad (63)$$

In Equation (63), Sp stands for sensitivity, Se stands for specificity, TN stands for True Negatives, TP stands for True Positives, FP stands for False Positives, t stands for threshold. Correspondingly, TN+FP represents all patients (records) in the control group (e.g. V70—General Medical Examination) and TP+FN represents the patients with a disease (e.g. 153—Malignant Neoplasm of Colon).

For the acceptance probability <1, the threshold is a boundary with a lower ($t_L$) and upper ($t_U$) values. To explore the specificity-sensitivity-acceptance space one needs to sample all combinations of the lower and upper thresholds. A fast recursive algorithm was developed for effectively operating in real time over a space of all possible pairs ($t_L$, $t_U$), using calculations from previous step. Correspondingly, Equation (63) is generalized:

$$Sp(t_L, t_U) = \frac{ATN}{ATN + AFP}, ASp(t_L, t_U) = \frac{ATN + AFP}{TN + FP} \quad (64)$$

$$Se(t_L, t_U) = \frac{ATP}{ATP + AFN}, ASe(t_L, t_U) = \frac{ATP + AFN}{TP + FN}$$

where ASp is the acceptance associated with the specificity and ASe is the acceptance associated with the specificity. Also, adding A in a front of any other notation (TN, FP, TP, FN) implies that those records were accepted for prediction.

Figure 17:
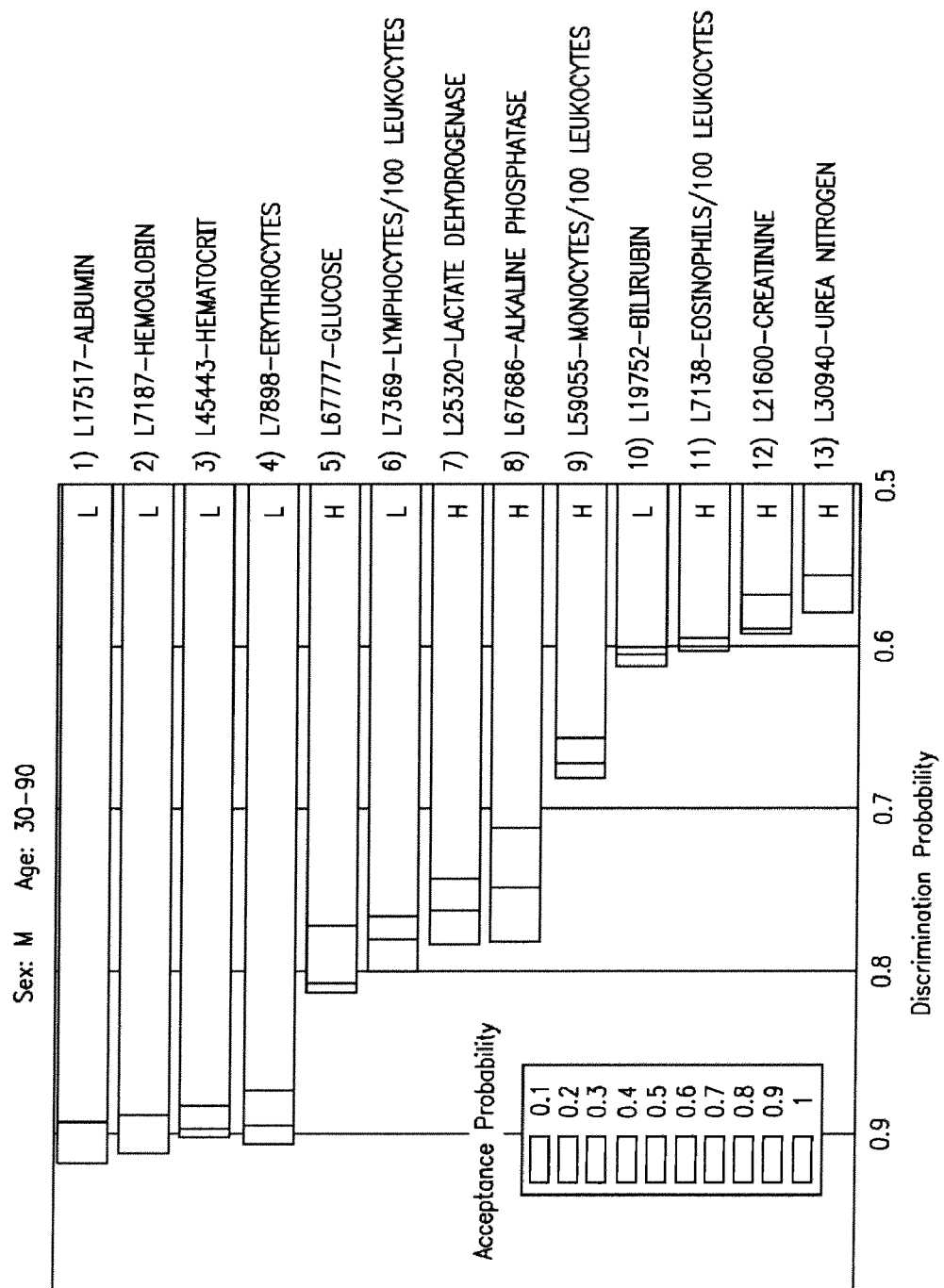
FIG. 17 is a graphical representation of the ranking of clinical tests in terms of their discriminative power for diagnostics of colon cancer (shown for different levels of acceptance).

FIG. 17 provides the ranking of clinical tests in terms of their discriminative power in diagnosing colon cancer. The performance of each test is presented by a scalar value, which is the discrimination probability. The latter is the average of the specificity and sensitivity. One can interpret the discrimination probability as a probability of a success of making the right prediction (one of the diagnoses) given the equal prevalence of the two diagnoses. The acceptance criterion specifies a portion of the population for which the DBA attempts prediction (note that by reducing the acceptance value one can increase the sensitivity/specificity performance, i.e. better detect a disease for a smaller group of patients). It also should be noted that although working with a scalar test is somewhat trivial in a mathematical sense, it is important to define its right "statistical pattern" (in our case using the expanded concept of specificity-sensitivity-acceptance) for further data fusion of multiple tests. The DBA performs data fusion given all the quantified differences between the tests in specificity, sensitivity and acceptance trade-offs (including the bounds on those quantities).

(3) Data Fusion

Data fusion is performed by the DBA (Discrete Bayesian Approach) which is described in detail in Section 3.

Since this was not data from a specifically designed experiment, it was necessary to structure the problem within the constraints of the available data. Records (and clinical test results) were available for patients with a diagnosis code of colon cancer, and for patients with a diagnosis code of ovarian cancer. There were of course many other records with other disease diagnoses. For a "healthy" control group (i.e., to discriminate the cancer patients against), the only option was to use patients with a diagnosis code of "general medical exam". The algorithm was developed and implemented just as shown in FIG. 1. The patient population (colon cancer, ovarian cancer and general medical exam diagnoses) was divided in half. The DBA algorithm was trained on half the sample, and then applied in a predictive mode against the other half (the test population). The resulting predictions were then compared with the actual diagnosis codes in the test population records in order to generate accuracy (sensitivity and specificity) statistics.

Figure 18:
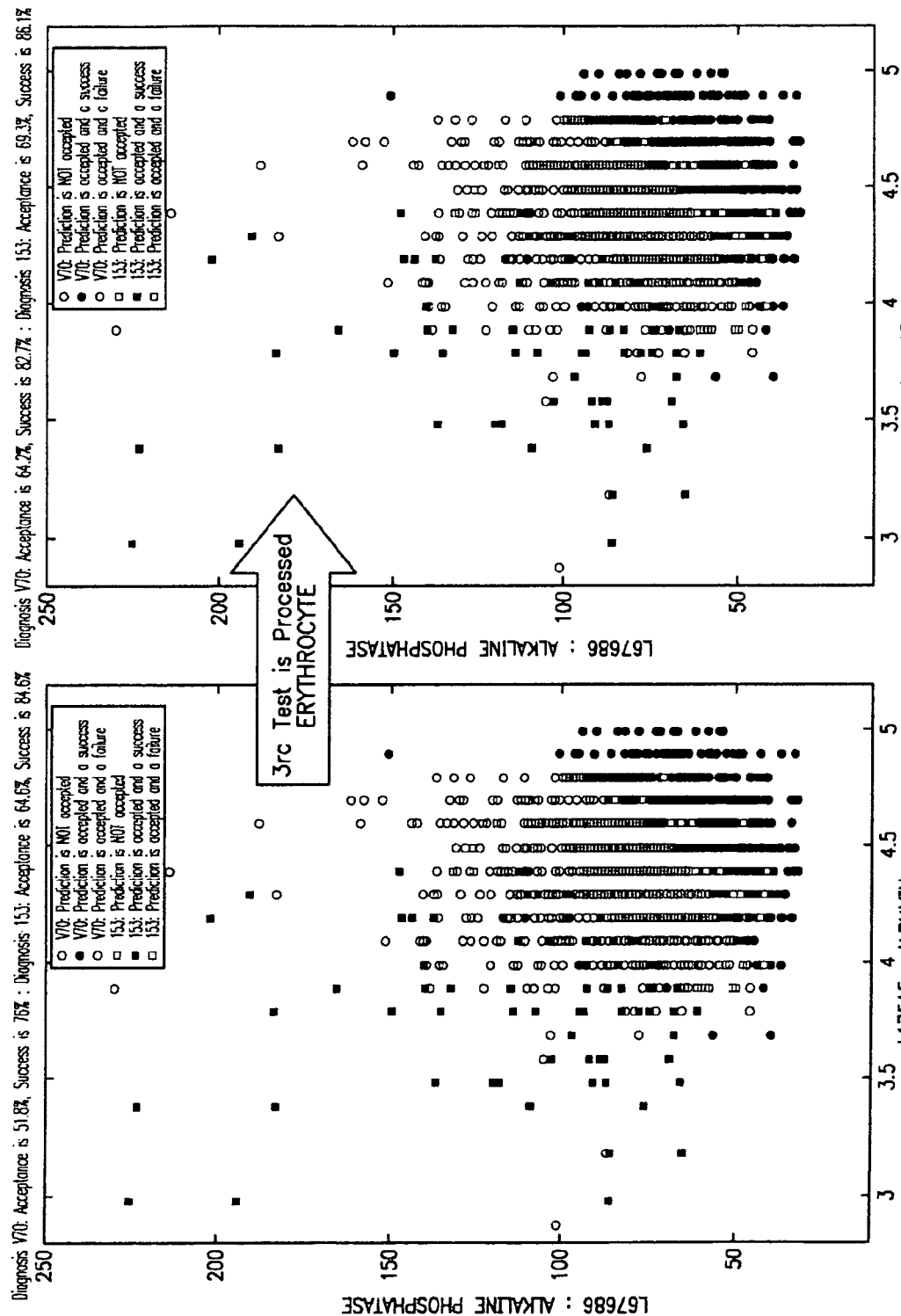

FIGS. 18a and 18b illustrate the process of data fusion by the DBA. Discrimination between two hypotheses: V70 (General medical examination) and 153 (Malignant neoplasm of colon) is considered; three tests are used (ALBUMIN, ALKALINE PHOSPHATASE, and ERYTHROCYTES); and, the results correspond to the selection [Sex: M, Age: 30-90]. The patients (their records) from the control set are displayed on the scatter plot of FIGS. 18a, 18b as markers with the indication of how they were diagnosed. The shapes and colors of the markers conform to the following convention. Each record with a particular diagnosis retains the shape of the marker and the color of the marker's edge (circle/blue for V70 and red/square for 153). How the marker's face is filled in and colored depends on the result of the predicted diagnosis. Non-colored marker's faces show so-called rejected predictions. In such cases, the algorithm (based on statistical probabilities) has determined that a choice between the two alternatives (colon cancer or general medical examination) is too close to call. The marker's faces colored in red or blue indicate successful prediction while the yellow color indicates unsuccessful predictions. FIG. 18a corresponds to a stage of the data fusion when the first two tests are processed (ALBUMIN and ALKALINE PHOSPHATASE). Since ALKALINE PHOSPHATASE has a rather non-Gaussian distribution the robust DBA draws a broad "decision line" between the two sets. This reduces the acceptance probabilities to 51.8% (for V70) and 64.6% (for 153). FIG. 18b demonstrates that the processing of the third test (ERYTHROCYTES) increases the acceptance probabilities to 64.2% and 69.3% correspondingly. The success probabilities were also improved: 76%→82.7% (V70, i.e. specificity) and 84.6%→86.1% (153, i.e. sensitivity). From a visualization point of view, one can see that adding the third test (third dimension) helps to fill-in quite a few markers on the fuzzy "decision line." In the general case, fusing additional tests further improves the acceptance/success probabilities.

Our simulations of the DBA include three different studies (which were the result of consecutive investigative work). These three types of studies are the following:

(1) First, as many clinical tests as possible were used. In this case the reasonable set included six tests identified as most predictive. All records designated for control were used (even those which have only one test from the six tests selected). But it was difficult to fuse all six tests mainly due to the poorly estimated correlations between some clinical tests (the culprit is a lack of statistics).

(2) Investigation was limited to the two most informative clinical tests (ALBUMIN and ERYTHROCYTES). These studies retained in the designated control set only those records, which have both tests. At this stage also expanded was the V70 diagnosis with other diagnoses in order explore the capability of the DBA to discriminate cancer from a group of mixed diagnoses.

(3) The number of tests was increased. But, the two mandatory tests (ALBUMIN and ERYTHROCYTES) were used plus another two tests (HEMATOCRIT and HEMOGLOBIN), which a record could have. In other words, control records were chosen so that the two mandatory tests were present and the additional two tests were used when available. This resulted in a more successful strategy to fuse the data.

Below is provided the results for all three studies of the DBA simulations. It should be noted that the figures and tables are self-explanatory (e.g. diagnoses and selections in sex and age groups are displayed). Comments are provided only when it is necessary.

Study 1of the DBA Simulations

Figure 19:
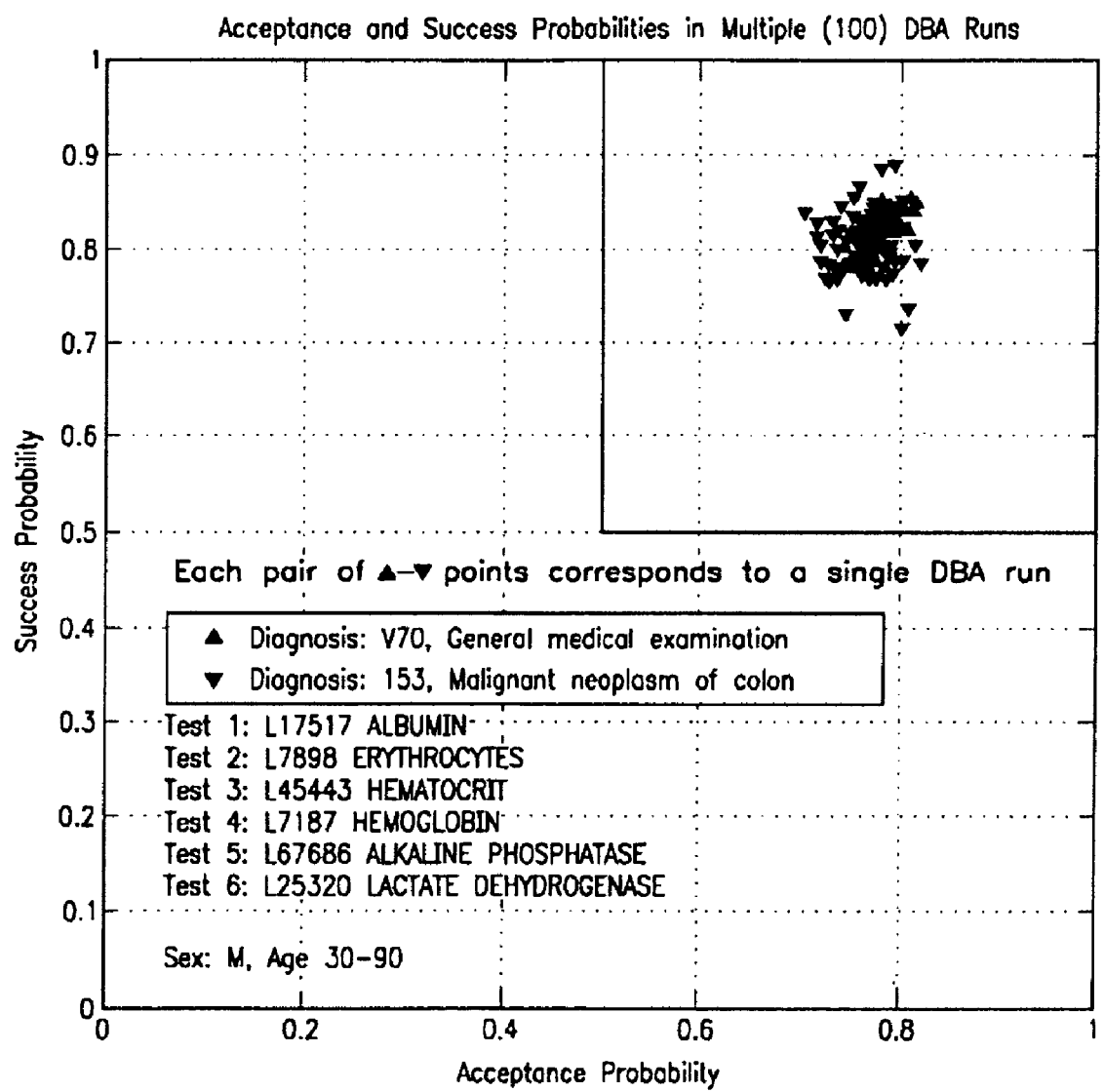
FIG. 19 is a graphical representation of the assessment of the DBA performance in terms of acceptance and success probabilities via Monte-Carlo simulations. Shows trends in discrimination of two diagnoses.
Figure 20:
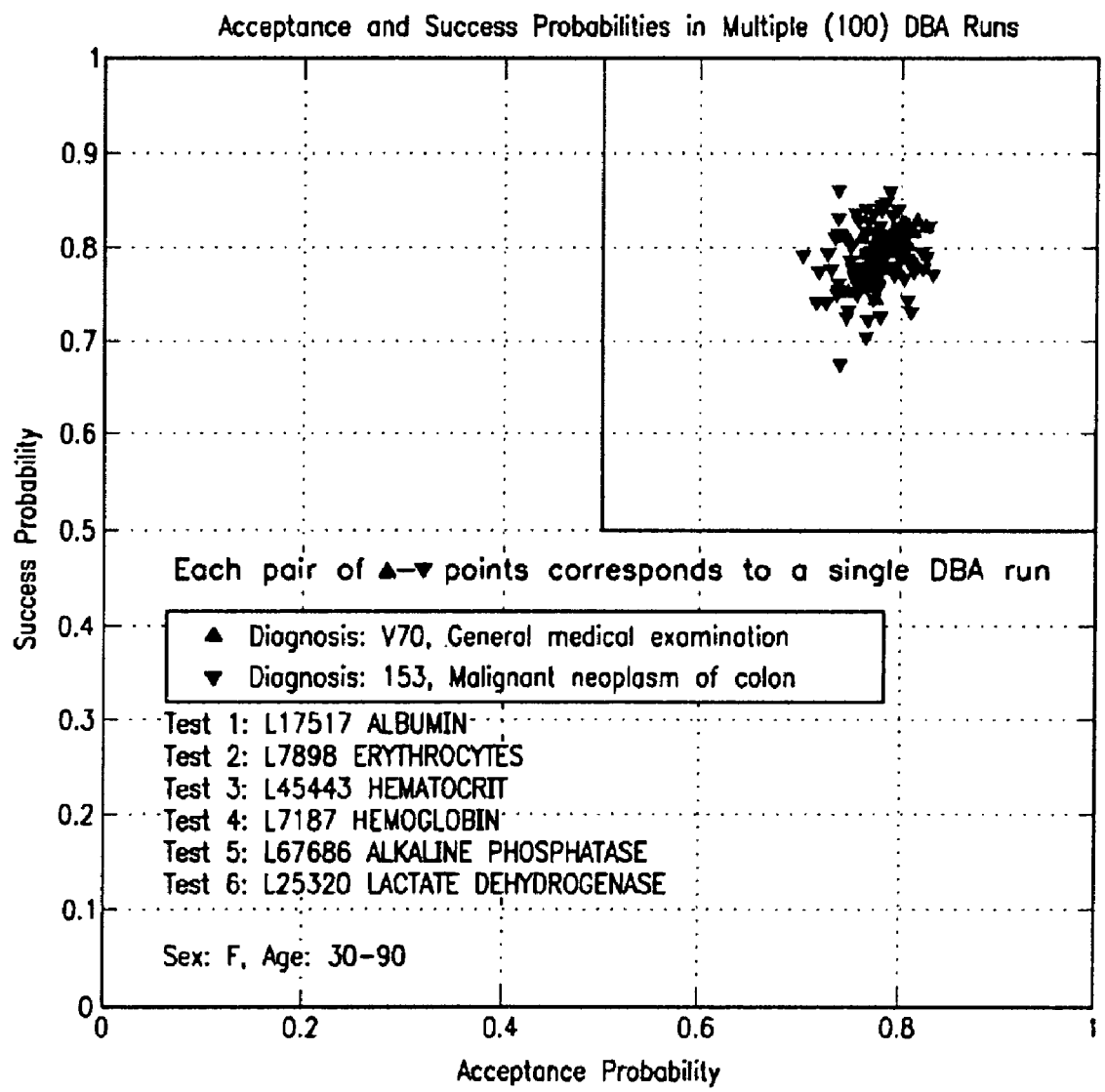
FIG. 20 is a graphical representation of the assessment of the DBA performance in terms of acceptance and success probabilities via Monte-Carlo simulations, showing trends in discrimination of two diagnoses.
Figure 21:
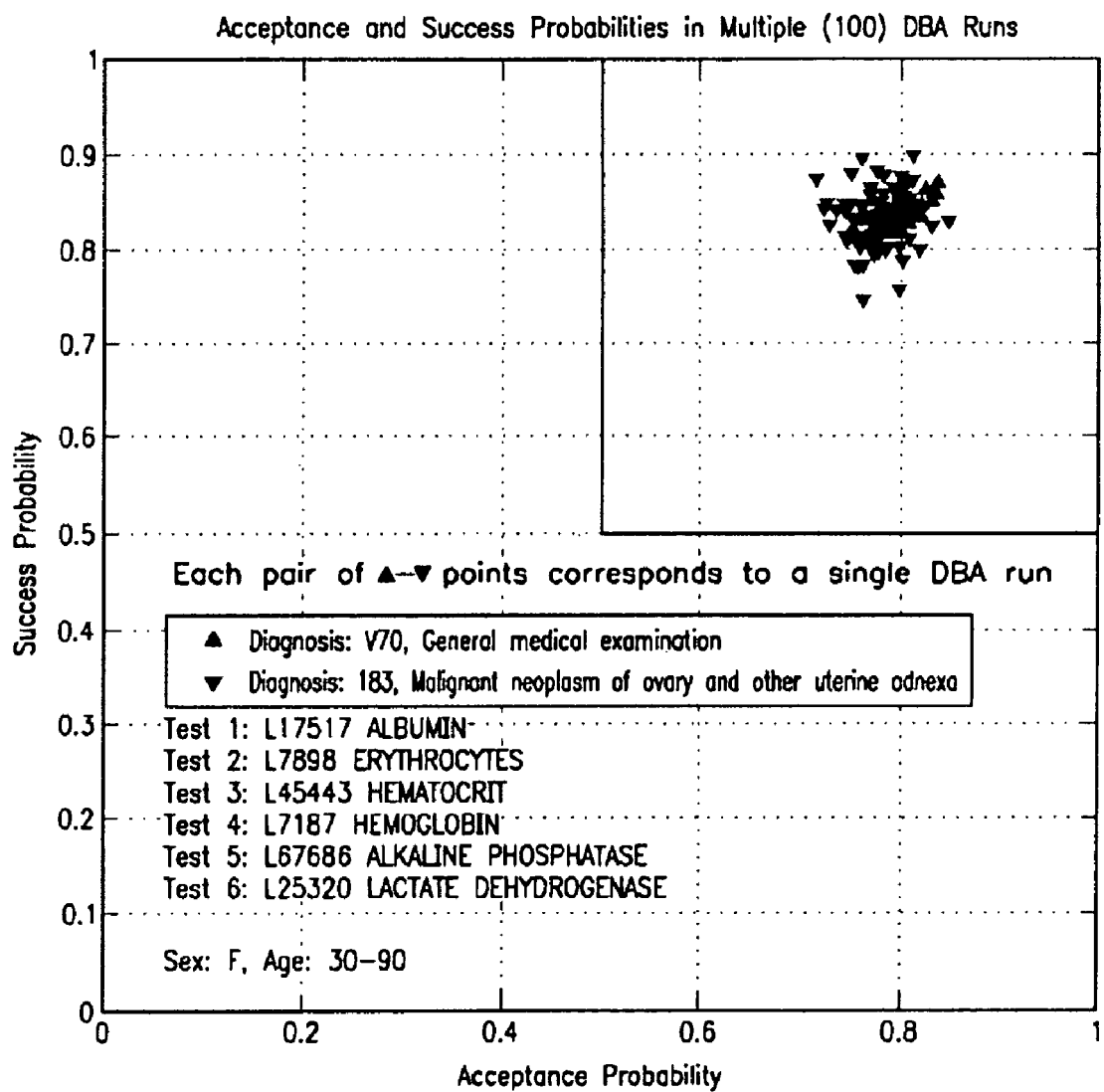
FIG. 21 is a graphical representation of the assessment of the DBA performance in terms of acceptance and success probabilities via Monte-Carlo simulations, showing trends in discrimination of two diagnoses.

FIGS. 19-21 illustrate the distribution of the acceptance and success probabilities in the 100 Monte-Carlo runs of the two-diagnosis DBA. As was described above, each run is associated with a randomly generated training and control sets of records. All six clinical tests are processed (of course, if available since not each patient has a combination of all six tests).

FIG. 19 corresponds to discrimination of colon cancer from general medical examination and vice versa for the selection [Sex: M, Age: 30-90]. FIG. 20 corresponds to discrimination of colon cancer from general medical examination and vice versa for the selection [Sex: F, Age: 30-90]. FIG. 21 corresponds to discrimination of ovarian cancer from general medical examination and vice versa for the selection [Sex: F, Age: 30-90].

The means (mathematical expectations) and the STDs (standard deviations) of the acceptance and success probabilities are summarized in the following three tables.

| Discrimination between two specified diagnoses (Sex: M) | Probability of acceptance | | Probability of success | |
|---|---|---|---|---|
| | Mean | STD | Mean | STD |
| 153 Malignant neoplasm of colon | 0.77 | 0.02 | 0.81 | 0.03 |
| V70 General Medical examination | 0.78 | 0.01 | 0.82 | 0.02 |

| Discrimination between two specified diagnoses (Sex: F) | Probability of acceptance | | Probability of success | |
|---|---|---|---|---|
| | Mean | STD | Mean | STD |
| 153 Malignant neoplams of colon | 0.77 | 0.03 | 0.79 | 0.04 |
| V70 General Medical examination | 0.78 | 0.02 | 0.79 | 0.02 |

| Discrimination between two specified diagnoses (Sex: F) | Probability of acceptance | | Probability of success | |
|---|---|---|---|---|
| | Mean | STD | Mean | STD |
| 183 Malignant neoplams of ovary | 0.78 | 0.02 | 0.83 | 0.03 |
| V70 General Medical examination | 0.80 | 0.02 | 0.83 | 0.01 |

Study 2 of the DBA Simulations

Figure 22:
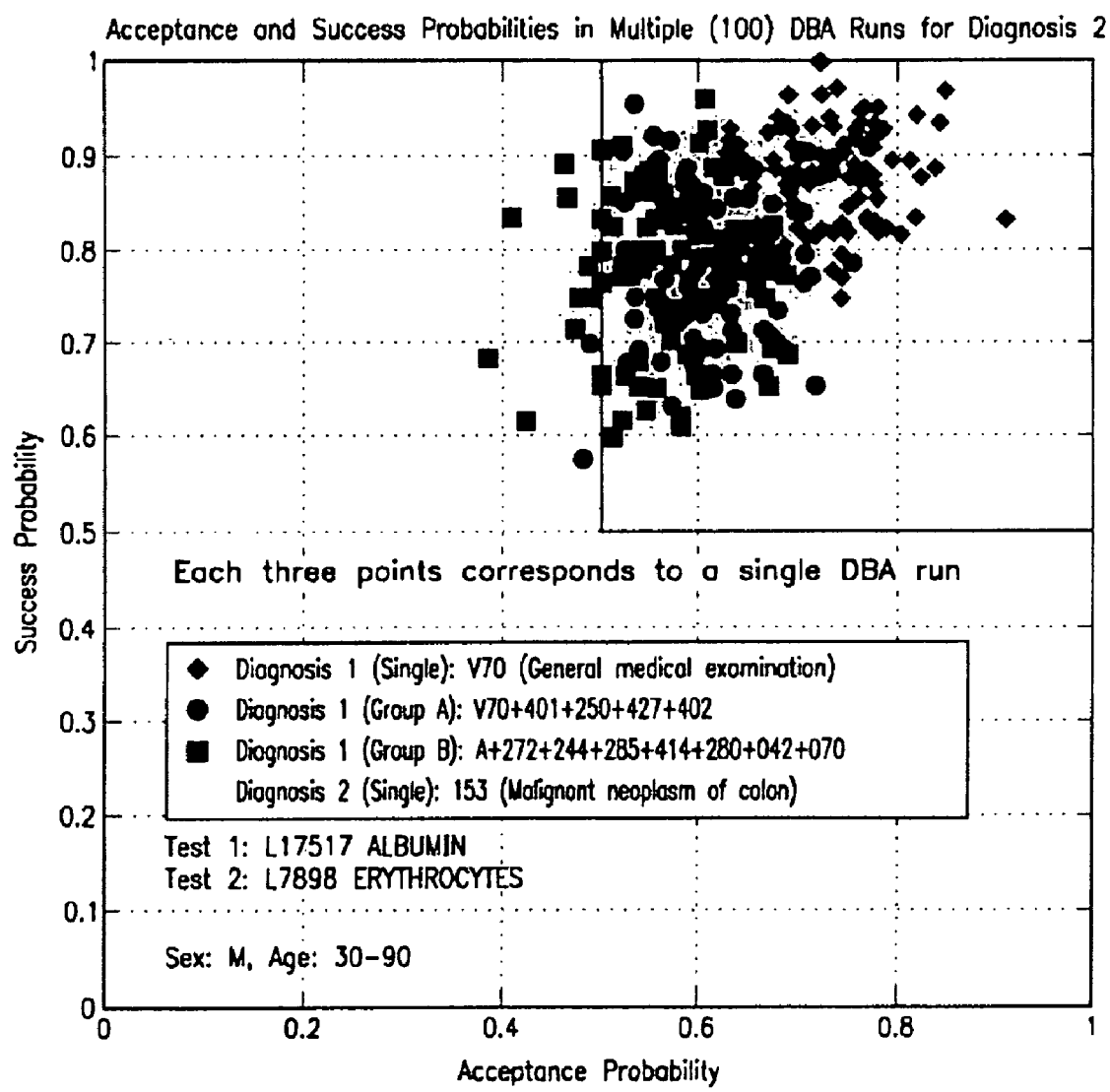
FIG. 22 is a graphical representation of the assessment of the DBA performance in terms of acceptance and success probabilities via Monte-Carlo simulations, showing trends in discrimination of Diagnosis 2 (colon cancer) from three types of Diagnosis 1 (general medical examination plus expansions).
Figure 23:
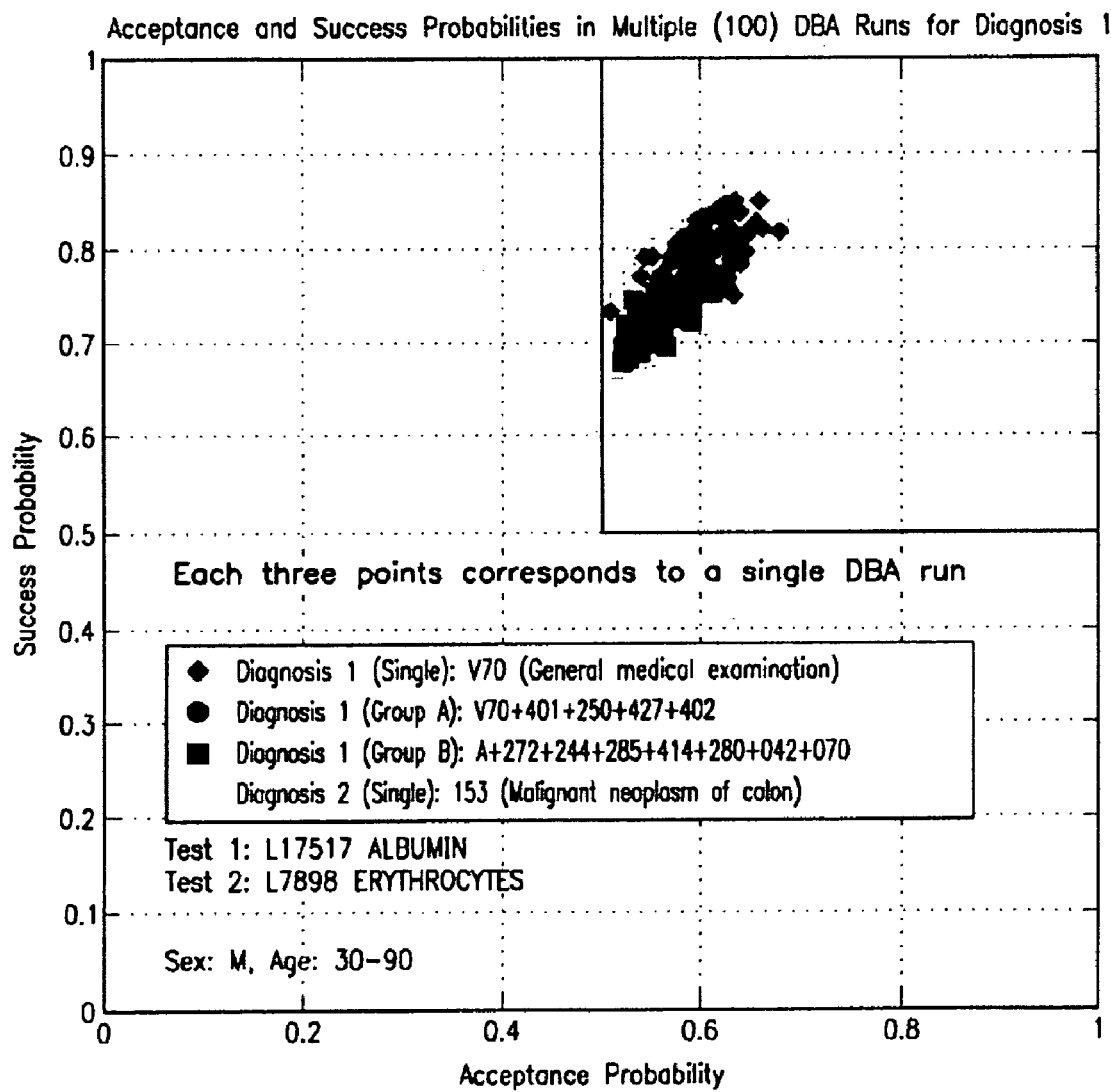
FIG. 23 is a graphical representation of the assessment of the DBA performance in terms of acceptance and success probabilities via Monte-Carlo simulations, showing trends in discrimination of three types of Diagnoses 1 (general medical examination plus expansions) from Diagnosis 2 (colon cancer).

FIGS. 22-23 illustrate the distribution of the acceptance and success probabilities in the 100 Monte-Carlo runs of the two-diagnosis DBA. The two tests (ALBUMIN and ERYTHROCYTES) are used. The two figures correspond to the case when colon cancer (Diagnosis 2) is discriminated against another diagnosis (Diagnosis 1). FIGS. 22-23 provide results for three different types of Diagnosis 1:

V70 (General medical examination, GME)
Group A: GME (V70)+Diabetes (250)+Hypertension (401)+Cardiac diseases (402, 427)
Group B: Group A+HIV (042)+Viral hepatitis (070)+Anaemias (280, 285)+Hypothyroidism (244)+Disorders of lipoid metabolism (272)

Here, the most frequent diagnoses are chosen to add to V70, thus further decreasing the percentage of the cancer records.

FIG. 22 provides the acceptance and success probabilities for discriminating Diagnosis 2 (colon cancer) from one of the three specified Diagnosis 1 (V70, Group A, and Group B). FIG. 23 provides the acceptance and success probabilities for discriminating one of the three specified Diagnosis 1 (V70, Group A, and Group B) from Diagnosis 2 (colon cancer).

The two tables below provide the summary of the means and STDs for the acceptance and success probabilities scattered in FIG. 22 and FIG. 23.

| Discrimination of 153 (colon cancer) from a specified diagnosis (Sex: M) | Probability of acceptance | | Probability of success | |
|---|---|---|---|---|
| | Mean | STD | Mean | STD |
| V70 General Medical examination | 0.74 | 0.05 | 0.88 | 0.05 |

-continued

| Discrimination of 153 (colon cancer) from a specified diagnosis (Sex: M) | Probability of acceptance | | Probability of success | |
|---|---|---|---|---|
| | Mean | STD | Mean | STD |
| Group of diagnoses (Group A) | 0.62 | 0.06 | 0.78 | 0.08 |
| Group of diagnoses (Group B) | 0.57 | 0.06 | 0.79 | 0.08 |

| Discrimination of a specified diagnosis from 153 (colon cancer) (Sex: M) | Probability of acceptance | | Probability of success | |
|---|---|---|---|---|
| | Mean | STD | Mean | STD |
| V70 General Medical examination | 0.60 | 0.03 | 0.80 | 0.02 |
| Group of diagnoses (Group A) | 0.58 | 0.02 | 0.75 | 0.02 |
| Group of diagnoses (Group B) | 0.56 | 0.02 | 0.73 | 0.02 |

The results show that the performance in discriminating colon cancer from a group of diagnoses drops when more diagnoses are added to the group.

The fact that the success probabilities of prediction (just from two tests) remain at the level of 70% (with the acceptance probability reduced to a level of 55%) leads us to believe that accurate diagnostics of colon cancer from common clinical tests are still possible. But, this will require development of the multiple-diagnosis DBA with a better scheme of fusing many clinical tests with uncertain statistics. As it is emphasized throughout this Technical Memorandum, the multiple-diagnosis DBA will be able to detect the statistical differences between any pair of two diagnoses from clinical tests (not just one diagnosis vs. all diagnoses combined). Increasing the number of clinical tests will facilitate the discrimination in the space of multiple hypotheses (diagnoses). Also, better utilization of the trends with age and other factors will sharpen the discrimination power of the multiple-hypothesis DBA.

Study 3 of the DBA Simulations

Figure 24:
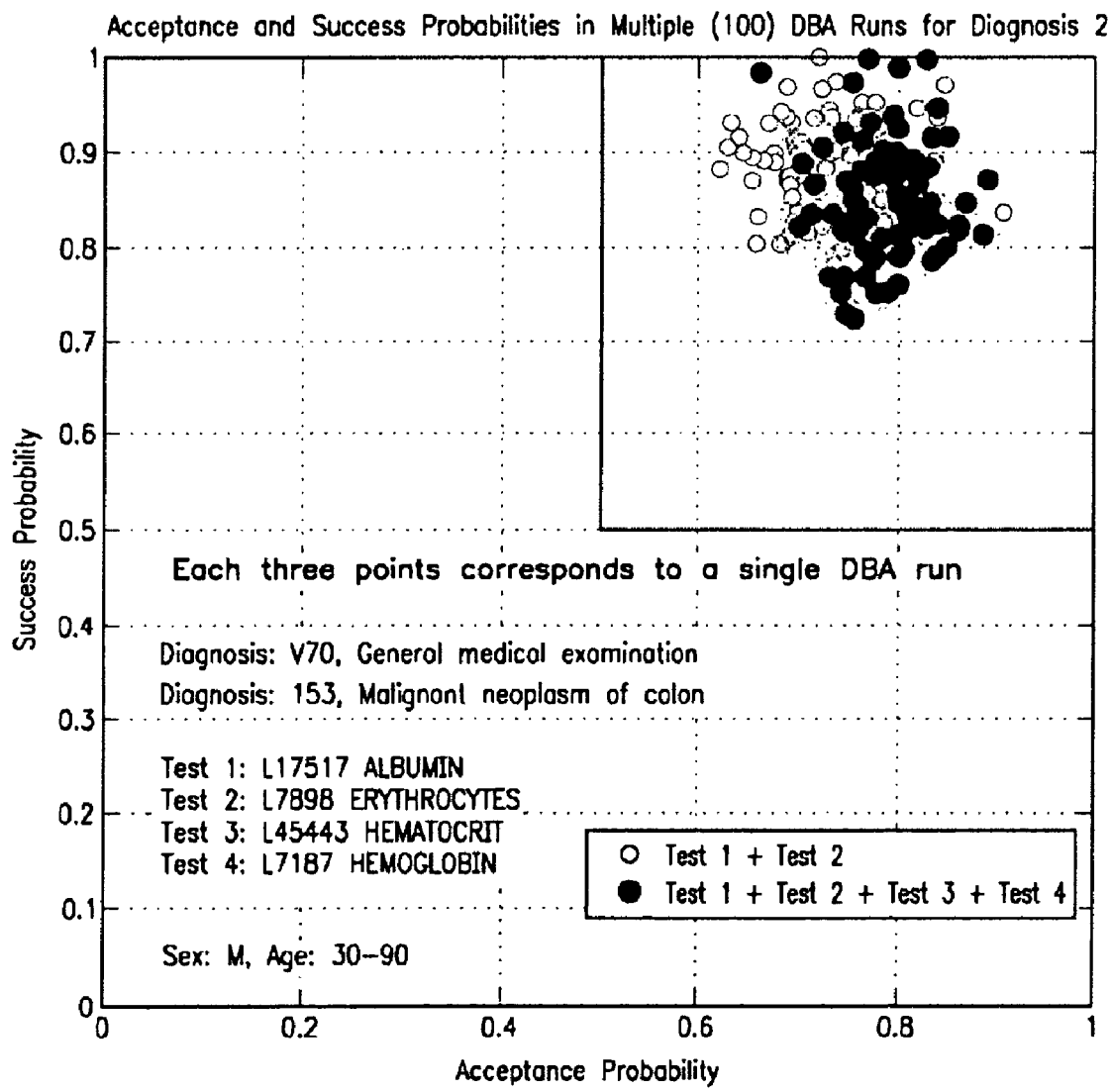
FIG. 24 is a graphical representation of the assessment of the DBA performance in terms of acceptance and success probabilities via Monte-Carlo simulations, showing the effect of data fusion with increasing number of tests.
Figure 25:
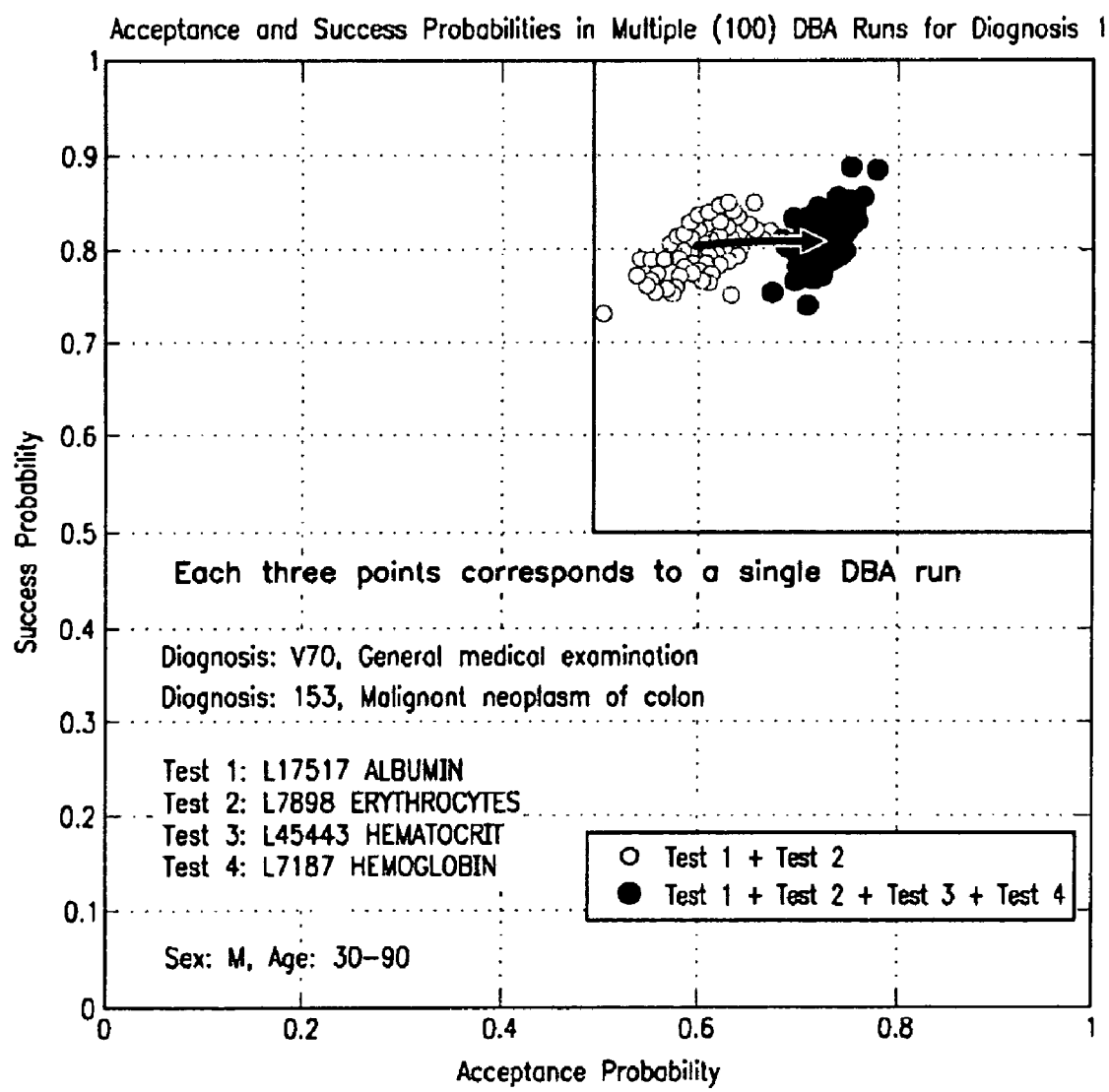
FIG. 25 is a graphical representation of the assessment of the DBA performance in terms of acceptance and success probabilities via Monte-Carlo simulations, showing the effect of data fusion with increasing number of tests.

FIGS. 24-25 illustrate the distribution of the acceptance and success probabilities in the 100 Monte-Carlo runs of the two-diagnosis DBA. Note that in this case the mandatory tests (ALBUMIN and ERYTHROCYTES) are used plus other two tests (HEMATOCRIT and HEMOGLOBIN), which a record could have. The two plots correspond to the case when colon cancer (Diagnosis 2) is discriminated against general medical examination (Diagnosis 1). FIG. 24 corresponds to the case "Diagnosis 2 from Diagnosis 1" and FIG. 25 corresponds to the case "Diagnosis 1 from Diagnosis 2."

The two tables below provide the summary of the means and STDs for the acceptance and success probabilities scattered in FIG. 24 and FIG. 25.

| Discrimination of 153 (colon cancer) from V70 (GME) (Sex: M) | Probability of acceptance | | Probability of success | |
|---|---|---|---|---|
| | Mean | STD | Mean | STD |
| Test 1 + Test 2 | 0.74 | 0.05 | 0.88 | 0.05 |
| Test 2 + Test 2 + Test 3 + Test 4 | 0.79 | 0.04 | 0.85 | 0.06 |

| Discrimination of V70 (GME) | Probability of acceptance | | Probability of success | |
|---|---|---|---|---|
| from 153 (colon cancer) (Sex: M) | Mean | STD | Mean | STD |
| Test 1 + Test 2 | 0.60 | 0.03 | 0.80 | 0.02 |
| Test 2 + Test 2 + Test 3 + Test 4 | 0.73 | 0.02 | 0.81 | 0.03 |

From these studies one can see that a fusion of more tests significantly improves the acceptance probabilities. But, it is more difficult to improve on the success probabilities (e.g. a small drop from 88% to 85% is observed for discrimination of colon cancer). Yet, it can be emphasized that there is an obvious improvement in Study 3 over Study 1. Indeed, for colon cancer the average acceptance probability was increased from 77% to 79% and the success probability from 81% to 85%. This was achieved via the planning of clinical tests. It was required that the first two tests from the six selected (ALBUMIN and ERYTHROCYTES) are mandatory and the other two tests (HEMATOCRIT and HEMOGLOBIN) are used if available in the record. It is possible to assume that if each record had the complete set of the four (at least) tests, the acceptance and success probabilities would be somewhat higher.

Figure 26A:
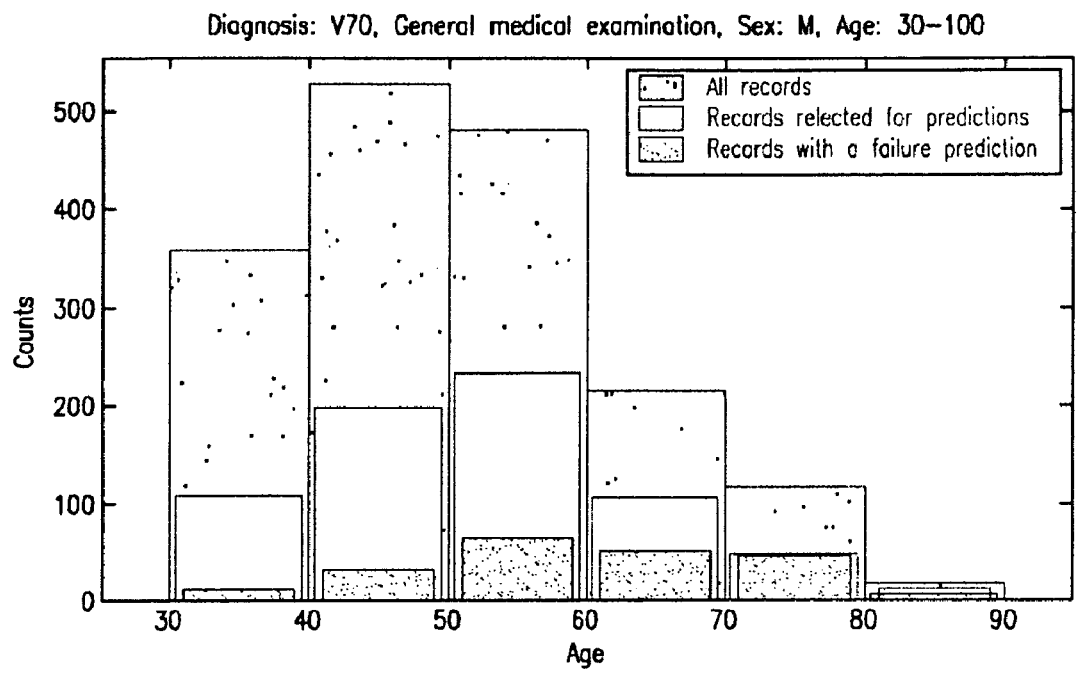
FIGS. 26A-26B are a graphical representation of how records with rejected and failed predictions are distributed over age.
Figure 26B:
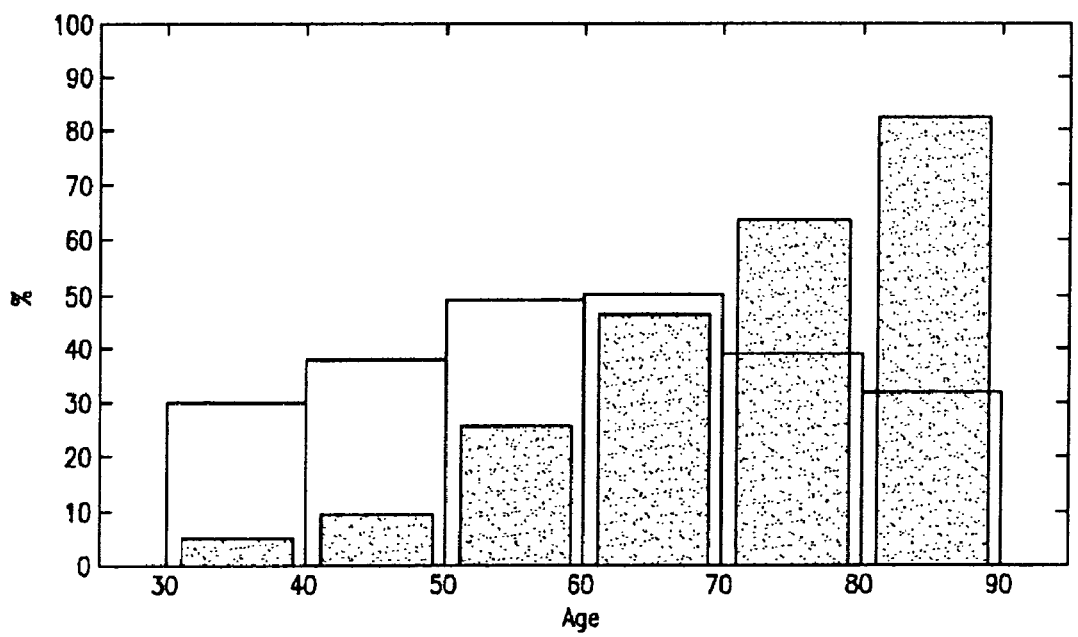

Further evidence will be provided that there is room for further improvement via better accounting for the age factor. FIGS. 26A-26B show an analysis of how the rejected and failed predictions are distributed over age. The results correspond to the DBA simulations in Study 3. It is apparent that the DBA's performance significantly drops with the patient's age. The DBA tuned to different age groups will improve this situation (but, more statistics are needed to tune the DBA for different age groups).

Overall, it is believed that the development of the multiple-diagnosis DBA (robust, tuned to age and other factors) will further improve the discrimination process via fusing the data from a large number of clinical tests.

5. Example of Multiple-Diagnoses DBA

Figure 27A:
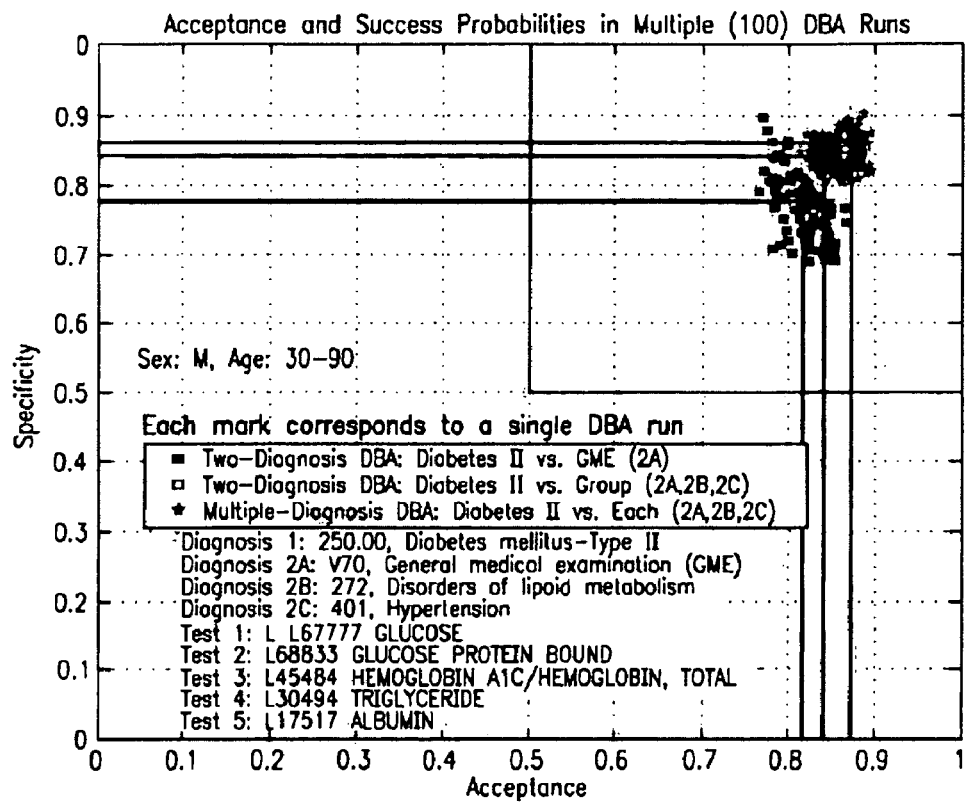
FIGS. 27A-27B are a graphical representation of the assessment of the DBA performance in terms of acceptance/sensitivity (upper) and acceptance/specificity (lower) via Monte-Carlo simulations.
Figure 27B:
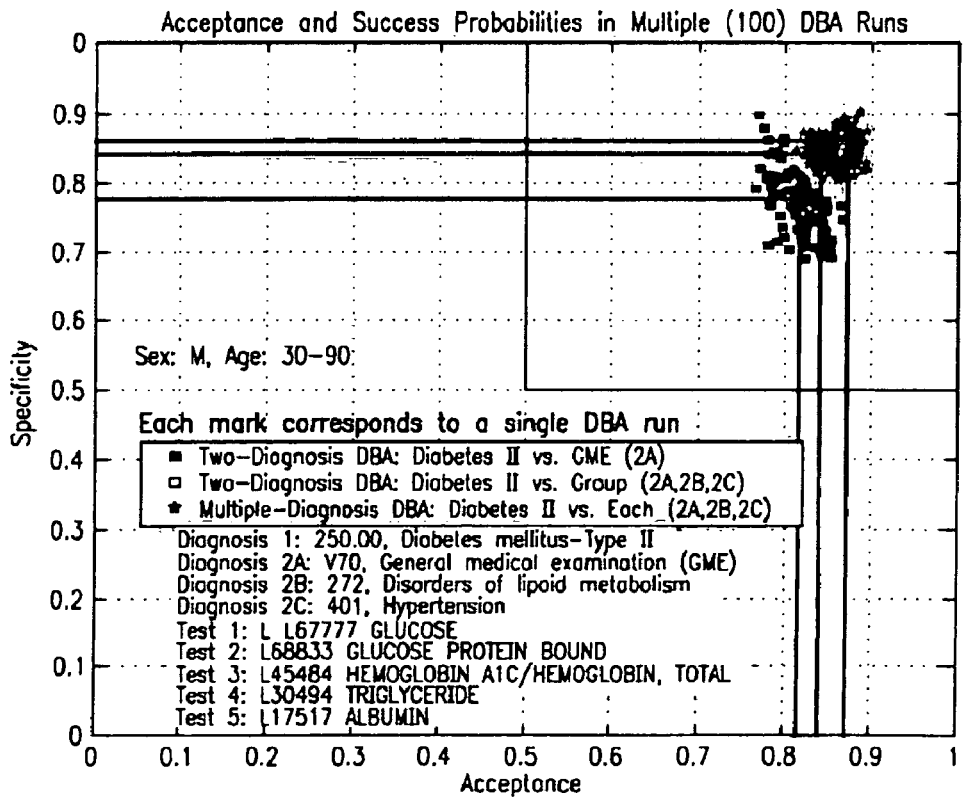

This short example illustrates the application of the DBA for multiple diagnostics. FIGS. 27A-27B present the preliminary simulation results (this is an on-going work). The three different scenarios were studied:

(1) Two-diagnosis DBA to discriminate 250.00 (Diabetes Type II) from V70 (GME);
(2) Two-diagnosis DBA to discriminate 250.00 from a group (GME, Disorders of lipid metabolism, hypertension); and
(3) Multiple-diagnosis DBA to discriminate 250.00 from a group (GME, Disorders of lipid metabolism, hypertension).

In FIGS. 27A-27B, each scatter point corresponds to a single DBA run. In each run was used a different division of the available data into training and control sets. The volume of the data was about 200-300 records in each set (including divisions with respect to Sex and Age). Due to a limited number of records, the probabilities are scattered, and the DBA's performance (sensitivity, specificity and acceptance) is estimated statistically.

Scenario 1 involves only two possible hypotheses and that is why the performance is the highest (as can be seen from FIGS. 27A-27B). Scenario 2 is more realistic since other diseases are involved in diagnosing. The DBA's performance drops since it uses the two-diagnosis discrimination. In this case the distributions of GME, 272, and 401 in the multi-dimensional space of clinical tests are combined in one distribution. This reduces the sensitivity/specificity/acceptance of the statistical screening test for diagnosing Diabetes Type II. Using a multiple-diagnosis DBA (Scenario 3) significantly improves on the specificity/sensitivity/acceptance of the statistical screening test based on the five clinical tests. The mechanism of this improvement is in the fact that the multiple-diagnosis DBA exploits the differential patterns of disease pairs in the space of multiple clinical tests (instead of projecting these patterns into a "group" pattern).

6. Computer Implementation

The processes described above for data analysis, calculation of probabilities, identification of diagnoses, and the like can be performed by a computer process using conventional programming techniques. A variety of operating systems can be used and a variety of application programming languages can be used by those skilled in the art to provide an application that, when executed, will perform the operations described above. Any conventional computer can be used to provide the programming environment necessary to execution of programming operations in accordance with the invention, so long as the programming environment is sufficient to support the required operations.

Figure 29:
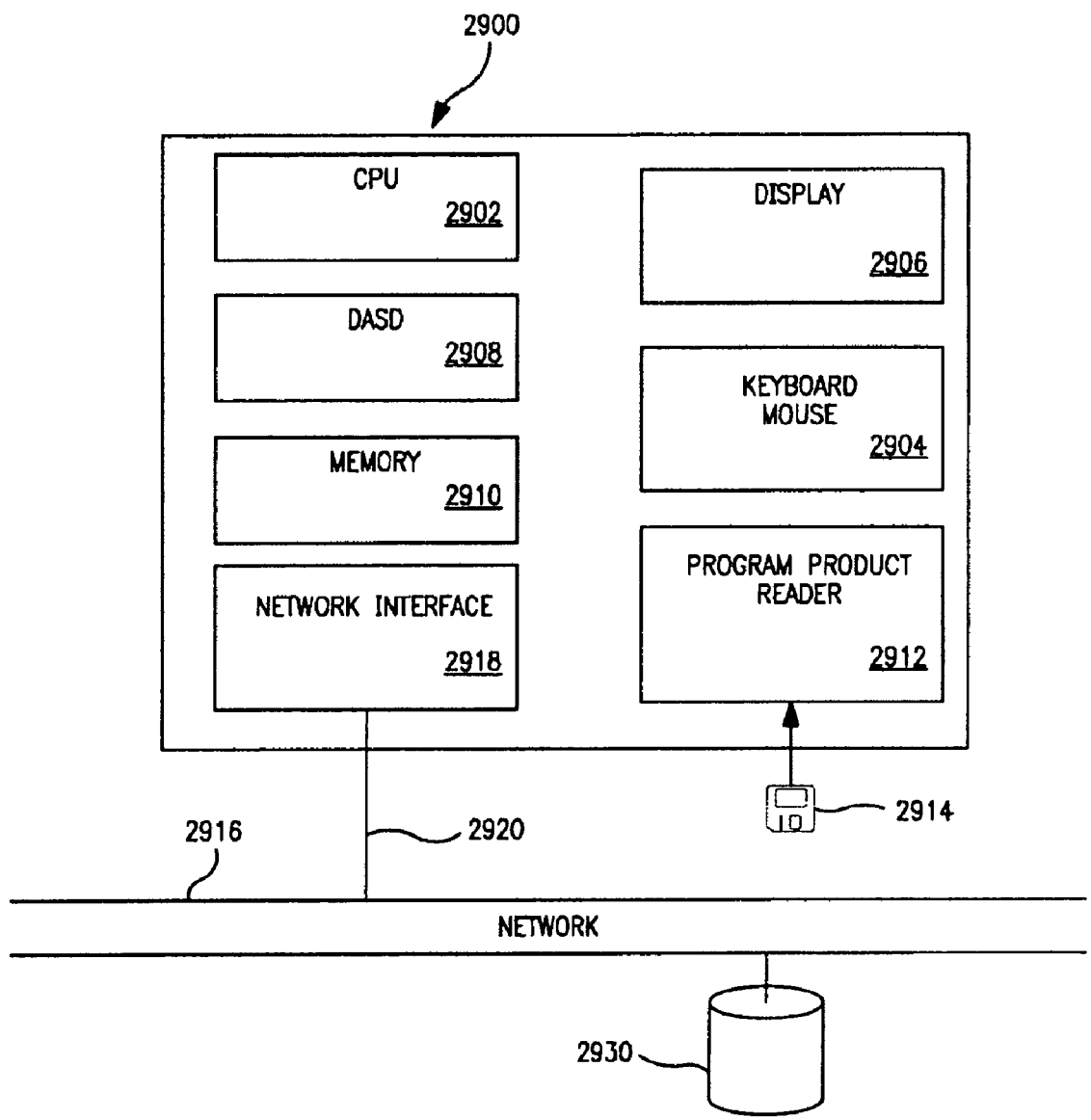
FIG. 29 is a block diagram of a computer system that can be used to implement the data operations in accordance with the invention.

FIG. 29 is a block diagram of an exemplary computer 2900 such as might comprise a computer for performing the data processing operations described above. The computer 2900 operates under control of a central processor unit (CPU) 2902, such as a "Pentium" microprocessor and associated integrated circuit chips, available from Intel Corporation of Santa Clara, Calif., USA. A computer user can input commands and data from a keyboard and computer mouse 2904, and can view inputs and computer output at a display 2906. The display is typically a video monitor or flat panel display. The computer 2900 also includes a direct access storage device (DASD) 2908, such as a hard disk drive. The memory 2910 typically comprises volatile semiconductor random access memory (RAM). The computer preferably includes a program product reader 2912 that accepts a program product storage device 2914, from which the program product reader can read data (and to which it can optionally write data). The program product reader can comprise, for example, a disk drive, and the program product storage device can comprise removable storage media such as a magnetic floppy disk, a CD-R disc, a CD-RW disc, or DVD disc. The computer 2900 can communicate over a computer network 2916 (such as the Internet or an intranet) through a network interface 2918 that enables communication over a connection 2920 between the network 2916 and the computer. The network interface 2918 typically comprises, for example, a Network Interface Card (NIC) that permits communications over a variety of networks.

The CPU 2902 operates under control of programming steps that are temporarily stored in the memory 2910 of the computer 2900. When the programming steps are executed, the computer performs its functions. The programming steps can be received from the DASD 2908, through the program product storage device 2914, or through the network connection 2920. The program product storage drive 2912 can receive a program product 2914, read programming steps recorded thereon, and transfer the programming steps into the memory 2910 for execution by the CPU 2902. As noted above, the program product storage device can comprise anyone of multiple removable media having recorded computer-readable instructions, including magnetic floppy disks and CD-ROM storage discs. Other suitable program product storage devices can include magnetic tape and semiconductor memory chips. In this way, the processing steps necessary for operation in accordance with the invention can be embodied on a program product.

Alternatively, the program steps can be received into the operating memory 2910 over the network 2916. In the network method, the computer receives data including program steps into the memory 2910 through the network interface 2918 after network communication has been established over the network connection 2920 by well-known methods that will be understood by those skilled in the art without further explanation. The program operations are then executed by the CPU 2902. The program operations can include the processes described above, such as the processes and operations illustrated in FIG. 11 and FIG. 12. In performing the probability estimation and disease prediction in accordance with the invention, the computer 2900 can acquire the test data for operations, and any other required data for producing the output, from its memory 2910, from removable data media 2914, or from a network database source 2930, or from operator input via the keyboard/mouse 2904 or other input device.

The present invention has been described above in terms of an embodiment so that an understanding of the present invention can be conveyed. There are, however, many configurations for a computer system not specifically described herein but with which the present invention is applicable. The present invention should therefore not be seen as limited to the particular embodiment described herein, but rather, it should be understood that the present invention has wide applicability with respect to disease diagnosis generally. All modifications, variations, or equivalent arrangements and implementations that are within the scope of the attached claims should therefore be considered within the scope of the invention.

We claim:

1. A computer-implemented method of processing test data, comprising:
 determining, by a computer specifically programmed therefor, a set of posterior test-conditional probability density functions (pdf) $p(H_k|x)$ for a set H of hypotheses relating to a set X of test data conditioned on the test data based on (i) an estimate for one or more hypothesis-conditional pdf $p(x|H_k)$ for the test data conditioned on the hypotheses and (ii) a set of prior pdf $p(H_k)$ for each hypothesis;
 wherein the $p(x|H_k)$ estimates include (a) a global estimate produced in accordance with uncertainties in the statistical characteristics of the test data relating to each hypothesis-conditional pdf $p(x|H_k)$ and (b) a local estimate produced in accordance with a discrete neighbor counting process for the test data relative to the global estimate for the corresponding hypothesis-conditional pdf.

2. The computer-implemented method of claim 1, wherein the uncertainties in the statistical characteristics are specified as an ellipsoid about the test data for each hypothesis and each ellipsoid is defined by an m-dimensional ellipsoid $E_{q,k}$ for each hypothesis $H_k$ and is specified by:

$$E_{q,k} = \{x : (x - m_{x,k})^T P^{-1}_{x,k} (x - m_{x,k}) \leq \mu^2_{q,k}\}$$

where the in m×1 vector x is the argument in the space of test data, the m×1 vector $m_{x,k}$ is the mean (center) of each ellipsoid, the in m×m matrix $P_{x,k}$ is a covariance matrix of the ellipsoid, and the scalar $\mu^2_{q,k}$ defines the size of the q-th ellipsoid, such that the global estimate of the hypothesis-conditional pdf is specified by:

$$\hat{P}_{glob}(x|H_k) = \alpha_{q,k} \text{ if } x \in E_{q,k} \cap E_{q-1,k}, (E_{0,k} = E_{l,k}), k=1,\ldots,N$$

for a selected confidence-interval parameter $\alpha_{q,k}$.

3. The computer-implemented method of claim 1, wherein the local estimate for a hypothesis is specified as a probability that an observed vector of tests x and an associated discrete neighbor counting pattern $\{C_{l,k}(x)\}, l=1,\ldots,L_k, k=1,\ldots,N$ might actually be observed, wherein the neighbor counting pattern comprises counting neighbors in the distance layers for each class: $\{C_{l,k}\}, l=1,\ldots,L_k$, wherein the integer $C_{l,k}$ is the number of neighbors associated with the k-th hypothesis whose test values are distanced from a next test value within the l-th globally-transformed distance layer for the k-th class:

$$C_{l,k} = \sum_{i}^{n_k} \vartheta_{l,i,k}, \vartheta_{l,i,k} = \begin{cases} 1 & \text{if } \bar{d}_{l-1,k} < d_{i,k} \leq \bar{d}_{l,k}, \bar{d}_{0,k} = 0 \\ 0 & \text{otherwise} \end{cases}$$

where $n_k$ is the total number of data records in a selected k-th class and the index i runs over all these data records.

4. The computer-implemented method of claim 3, wherein the selected k-th class of the test data corresponds to a selected training subset class of the test data.

5. The computer-implemented method of claim 1, further including:
 performing a training mode in which a training subset class of the test data is used to produce the hypothesis-conditional probability density functions $p(x|H_k)$; and
 performing a prediction mode in which a set of posterior probabilities is determined for the set H of hypotheses, wherein the hypothesis-conditional probability density functions $p(x|H^k)$ are produced from the global estimates and from the local estimate.

6. The computer-implemented method of claim 5, wherein the selected k-th class of the test data corresponds to the training subset class of the test data.

7. The computer-implemented method of claim 1, wherein the posterior test-condition probabilities provide a diagnosis or risk of developing a disease or diseases.

8. The computer-implemented method of claim 7, wherein the data comprises biochemical data from a subject.

9. The computer-implemented method of claim 7, wherein the data comprises medical history data from a subject.

10. The computer-implemented method of claim 7, wherein the data comprises physiological data from a subject.

11. The computer-implemented method of claim 7, wherein the data comprises clinical data from a subject.

12. The computer-implemented method of claim 7, wherein the diseases are selected from the group consisting of cardiovascular diseases, diabetes, neurodegenerative diseases, malignancies, ophthalmic diseases, blood diseases, respiratory diseases, endocrine diseases, bacterial, parasitic, fungal or viral infections, inflammatory diseases, autoimmune diseases, and reproductive diseases.

13. A non-transitory computer readable medium containing instructions stored therein for causing a computer processor to perform a method comprising:
 determining a set of posterior test-conditional probability density functions (pdf) $p(H_k|x)$ for a set H of hypotheses relating to a set X of test data conditioned on the test data based on (i) an estimate for one or more hypothesis-conditional pdf $p(x|H_k)$ for the test data conditioned on the hypotheses and (ii) a set of prior pdf $p(H_k)$ for each hypothesis;
 wherein the $p(x|H_k)$ estimates include (a) a global estimate produced in accordance with uncertainties in the statistical characteristics of the test data relating to each hypothesis-conditional pdf $p(x|H_k)$ and (b) a local estimate produced in accordance with a discrete neighbor counting process for the test data relative to the global estimate for the corresponding hypothesis-conditional pdf.

14. The non-transitory computer readable medium as defined in claim 13, wherein the uncertainties in the statistical characteristics are specified as an ellipsoid about the test data for each hypothesis and each ellipsoid is defined by an m-dimensional ellipsoid $E_{q,k}$ for each hypothesis $H_k$ and is specified by:

$$E_{q,k}=\{x:(x-m_{x,k})^T P_{x,k}^{-1}(x-m_{x,k})\leq \mu_{q,k}^2\}$$

where the m×1 vector x is the argument in the space of test data, the m×1 vector $m_{x,k}$ is the mean (center) of each ellipsoid, the m×m matrix $P_{x,k}$ is a covariance matrix of the ellipsoid, and the scalar $\mu^2_{q,k}$ defines the size of the q-th ellipsoid, such that the global estimate of the hypothesis-conditional pdf is specified by:

$$\hat{P}_{glob}(x|H_k)=\alpha_{q,k} \text{ if } x\in E_{q,k}\cap E_{q-1,k}), (E_{0,k}=E_{l,k}), k=1,\ldots,N$$

for a selected confidence interval parameter $\alpha_{q,k}$.

15. The non-transitory computer readable medium as defined in claim 13, wherein the local estimate for a hypothesis is specified as a probability that an observed vector of tests x and an associated discrete neighbor counting pattern $\{C_{l,k}(x)\}, l=1,\ldots,L_k, k=1,\ldots,N$ might actually be observed, wherein the neighbor counting pattern comprises counting neighbors in the distance layers for each class: $\{C_{l,k}\}, l=1,\ldots,L_k$, wherein the integer $C_{l,k}$ is the number of test elements associated with the k-th hypothesis whose test values are distanced from a next test value within the l-th globally-transformed distance layer for the k-th class:

$$C_{l,k}=\sum_{i}^{n_k} \vartheta_{l,i,k}, \vartheta_{l,i,k}=\begin{cases} 1 & \text{if } \overline{d}_{l-1,k}<d_{i,k}\leq \overline{d}_{l,k}, \overline{d}_{0,k}=0 \\ 0 & \text{otherwise} \end{cases}$$

where $n_k$ is the total number of data records in a selected k-th class and the index i runs over all these data records.

16. The non-transitory computer readable medium as defined in claim 15, wherein the selected k-th class of the test data corresponds to a selected training subset class of the test data.

17. The non-transitory computer readable medium as defined in claim 13, further including:
performing a training mode in which a training subset class of the test data is used to produce the hypothesis-conditional probability density functions $p(x|H_k)$; and
performing a prediction mode in which a set of posterior probabilities is determined for the set H of hypotheses, wherein the hypothesis-conditional probability density functions $p(x|H_k)$ are produced from the global estimates and from the local estimate.

18. The non-transitory computer readable medium as defined in claim 17, wherein the selected k-th class of the test data corresponds to the training subset class of the test data.

19. The non-transitory computer readable medium as defined in claim 13, wherein the posterior test-condition probabilities provide a diagnosis or risk of developing a disease or diseases.

20. The non-transitory computer readable medium as defined in claim 19, wherein the data comprises biochemical data from a subject.

21. The non-transitory computer readable medium as defined in claim 19, wherein the data comprises medical history data from a subject.

22. The non-transitory computer readable medium as defined in claim 19, wherein the data comprises physiological data from a subject.

23. The non-transitory computer readable medium as defined in claim 19, wherein the data comprises clinical data from a subject.

24. The non-transitory computer readable medium as defined in claim 19, wherein the diseases are selected from the group consisting of cardiovascular diseases, diabetes, neurodegenerative diseases, malignancies, ophthalmic diseases, blood diseases, respiratory diseases, endocrine diseases, bacterial, parasitic, fungal or viral infections, inflammatory diseases, autoimmune diseases, and reproductive diseases.

* * * * *